United States Patent
Pearson

(10) Patent No.: US 11,957,405 B2
(45) Date of Patent: *Apr. 16, 2024

(54) METHODS OF STERILIZATION AND TREATING INFECTION USING IRREVERSIBLE ELECTROPORATION

(71) Applicant: AngioDynamics, Inc., Latham, NY (US)

(72) Inventor: Robert Pearson, San Jose, CA (US)

(73) Assignee: ANGIODYNAMICS, INC., Latham, NY (US)

(*) Notice: Subject to any disclaimer, the term of this patent is extended or adjusted under 35 U.S.C. 154(b) by 276 days.

This patent is subject to a terminal disclaimer.

(21) Appl. No.: 17/073,039

(22) Filed: Oct. 16, 2020

(65) Prior Publication Data

US 2021/0030463 A1    Feb. 4, 2021

Related U.S. Application Data

(63) Continuation of application No. 15/864,421, filed on Jan. 8, 2018, now abandoned, which is a continuation
(Continued)

(51) Int. Cl.
*A61B 18/00* (2006.01)
*A61B 18/14* (2006.01)
(Continued)

(52) U.S. Cl.
CPC ............ *A61B 18/1477* (2013.01); *A61B 2018/00577* (2013.01); *A61B 2018/00613* (2013.01);
(Continued)

(58) Field of Classification Search
CPC ...... A61B 18/1477; A61B 2018/00577; A61B 2018/00613; A61B 2018/124; A61B 2018/1467
See application file for complete search history.

(56) References Cited

U.S. PATENT DOCUMENTS 1,329,496 A    2/1920    Binkley
1,351,661 A    8/1920    Francois
(Continued)

FOREIGN PATENT DOCUMENTS

AU        7656800 A      4/2001
AU     2002315095 A1    12/2002
(Continued)

OTHER PUBLICATIONS

Gowrishankar T.R., et al., "Microdosimetry for conventional and supra-electroporation in cells with organelles". Biochem Biophys Res Commun, 341(4): p. 1266-1276 (2006).
(Continued)

*Primary Examiner* — Daniel W Fowler
(74) *Attorney, Agent, or Firm* — DLA PIPER LLP (US)

(57) ABSTRACT

A method for treating an infection using irreversible electroporation is presented. The method includes providing an ablation device that has at least one electrode and inserting the ablation device into a target tissue of a patient. The tissue at least partially surrounds the implanted medical device. The outer surface of the medical device is at least partially covered by infectious cells. The method also involves positioning at least one electrode in or near the implanted medical device and delivering electrical pulses to or near the implanted medical device sufficient to irreversibly electroporate the infectious cells.

17 Claims, 38 Drawing Sheets

Related U.S. Application Data of application No. 14/302,678, filed on Jun. 12, 2014, now Pat. No. 9,895,189.

(60) Provisional application No. 61/834,471, filed on Jun. 13, 2013.

(51) Int. Cl.
    *A61B 18/12* (2006.01)
    *A61B 34/00* (2016.01)

(52) U.S. Cl.
    CPC . *A61B 2018/124* (2013.01); *A61B 2018/1467* (2013.01); *A61B 2034/252* (2016.02); *A61B 2034/254* (2016.02)

(56) References Cited

U.S. PATENT DOCUMENTS

| | | |
|---|---|---|
| 1,376,652 A | 5/1921 | Steedman |
| 1,380,272 A | 5/1921 | Tomasulo |
| 1,430,015 A | 9/1922 | Icher |
| 1,437,941 A | 12/1922 | Hoover |
| 1,442,697 A | 1/1923 | Orthmann |
| 1,443,360 A | 1/1923 | Grace |
| 1,445,198 A | 2/1923 | Bornmann |
| 1,450,391 A | 4/1923 | Shaw |
| 1,653,819 A | 12/1927 | Northcott |
| 3,437,941 A | 4/1969 | Leary |
| 3,634,460 A | 1/1972 | Nelson |
| 3,639,545 A | 2/1972 | Wilcox |
| 3,730,238 A | 5/1973 | Butler |
| 3,746,004 A | 7/1973 | Jankelson |
| 3,871,359 A | 3/1975 | Pacela |
| 4,016,866 A | 4/1977 | Lawton |
| 4,016,886 A | 4/1977 | Doss |
| 4,037,341 A | 7/1977 | Odle |
| 4,216,860 A | 8/1980 | Heimann |
| 4,224,949 A | 9/1980 | Scott |
| 4,226,246 A | 10/1980 | Fragnet |
| 4,262,672 A | 4/1981 | Kief |
| 4,267,047 A | 5/1981 | Henne |
| 4,278,092 A | 7/1981 | Borsanyi et al. |
| 4,299,217 A | 11/1981 | Sagae et al. |
| 4,304,239 A | 12/1981 | Perlin |
| 4,311,148 A | 1/1982 | Courtney |
| 4,336,881 A | 6/1982 | Babb et al. |
| 4,344,436 A | 8/1982 | Kubota |
| 4,392,855 A | 7/1983 | Oreopoulos |
| 4,406,827 A | 9/1983 | Carim |
| 4,407,943 A | 10/1983 | Cole |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek |
| 4,636,199 A | 1/1987 | Victor |
| 4,672,969 A | 6/1987 | Dew |
| 4,676,258 A | 6/1987 | Inokuchi |
| 4,676,782 A | 6/1987 | Yamamoto |
| 4,687,471 A | 8/1987 | Twardowski |
| 4,716,896 A | 1/1988 | Ackerman |
| 4,723,549 A | 2/1988 | Wholey |
| D294,519 S | 3/1988 | Hardy, Jr. |
| 4,756,838 A | 7/1988 | Veltman |
| 4,772,269 A | 9/1988 | Twardowski |
| 4,798,585 A | 1/1989 | Inoue |
| 4,810,963 A | 3/1989 | Blake-Coleman |
| 4,813,929 A | 3/1989 | Semrad |
| 4,819,637 A | 4/1989 | Dormandy, Jr. |
| 4,822,470 A | 4/1989 | Chang |
| 4,836,204 A | 6/1989 | Landymore |
| 4,840,172 A | 6/1989 | Augustine |
| 4,863,426 A | 9/1989 | Ferragamo |
| 4,885,003 A | 12/1989 | Hillstead |
| 4,886,496 A | 12/1989 | Conoscenti |
| 4,886,502 A | 12/1989 | Poirier et al. |
| 4,889,634 A | 12/1989 | El-Rashidy |
| 4,903,707 A | 2/1990 | Knute |
| 4,907,601 A | 3/1990 | Frick |
| 4,919,148 A | 4/1990 | Muccio |
| 4,921,484 A | 4/1990 | Muccio |
| 4,920,978 A | 5/1990 | Colvin |
| 4,946,793 A | 8/1990 | Marshall, III |
| 4,976,709 A | 12/1990 | Sand |
| 4,981,477 A | 1/1991 | Schon |
| 4,986,810 A | 1/1991 | Semrad |
| 4,987,895 A | 1/1991 | Heimlich |
| 5,019,034 A | 5/1991 | Weaver |
| 5,031,775 A | 7/1991 | Kane |
| 5,052,391 A | 10/1991 | Silberstone |
| 5,053,013 A | 10/1991 | Ensminger |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney |
| 5,141,499 A | 8/1992 | Zappacosta |
| D329,496 S | 9/1992 | Wotton |
| 5,156,597 A | 10/1992 | Verreet |
| 5,173,158 A | 12/1992 | Schmukler |
| 5,186,715 A | 2/1993 | Phillips |
| 5,186,800 A | 2/1993 | Dower |
| 5,188,592 A | 2/1993 | Hakki |
| 5,190,541 A | 3/1993 | Abele |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,222,997 A | 6/1993 | Montgomery |
| 5,224,933 A | 7/1993 | Bromander |
| 5,227,730 A | 7/1993 | King |
| 5,242,415 A | 9/1993 | Kantrowitz et al. |
| 5,273,525 A | 12/1993 | Hofmann |
| D343,687 S | 1/1994 | Houghton, II |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross |
| 5,318,563 A | 6/1994 | Malis |
| 5,328,451 A | 7/1994 | Davis |
| 5,334,167 A | 8/1994 | Cocanower |
| 5,348,554 A | 9/1994 | Imran |
| D351,661 S | 10/1994 | Fischer |
| 5,383,917 A | 1/1995 | Desai |
| 5,389,069 A | 2/1995 | Weaver |
| 5,391,158 A | 2/1995 | Peters |
| 5,403,311 A | 4/1995 | Abele |
| 5,405,320 A | 4/1995 | Twardowski et al. |
| 5,417,687 A | 5/1995 | Nardella |
| 5,424,752 A | 6/1995 | Yamazaki |
| 5,425,752 A | 6/1995 | Vu Nguyen |
| 5,439,440 A | 8/1995 | Hofmann |
| 5,439,444 A | 8/1995 | Andersen |
| 5,458,597 A | 10/1995 | Edwards |
| 5,458,625 A | 10/1995 | Kendall |
| 5,462,521 A | 10/1995 | Brucker |
| 5,462,644 A | 10/1995 | Woodson |
| 5,484,400 A | 1/1996 | Edwards |
| 5,484,401 A | 1/1996 | Rodriguez |
| 5,533,999 A | 7/1996 | Hood |
| 5,536,240 A | 7/1996 | Edwards |
| 5,536,267 A | 7/1996 | Edwards |
| 5,540,737 A | 7/1996 | Fenn |
| 5,542,916 A | 8/1996 | Hirsch |
| 5,546,940 A | 8/1996 | Panescu et al. |
| 5,562,720 A | 10/1996 | Stern et al. |
| 5,575,811 A | 11/1996 | Reid |
| D376,652 S | 12/1996 | Hunt |

(56) References Cited

U.S. PATENT DOCUMENTS

| | | | |
|---|---|---|---|
| 5,582,588 | A | 12/1996 | Sakurai et al. |
| 5,586,982 | A | 12/1996 | Abela |
| 5,588,424 | A | 12/1996 | Insler |
| 5,588,960 | A | 12/1996 | Edwards et al. |
| 5,599,294 | A | 2/1997 | Edwards |
| 5,599,311 | A | 2/1997 | Raulerson |
| 5,616,126 | A | 4/1997 | Malekmehr |
| 5,620,479 | A | 4/1997 | Diederich |
| 5,626,146 | A | 5/1997 | Barber |
| 5,630,426 | A | 5/1997 | Eggers et al. |
| D380,272 | S | 6/1997 | Partika |
| 5,634,899 | A | 6/1997 | Shapland |
| 5,643,197 | A | 7/1997 | Brucker |
| 5,645,855 | A | 7/1997 | Lorenz |
| 5,653,684 | A | 8/1997 | Laptewicz |
| 5,672,173 | A | 9/1997 | Gough |
| 5,672,174 | A | 9/1997 | Gough |
| 5,674,267 | A | 10/1997 | Mir |
| 5,681,282 | A | 10/1997 | Eggers |
| 5,683,384 | A | 11/1997 | Gough et al. |
| 5,687,723 | A | 11/1997 | Avitall |
| 5,690,620 | A | 11/1997 | Knott |
| 5,697,905 | A | 12/1997 | d'Ambrosio |
| 5,700,252 | A | 12/1997 | Klingenstein |
| 5,702,359 | A | 12/1997 | Hofmann |
| 5,707,332 | A | 1/1998 | Weinberger |
| 5,718,246 | A | 2/1998 | Vona |
| 5,720,921 | A | 2/1998 | Meserol |
| 5,728,143 | A | 3/1998 | Gough |
| 5,735,847 | A | 4/1998 | Gough et al. |
| 5,749,914 | A | 5/1998 | Janssen |
| 5,752,939 | A | 5/1998 | Makoto |
| 5,778,894 | A | 7/1998 | Dorogi |
| 5,782,827 | A | 7/1998 | Gough et al. |
| 5,782,882 | A | 7/1998 | Lerman |
| 5,800,378 | A | 9/1998 | Edwards |
| 5,800,484 | A | 9/1998 | Gough et al. |
| 5,807,272 | A | 9/1998 | Kun et al. |
| 5,807,306 | A | 9/1998 | Shapland |
| 5,807,395 | A | 9/1998 | Mulier |
| 5,810,742 | A | 9/1998 | Pearlman |
| 5,810,762 | A | 9/1998 | Hofmann |
| 5,810,804 | A | 9/1998 | Gough |
| 5,830,184 | A | 11/1998 | Basta |
| 5,836,897 | A | 11/1998 | Sakurai et al. |
| 5,836,905 | A | 11/1998 | Lemelson |
| 5,843,026 | A | 12/1998 | Edwards |
| 5,843,182 | A | 12/1998 | Goldstein |
| 5,856,081 | A | 1/1999 | Fahy |
| 5,863,290 | A | 1/1999 | Gough et al. |
| 5,865,787 | A | 2/1999 | Shapland et al. |
| 5,866,756 | A | 2/1999 | Giros et al. |
| 5,868,708 | A | 2/1999 | Hart |
| 5,873,849 | A | 2/1999 | Bernard |
| 5,873,877 | A | 2/1999 | McGaffigan |
| 5,904,648 | A | 5/1999 | Arndt et al. |
| 5,913,855 | A | 6/1999 | Gough et al. |
| 5,919,142 | A | 7/1999 | Boone |
| 5,919,191 | A | 7/1999 | Lennox et al. |
| 5,921,982 | A | 7/1999 | Lesh |
| 5,944,710 | A | 8/1999 | Dev et al. |
| 5,947,284 | A | 9/1999 | Foster |
| 5,947,889 | A | 9/1999 | Hehrlein |
| 5,951,546 | A | 9/1999 | Lorentzen |
| 5,954,745 | A | 9/1999 | Gertler |
| 5,957,919 | A | 9/1999 | Laufer |
| 5,957,963 | A | 9/1999 | Dobak, III |
| 5,968,006 | A | 10/1999 | Hofmann |
| 5,983,131 | A | 11/1999 | Weaver |
| 5,983,140 | A | 11/1999 | Smith |
| 5,984,896 | A | 11/1999 | Boyd |
| 5,991,697 | A | 11/1999 | Nelson |
| 5,993,466 | A | 11/1999 | Yoon |
| 5,999,847 | A | 12/1999 | Elstrom |
| 6,004,339 | A | 12/1999 | Wijay |
| 6,009,347 | A | 12/1999 | Hofmann |
| 6,009,877 | A | 1/2000 | Edwards |
| 6,010,452 | A | 1/2000 | Harcourt |
| 6,010,613 | A | 1/2000 | Walters |
| 6,012,885 | A | 1/2000 | Taylor |
| 6,016,452 | A | 1/2000 | Kasevich |
| 6,023,638 | A | 2/2000 | Swanson |
| 6,029,090 | A | 2/2000 | Herbst |
| 6,041,252 | A | 3/2000 | Walker et al. |
| 6,043,066 | A | 3/2000 | Mangano |
| 6,050,994 | A | 4/2000 | Sherman |
| 6,055,453 | A | 4/2000 | Hofmann |
| 6,059,780 | A | 5/2000 | Gough |
| 6,066,134 | A | 5/2000 | Eggers et al. |
| 6,068,121 | A | 5/2000 | McGlinch |
| 6,068,650 | A | 5/2000 | Hofmann |
| 6,071,281 | A | 6/2000 | Burnside |
| 6,074,374 | A | 6/2000 | Fulton |
| 6,074,389 | A | 6/2000 | Levine et al. |
| 6,085,115 | A | 7/2000 | Weaver |
| 6,090,016 | A | 7/2000 | Kuo |
| 6,090,105 | A | 7/2000 | Zepeda et al. |
| 6,090,106 | A | 7/2000 | Goble |
| D430,015 | S | 8/2000 | Himbert |
| 6,096,035 | A | 8/2000 | Sodhi |
| 6,102,885 | A | 8/2000 | Bass |
| 6,106,521 | A | 8/2000 | Blewett |
| 6,106,524 | A | 8/2000 | Eggers et al. |
| 6,109,270 | A | 8/2000 | Mah et al. |
| 6,110,192 | A | 8/2000 | Ravenscroft et al. |
| 6,113,593 | A | 9/2000 | Tu |
| 6,116,330 | A | 9/2000 | Salyer |
| 6,120,493 | A | 9/2000 | Hofmann |
| 6,122,599 | A | 9/2000 | Mehta |
| 6,123,701 | A | 9/2000 | Nezhat |
| 6,132,397 | A | 10/2000 | Davis et al. |
| 6,132,419 | A | 10/2000 | Hofmann |
| 6,134,460 | A | 10/2000 | Chance |
| 6,139,544 | A | 10/2000 | Mikus |
| 6,139,545 | A | 10/2000 | Utley et al. |
| 6,142,992 | A | 11/2000 | Cheng |
| 6,150,148 | A | 11/2000 | Nanda |
| 6,152,923 | A | 11/2000 | Ryan |
| 6,159,163 | A | 12/2000 | Strauss |
| 6,178,354 | B1 | 1/2001 | Gibson |
| D437,941 | S | 2/2001 | Frattini |
| 6,193,715 | B1 | 2/2001 | Wrublewski et al. |
| 6,198,970 | B1 | 3/2001 | Freed |
| 6,200,314 | B1 | 3/2001 | Sherman |
| 6,208,893 | B1 | 3/2001 | Hofmann |
| 6,210,402 | B1 | 4/2001 | Olsen |
| 6,212,433 | B1 | 4/2001 | Behl |
| 6,216,034 | B1 | 4/2001 | Hofmann |
| 6,219,577 | B1 | 4/2001 | Brown, III |
| D442,697 | S | 5/2001 | Hajianpour |
| 6,233,490 | B1 | 5/2001 | Kasevich |
| 6,235,023 | B1 | 5/2001 | Lee |
| D443,360 | S | 6/2001 | Haberland |
| 6,241,702 | B1 | 6/2001 | Lundquist |
| 6,241,725 | B1 | 6/2001 | Cosman |
| D445,198 | S | 7/2001 | Frattini |
| 6,258,100 | B1 | 7/2001 | Alferness |
| 6,258,249 | B1 * | 7/2001 | Simpson ............ A61L 2/03 205/687 |
| 6,261,831 | B1 | 7/2001 | Agee |
| 6,277,114 | B1 | 8/2001 | Bullivant et al. |
| 6,278,895 | B1 | 8/2001 | Bernard |
| 6,280,441 | B1 | 8/2001 | Ryan |
| 6,283,988 | B1 | 9/2001 | Laufer |
| 6,283,989 | B1 | 9/2001 | Laufer |
| 6,284,140 | B1 | 9/2001 | Sommermeyer |
| 6,287,293 | B1 | 9/2001 | Jones et al. |
| 6,287,304 | B1 | 9/2001 | Eggers et al. |
| 6,296,636 | B1 | 10/2001 | Cheng |
| 6,298,726 | B1 | 10/2001 | Adachi |
| 6,299,633 | B1 | 10/2001 | Laufer |
| 6,300,108 | B1 | 10/2001 | Rubinsky et al. |
| D450,391 | S | 11/2001 | Hunt |
| 6,312,428 | B1 | 11/2001 | Eggers |

(56) References Cited

U.S. PATENT DOCUMENTS

| | | |
|---|---|---|
| 6,326,177 B1 | 12/2001 | Schoenbach |
| 6,327,505 B1 | 12/2001 | Medhkour |
| 6,328,689 B1 | 12/2001 | Gonzalez et al. |
| 6,328,735 B1 | 12/2001 | Curley |
| 6,330,478 B1 | 12/2001 | Lee |
| 6,347,247 B1 | 2/2002 | Dev |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky |
| 6,398,779 B1 | 6/2002 | Buysse |
| 6,403,347 B1 | 6/2002 | Bills |
| 6,403,348 B1 | 6/2002 | Rubinsky |
| 6,405,732 B1 | 6/2002 | Edwards |
| 6,411,852 B1 | 6/2002 | Danek |
| 6,419,674 B1 | 7/2002 | Bowser |
| 6,428,802 B1 | 8/2002 | Atala |
| 6,437,551 B1 | 8/2002 | Krulevitch |
| 6,443,952 B1 | 9/2002 | Muller et al. |
| 6,463,331 B1 | 10/2002 | Edwards |
| 6,470,211 B1 | 10/2002 | Ideker |
| 6,478,793 B1 | 11/2002 | Cosman |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer |
| 6,488,678 B2 | 12/2002 | Sherman |
| 6,488,680 B1 | 12/2002 | Francischelli et al. |
| 6,491,706 B1 | 12/2002 | Alferness |
| 6,493,569 B2 | 12/2002 | Foo |
| 6,493,589 B1 | 12/2002 | Medhkour |
| 6,493,592 B1 | 12/2002 | Leonard |
| 6,497,704 B2 | 12/2002 | Ein-Gal |
| 6,500,173 B2 | 12/2002 | Underwood |
| 6,503,248 B1 | 1/2003 | Levine |
| 6,506,189 B1 | 1/2003 | Rittman, III et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael |
| D471,641 S | 3/2003 | McMichael |
| 6,530,922 B2 | 3/2003 | Cosman |
| 6,533,784 B2 | 3/2003 | Truckai |
| 6,537,976 B1 | 3/2003 | Gupta |
| 6,540,695 B1 | 4/2003 | Burbank |
| 6,558,378 B2 | 5/2003 | Sherman |
| 6,562,604 B2 | 5/2003 | Rubinsky |
| 6,569,162 B2 | 5/2003 | He |
| 6,575,967 B1 | 6/2003 | Leveen |
| 6,575,969 B1 | 6/2003 | Rittman, III |
| 6,589,161 B2 | 7/2003 | Corcoran |
| 6,589,174 B1 | 7/2003 | Chopra et al. |
| 6,592,594 B2 | 7/2003 | Rimbaugh |
| 6,607,529 B1 | 8/2003 | Jones |
| 6,610,054 B1 | 8/2003 | Edwards |
| 6,611,706 B2 | 8/2003 | Avrahami |
| 6,613,211 B1 | 9/2003 | McCormick et al. |
| 6,616,657 B2 | 9/2003 | Simpson |
| 6,627,421 B1 | 9/2003 | Unger et al. |
| D480,816 S | 10/2003 | McMichael |
| 6,634,363 B1 | 10/2003 | Danek et al. |
| 6,638,253 B2 | 10/2003 | Breznock |
| 6,638,275 B1 | 10/2003 | McGaffigan |
| 6,653,091 B1 | 11/2003 | Dunn |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,682,501 B1 | 1/2004 | Nelson |
| 6,689,096 B1 | 2/2004 | Loubens et al. |
| 6,689,127 B1 | 2/2004 | Gough et al. |
| 6,692,493 B2 | 2/2004 | McGovern |
| 6,694,170 B1 | 2/2004 | Mikus |
| 6,694,964 B2 | 2/2004 | Wu |
| 6,694,979 B2 | 2/2004 | Deem |
| 6,694,984 B2 | 2/2004 | Habib |
| 6,695,861 B1 | 2/2004 | Rosenberg |
| 6,697,669 B2 | 2/2004 | Dev |
| 6,697,670 B2 | 2/2004 | Chomenky |
| 6,702,808 B1 | 3/2004 | Kreindel |
| 6,712,811 B2 | 3/2004 | Underwood |
| D489,973 S | 5/2004 | Root |
| 6,733,516 B2 | 5/2004 | Simons |
| 6,753,171 B2 | 6/2004 | Karube |
| 6,761,716 B2 | 7/2004 | Kadhiresan |
| 6,770,070 B1 | 8/2004 | Balbierz |
| D495,807 S | 9/2004 | Agbodoe |
| 6,795,728 B2 | 9/2004 | Chornenky |
| 6,801,804 B2 | 10/2004 | Miller |
| 6,812,204 B1 | 11/2004 | McHale |
| 6,837,886 B2 | 1/2005 | Collins |
| 6,847,848 B2 | 1/2005 | Sterzer |
| 6,860,847 B2 | 3/2005 | Alferness |
| 6,865,416 B2 | 3/2005 | Dev |
| 6,869,430 B2 | 3/2005 | Balbierz |
| 6,881,213 B2 | 4/2005 | Ryan |
| 6,892,099 B2 | 5/2005 | Jaafar |
| 6,895,267 B2 | 5/2005 | Panescu |
| 6,905,480 B2 | 6/2005 | McGuckin, Jr. |
| 6,912,417 B1 | 6/2005 | Bernard |
| 6,926,713 B2 | 8/2005 | Rioux |
| 6,927,049 B2 | 8/2005 | Rubinsky |
| 6,941,950 B2 | 9/2005 | Wilson |
| 6,942,681 B2 | 9/2005 | Johnson |
| 6,958,062 B1 | 10/2005 | Gough |
| 6,960,189 B2 | 11/2005 | Bates |
| 6,962,587 B2 | 11/2005 | Johnson |
| 6,972,013 B1 | 12/2005 | Zhang |
| 6,972,014 B2 | 12/2005 | Eum |
| 6,989,010 B2 | 1/2006 | Francischelli |
| 6,994,689 B1 | 2/2006 | Zadno-Azizi |
| 6,994,706 B2 | 2/2006 | Chornenky |
| 7,008,421 B2 | 3/2006 | Daniel |
| 7,011,094 B2 | 3/2006 | Rapacki |
| 7,012,061 B1 | 3/2006 | Reiss |
| 7,027,869 B2 | 4/2006 | Danek |
| 7,036,510 B2 | 5/2006 | Zgoda |
| 7,053,063 B2 | 5/2006 | Rubinsky |
| 7,054,665 B2 | 5/2006 | Turner |
| 7,054,685 B2 | 5/2006 | Dimmer |
| 7,063,698 B2 | 6/2006 | Whayne |
| 7,087,040 B2 | 8/2006 | McGuckin, Jr. |
| 7,097,612 B2 | 8/2006 | Bertolero |
| 7,100,616 B2 | 9/2006 | Springmeyer |
| 7,113,821 B1 | 9/2006 | Sun |
| 7,130,697 B2 | 10/2006 | Chornenky |
| 7,162,303 B2 | 1/2007 | Levin |
| 7,169,107 B2 | 1/2007 | Jersey-Willuhn |
| 7,211,083 B2 | 5/2007 | Chornenky |
| 7,232,437 B2 | 6/2007 | Berman |
| 7,250,048 B2 | 7/2007 | Francischelli |
| D549,332 S | 8/2007 | Matsumoto |
| 7,257,450 B2 | 8/2007 | Auth |
| 7,264,002 B2 | 9/2007 | Danek |
| 7,267,676 B2 | 9/2007 | Chornenky et al. |
| 7,273,055 B2 | 9/2007 | Danek |
| 7,291,146 B2 | 11/2007 | Steinke |
| 7,331,940 B2 | 2/2008 | Sommerich |
| 7,331,949 B2 | 2/2008 | Marisi |
| 7,341,558 B2 | 3/2008 | De la Torre |
| 7,344,533 B2 | 3/2008 | Pearson |
| D565,743 S | 4/2008 | Phillips |
| D571,478 S | 6/2008 | Horacek |
| 7,387,626 B2 | 6/2008 | Edwards |
| 7,399,747 B1 | 7/2008 | Clair |
| D575,399 S | 8/2008 | Matsumoto |
| D575,402 S | 8/2008 | Sandor |
| 7,412,977 B2 | 8/2008 | Fields |
| 7,419,487 B2 | 9/2008 | Johnson |
| 7,434,578 B2 | 10/2008 | Dillard |
| 7,437,194 B2 | 10/2008 | Skwarek |
| 7,449,019 B2 | 11/2008 | Uchida |
| 7,451,765 B2 | 11/2008 | Adler |
| 7,455,675 B2 | 11/2008 | Schur |

(56) References Cited

U.S. PATENT DOCUMENTS

| | | |
|---|---|---|
| 7,476,203 B2 | 1/2009 | Devore |
| 7,488,292 B2 | 2/2009 | Adachi |
| 7,520,877 B2 | 4/2009 | Lee, Jr. |
| 7,533,671 B2 | 5/2009 | Gonzalez |
| D595,422 S | 6/2009 | Mustapha |
| 7,544,301 B2 | 6/2009 | Shah |
| 7,549,984 B2 | 6/2009 | Mathis |
| 7,553,309 B2 | 6/2009 | Buysse |
| 7,565,208 B2 | 7/2009 | Harris |
| 7,571,729 B2 | 8/2009 | Saadat |
| 7,617,005 B2 | 11/2009 | Demarais |
| 7,620,451 B2 | 11/2009 | Demarais |
| 7,620,507 B2 | 11/2009 | Richardson |
| 7,632,291 B2 | 12/2009 | Stephens |
| 7,647,115 B2 | 1/2010 | Levin |
| 7,653,438 B2 | 1/2010 | Deem |
| 7,655,004 B2 | 2/2010 | Long |
| 7,670,333 B2 | 3/2010 | Schatzberger |
| 7,674,249 B2 | 3/2010 | Ivorra |
| 7,680,543 B2 | 3/2010 | Azure |
| D613,418 S | 4/2010 | Ryan |
| 7,699,842 B2 | 4/2010 | Buysse |
| 7,706,865 B1 | 4/2010 | Snell |
| 7,717,948 B2 | 5/2010 | Demarais |
| 7,718,409 B2 | 5/2010 | Rubinsky |
| 7,722,606 B2 | 5/2010 | Azure |
| 7,742,795 B2 | 6/2010 | Stone |
| 7,763,018 B2 | 7/2010 | DeCarlo |
| 7,765,010 B2 | 7/2010 | Chornenky |
| 7,771,401 B2 | 8/2010 | Hekmat |
| 7,776,035 B2 | 8/2010 | Rick |
| 7,815,571 B2 | 10/2010 | Deckman |
| 7,815,662 B2 | 10/2010 | Spivey |
| 7,824,870 B2 | 11/2010 | Kovalcheck |
| RE42,016 E | 12/2010 | Chornenky et al. |
| 7,846,108 B2 | 12/2010 | Turovskiy |
| 7,853,333 B2 | 12/2010 | Demarais |
| D630,321 S | 1/2011 | Hamilton, Jr. |
| D631,154 S | 1/2011 | Hamilton, Jr. |
| 7,874,986 B2 | 1/2011 | Deckman |
| 7,875,025 B2 | 1/2011 | Cockburn |
| 7,879,031 B2 | 2/2011 | Peterson |
| RE42,277 E | 4/2011 | Jaafar et al. |
| 7,918,852 B2 | 4/2011 | Tullis |
| 7,937,143 B2 | 5/2011 | Demarais |
| 7,938,824 B2 | 5/2011 | Chornenky |
| 7,951,582 B2 | 5/2011 | Gazit |
| 7,955,827 B2 | 6/2011 | Rubinsky |
| RE42,835 E | 10/2011 | Chornenky et al. |
| D647,628 S | 10/2011 | Helfteren |
| 8,029,504 B2 | 10/2011 | Long |
| 8,037,591 B2 | 10/2011 | Spivey |
| 8,048,067 B2 | 11/2011 | Davalos |
| 8,052,604 B2 | 11/2011 | Lau |
| 8,057,391 B2 | 11/2011 | Lau |
| 8,062,290 B2 | 11/2011 | Buysse |
| RE43,009 E | 12/2011 | Chornenky |
| 8,070,759 B2 | 12/2011 | Stefanchik |
| 8,075,572 B2 | 12/2011 | Stefanchik |
| 8,088,072 B2 | 1/2012 | Munrow |
| 8,100,922 B2 | 1/2012 | Griffith |
| 8,109,926 B2 | 2/2012 | Azure |
| 8,114,070 B2 | 2/2012 | Rubinsky |
| 8,114,072 B2 | 2/2012 | Long |
| 8,114,119 B2 | 2/2012 | Spivey |
| 8,131,371 B2 | 3/2012 | Demarals |
| 8,131,372 B2 | 3/2012 | Levin |
| 8,145,316 B2 | 3/2012 | Deem |
| 8,145,317 B2 | 3/2012 | Demarais |
| 8,150,518 B2 | 4/2012 | Levin |
| 8,150,519 B2 | 4/2012 | Demarais |
| 8,150,520 B2 | 4/2012 | Demarais |
| 8,154,288 B2 | 4/2012 | Deimling |
| 8,157,834 B2 | 4/2012 | Conlon |
| 8,162,918 B2 | 4/2012 | Ivorra |
| 8,172,772 B2 | 5/2012 | Zwolinski |
| 8,174,267 B2 | 5/2012 | Brannan |
| 8,175,711 B2 | 5/2012 | Demarais |
| 8,180,433 B2 | 5/2012 | Brannan |
| 8,181,995 B2 | 5/2012 | DeCarlo |
| 8,182,477 B2 | 5/2012 | Orszulak |
| 8,187,269 B2 | 5/2012 | Shadduck |
| 8,187,270 B2 | 5/2012 | Auth |
| 8,206,300 B2 | 6/2012 | Deckman |
| 8,211,097 B2 | 7/2012 | Leyh |
| 8,211,099 B2 | 7/2012 | Buysse |
| 8,211,125 B2 | 7/2012 | Spivey |
| 8,216,161 B2 | 7/2012 | Darlington |
| 8,221,411 B2 | 7/2012 | Francischelli |
| 8,231,603 B2 | 7/2012 | Hobbs |
| 8,240,468 B2 | 8/2012 | Wilkinson |
| 8,241,204 B2 | 8/2012 | Spivey |
| 8,242,782 B2 | 8/2012 | Brannan |
| 8,246,615 B2 | 8/2012 | Behnke |
| 8,248,075 B2 | 8/2012 | Brannan |
| 8,251,986 B2 | 8/2012 | Chornenky |
| 8,252,057 B2 | 8/2012 | Fox |
| 8,262,563 B2 | 9/2012 | Bakos |
| 8,262,577 B2 | 9/2012 | Munrow |
| 8,262,655 B2 | 9/2012 | Ghabrial |
| 8,262,680 B2 | 9/2012 | Swain |
| 8,267,884 B1 * | 9/2012 | Hicks ............... A61B 18/042 604/23 |
| 8,267,927 B2 | 9/2012 | Dalal |
| 8,267,936 B2 | 9/2012 | Hushka |
| 8,277,379 B2 | 10/2012 | Lau |
| 8,282,631 B2 | 10/2012 | Davalos |
| 8,287,527 B2 | 10/2012 | Brannan |
| 8,292,880 B2 | 10/2012 | Prakash |
| 8,298,222 B2 | 10/2012 | Rubinsky |
| 8,303,516 B2 | 11/2012 | Schmitz |
| 8,317,806 B2 | 11/2012 | Coe |
| 8,337,394 B2 | 12/2012 | Vakharia |
| 8,343,144 B2 | 1/2013 | Kleyman |
| 8,346,370 B2 | 1/2013 | Haley |
| 8,347,891 B2 | 1/2013 | Demarais |
| 8,348,921 B2 | 1/2013 | Ivorra |
| 8,348,938 B2 | 1/2013 | Blomgren |
| 8,353,487 B2 | 1/2013 | Trusty |
| 8,353,902 B2 | 1/2013 | Prakash |
| 8,361,006 B2 | 1/2013 | Kraemer |
| 8,361,066 B2 | 1/2013 | Long |
| 8,361,112 B2 | 1/2013 | Carroll, II |
| 8,366,712 B2 | 2/2013 | Bleich |
| 8,377,057 B2 | 2/2013 | Rick |
| 8,380,283 B2 | 2/2013 | Krieg |
| D677,798 S | 3/2013 | Hart |
| 8,394,092 B2 | 3/2013 | Brannan |
| 8,394,102 B2 | 3/2013 | Garabedian |
| 8,398,626 B2 | 3/2013 | Buysse |
| 8,398,641 B2 | 3/2013 | Wallace |
| 8,403,924 B2 | 3/2013 | Behnke |
| 8,403,926 B2 | 3/2013 | Nobis |
| 8,409,200 B2 | 4/2013 | Holcomb |
| 8,409,206 B2 | 4/2013 | Wallace |
| 8,417,328 B2 | 4/2013 | Sarfaty |
| 8,425,455 B2 | 4/2013 | Nentwick |
| 8,425,505 B2 | 4/2013 | Long |
| 8,433,423 B2 | 4/2013 | Demarais |
| 8,437,845 B2 | 5/2013 | Sarfaty |
| 8,439,907 B2 | 5/2013 | Auth |
| 8,444,640 B2 | 5/2013 | Demarais |
| 8,449,538 B2 | 5/2013 | Long |
| 8,454,594 B2 | 6/2013 | Demarais |
| 8,465,464 B2 | 6/2013 | Travis |
| 8,465,484 B2 | 6/2013 | Davalos |
| 8,469,716 B2 | 6/2013 | Fedotov |
| 8,473,067 B2 | 6/2013 | Hastings |
| 8,480,657 B2 | 7/2013 | Bakos |
| 8,480,665 B2 | 7/2013 | DeCarlo |
| 8,480,666 B2 | 7/2013 | Buysse |
| 8,480,689 B2 | 7/2013 | Spivey |
| 8,489,192 B1 | 7/2013 | Hlavka |
| 8,496,574 B2 | 7/2013 | Trusty |

(56) References Cited

U.S. PATENT DOCUMENTS

| | | |
|---|---|---|
| 8,506,485 B2 | 8/2013 | Deckman |
| 8,506,564 B2 | 8/2013 | Long |
| 8,511,317 B2 | 8/2013 | Thapliyal |
| 8,512,329 B2 | 8/2013 | Paulus |
| 8,512,330 B2 | 8/2013 | Epstein |
| 8,518,031 B2 | 8/2013 | Boyden |
| 8,529,563 B2 | 9/2013 | Long |
| 8,542,019 B2 | 9/2013 | Brannan |
| 8,546,979 B2 | 10/2013 | Heeren |
| 8,548,600 B2 | 10/2013 | Deem |
| 8,551,069 B2 | 10/2013 | Demarais |
| 8,551,088 B2 | 10/2013 | Falkenstein |
| 8,551,097 B2 | 10/2013 | Schmitz |
| 8,562,588 B2 | 10/2013 | Hobbs |
| 8,562,598 B2 | 10/2013 | Falkenstein |
| 8,562,599 B2 | 10/2013 | Leyh |
| 8,562,602 B2 | 10/2013 | Azure |
| 8,568,401 B2 | 10/2013 | Brannan |
| 8,568,402 B2 | 10/2013 | Buysse |
| 8,568,404 B2 | 10/2013 | Brannan |
| 8,568,410 B2 | 10/2013 | Vakharia |
| 8,568,411 B2 | 10/2013 | Falkenstein |
| 8,579,894 B2 | 11/2013 | Falkenstein |
| 8,579,897 B2 | 11/2013 | Vakharia |
| 8,579,902 B2 | 11/2013 | Bleich |
| 8,585,704 B2 | 11/2013 | Schmitz |
| 8,603,087 B2 | 12/2013 | Rubinsky |
| 8,608,652 B2 | 12/2013 | Voegele |
| 8,608,739 B2 | 12/2013 | Sartor |
| 8,613,745 B2 | 12/2013 | Bleich |
| 8,617,163 B2 | 12/2013 | Bleich |
| 8,620,423 B2 | 12/2013 | Demarais |
| 8,626,300 B2 | 1/2014 | Demarais |
| 8,632,534 B2 | 1/2014 | Pearson |
| 8,634,929 B2 | 1/2014 | Chornenky |
| 8,647,338 B2 | 2/2014 | Chornenky |
| 8,647,346 B2 | 2/2014 | Bleich |
| 8,652,130 B2 | 2/2014 | Kreindel |
| 8,652,138 B2 | 2/2014 | Bleich |
| 8,652,150 B2 | 2/2014 | Swain |
| 8,663,210 B2 | 3/2014 | Tomasello |
| 8,663,228 B2 | 3/2014 | Schmitz |
| 8,668,688 B2 | 3/2014 | Rusin |
| 8,672,937 B2 | 3/2014 | Decarlo |
| 8,679,003 B2 | 3/2014 | Spivey |
| 8,684,998 B2 | 4/2014 | Demarais |
| 8,702,697 B2 | 4/2014 | Curley |
| 8,706,258 B2 | 4/2014 | Nabors, Sr. |
| 8,712,500 B2 | 4/2014 | Schmidt |
| 8,715,276 B2 | 5/2014 | Thompson |
| 8,721,637 B2 | 5/2014 | Zarins |
| 8,725,249 B2 | 5/2014 | Bar-Yoseph |
| 8,728,137 B2 | 5/2014 | Zarins |
| 8,728,138 B2 | 5/2014 | Zarins |
| 8,728,139 B2 | 5/2014 | Azure |
| 8,731,672 B2 | 5/2014 | Hlavka |
| 8,740,895 B2 | 6/2014 | Mayse |
| 8,740,896 B2 | 6/2014 | Zarins |
| 8,753,335 B2 | 6/2014 | Moshe |
| 8,768,470 B2 | 7/2014 | Deem |
| 8,771,252 B2 | 7/2014 | Gelfand |
| 8,771,260 B2 | 7/2014 | Conlon |
| 8,774,913 B2 | 7/2014 | Demarais |
| 8,774,922 B2 | 7/2014 | Zarins |
| 8,777,943 B2 | 7/2014 | Mayse |
| 8,784,463 B2 | 7/2014 | Zarins |
| 8,797,039 B2 | 8/2014 | Brannan |
| 8,801,626 B2 | 8/2014 | Sun |
| 8,805,545 B2 | 8/2014 | Zarins |
| 8,808,280 B2 | 8/2014 | Mayse |
| 8,814,860 B2 | 8/2014 | Davalos |
| 8,818,514 B2 | 8/2014 | Zarins |
| 8,821,489 B2 | 9/2014 | Mayse |
| 8,828,031 B2 | 9/2014 | Fox |
| 8,835,166 B2 | 9/2014 | Phillips |
| 8,845,559 B2 | 9/2014 | Darlington |
| 8,845,629 B2 | 9/2014 | Demarais |
| 8,845,635 B2 | 9/2014 | Daniel |
| 8,845,639 B2 | 9/2014 | Wallace |
| 8,852,163 B2 | 10/2014 | Deem |
| 8,858,550 B2 | 10/2014 | Busch-Madsen |
| 8,865,076 B2 | 10/2014 | Sarfaty |
| 8,880,185 B2 | 11/2014 | Hastings |
| 8,880,186 B2 | 11/2014 | Levin |
| 8,880,195 B2 | 11/2014 | Azure |
| 8,882,759 B2 | 11/2014 | Manley |
| 8,888,792 B2 | 11/2014 | Harris |
| 8,894,641 B2 | 11/2014 | Brannan |
| 8,903,488 B2 | 12/2014 | Callas |
| 8,906,006 B2 | 12/2014 | Chornenky |
| 8,906,011 B2 | 12/2014 | Gelbart |
| 8,906,035 B2 | 12/2014 | Zwolinski |
| 8,911,439 B2 | 12/2014 | Mayse |
| 8,915,910 B2 | 12/2014 | Falkenstein |
| 8,915,911 B2 | 12/2014 | Azure |
| 8,920,411 B2 | 12/2014 | Gelbart |
| 8,923,970 B2 | 12/2014 | Bar-Yoseph |
| 8,926,606 B2 | 1/2015 | Davalos |
| 8,932,287 B2 | 1/2015 | Gelbart |
| 8,932,289 B2 | 1/2015 | Mayse |
| 8,934,978 B2 | 1/2015 | Deem |
| 8,939,897 B2 | 1/2015 | Nobis |
| 8,939,970 B2 | 1/2015 | Stone |
| 8,945,121 B2 | 2/2015 | Curley |
| 8,948,865 B2 | 2/2015 | Zarins |
| 8,956,350 B2 | 2/2015 | Buysse |
| 8,958,871 B2 | 2/2015 | Demarais |
| 8,958,888 B2 | 2/2015 | Chornenky |
| 8,961,507 B2 | 2/2015 | Mayse |
| 8,961,508 B2 | 2/2015 | Mayse |
| 8,968,542 B2 | 3/2015 | Davalos |
| 8,974,451 B2 | 3/2015 | Smith |
| 8,983,595 B2 | 3/2015 | Levin |
| 8,986,294 B2 | 3/2015 | Demarais |
| 8,992,517 B2 | 3/2015 | Davalos |
| 9,005,189 B2 | 4/2015 | Davalos |
| 9,005,195 B2 | 4/2015 | Mayse |
| 9,005,198 B2 | 4/2015 | Long |
| 9,011,431 B2 | 4/2015 | Long |
| 9,017,323 B2 | 4/2015 | Miller |
| 9,017,324 B2 | 4/2015 | Mayse |
| 9,023,034 B2 | 5/2015 | Jenson |
| 9,023,037 B2 | 5/2015 | Zarins |
| 9,028,483 B2 | 5/2015 | Long |
| 9,028,485 B2 | 5/2015 | Edmunds |
| 9,039,702 B2 | 5/2015 | Miller |
| 9,049,987 B2 | 6/2015 | Conlon |
| 9,050,449 B2 | 6/2015 | Darlington |
| 9,060,761 B2 | 6/2015 | Hastings |
| 9,072,518 B2 | 7/2015 | Swanson |
| 9,072,527 B2 | 7/2015 | Deem |
| 9,078,665 B2 | 7/2015 | Moss |
| 9,084,609 B2 | 7/2015 | Smith |
| 9,089,350 B2 | 7/2015 | Willard |
| 9,101,386 B2 | 8/2015 | Wallace |
| 9,108,040 B2 | 8/2015 | Zarins |
| 9,113,888 B2 | 8/2015 | Orszulak |
| 9,119,633 B2 | 9/2015 | Gelbart |
| 9,119,634 B2 | 9/2015 | Gelbart |
| 9,125,643 B2 | 9/2015 | Hlavka |
| 9,125,661 B2 | 9/2015 | Deem |
| 9,125,666 B2 | 9/2015 | Steinke |
| 9,125,667 B2 | 9/2015 | Stone |
| 9,131,978 B2 | 9/2015 | Zarins |
| 9,138,281 B2 | 9/2015 | Zarins |
| 9,138,287 B2 | 9/2015 | Curley |
| 9,138,288 B2 | 9/2015 | Curley |
| 9,149,328 B2 | 10/2015 | Dimmer |
| 9,149,331 B2 | 10/2015 | Deem |
| 9,155,589 B2 | 10/2015 | Jenson |
| 9,173,704 B2 | 11/2015 | Hobbs |
| 9,186,198 B2 | 11/2015 | Demarais |
| 9,186,209 B2 | 11/2015 | Weber |
| 9,186,213 B2 | 11/2015 | Deem |

(56) References Cited

U.S. PATENT DOCUMENTS

| | | |
|---|---|---|
| 9,192,435 B2 | 11/2015 | Jenson |
| 9,192,715 B2 | 11/2015 | Gelfand |
| 9,192,790 B2 | 11/2015 | Hastings |
| 9,198,733 B2 | 12/2015 | Neal, II |
| 9,220,526 B2 | 12/2015 | Conlon |
| 9,220,558 B2 | 12/2015 | Willard |
| 9,220,561 B2 | 12/2015 | Crow |
| 9,226,772 B2 | 1/2016 | Fox |
| 9,226,790 B2 | 1/2016 | Zemel |
| 9,233,241 B2 | 1/2016 | Long |
| 9,247,952 B2 | 2/2016 | Bleich |
| 9,248,318 B2 | 2/2016 | Darlington |
| 9,254,169 B2 | 2/2016 | Long |
| 9,254,172 B2 | 2/2016 | Behnke, II |
| 9,265,557 B2 | 2/2016 | Sherman |
| 9,265,558 B2 | 2/2016 | Zarins |
| 9,276,367 B2 | 3/2016 | Brannan |
| 9,277,955 B2 | 3/2016 | Herscher |
| 9,277,969 B2 | 3/2016 | Brannan |
| 9,283,051 B2 | 3/2016 | Garcia |
| 9,289,255 B2 | 3/2016 | Deem |
| 9,295,516 B2 | 3/2016 | Pearson |
| 9,307,935 B2 | 4/2016 | Pluta |
| 9,308,039 B2 | 4/2016 | Azure |
| 9,308,043 B2 | 4/2016 | Zarins |
| 9,308,044 B2 | 4/2016 | Zarins |
| 9,314,620 B2 | 4/2016 | Long |
| 9,314,630 B2 | 4/2016 | Levin |
| 9,320,561 B2 | 4/2016 | Zarins |
| 9,320,563 B2 | 4/2016 | Brustad |
| 9,326,751 B2 | 5/2016 | Hastings |
| 9,326,817 B2 | 5/2016 | Zarins |
| 9,327,100 B2 | 5/2016 | Perry |
| 9,327,122 B2 | 5/2016 | Zarins |
| 9,339,618 B2 | 5/2016 | Deem |
| 9,351,790 B2 | 5/2016 | Zemel |
| 9,414,881 B2 | 8/2016 | Callas |
| 9,598,691 B2 | 3/2017 | Davalos |
| 9,764,145 B2 | 9/2017 | Callas |
| 9,867,652 B2 | 1/2018 | Sano |
| 9,943,599 B2 | 4/2018 | Gehl |
| 10,010,666 B2 | 7/2018 | Rubinsky |
| 10,117,701 B2 | 11/2018 | Davalos |
| 10,117,707 B2 | 11/2018 | Garcia |
| 10,143,512 B2 | 12/2018 | Rubinsky |
| 10,154,874 B2 | 12/2018 | Davalos |
| 10,238,447 B2 | 3/2019 | Neal, II |
| 10,245,098 B2 | 4/2019 | Davalos |
| 10,245,105 B2 | 4/2019 | Davalos |
| 10,272,178 B2 | 4/2019 | Davalos |
| 10,286,108 B2 | 5/2019 | Davalos |
| 10,292,755 B2 | 5/2019 | Arena |
| 10,342,600 B2 | 7/2019 | Callas |
| 10,448,989 B2 | 10/2019 | Arena |
| 10,470,822 B2 | 11/2019 | Garcia |
| 10,471,254 B2 | 11/2019 | Sano |
| 10,537,379 B2 | 1/2020 | Sano |
| 10,668,208 B2 | 6/2020 | Rubinsky |
| 10,694,972 B2 | 6/2020 | Davalos |
| 10,702,326 B2 | 7/2020 | Neal, II |
| 10,828,085 B2 | 11/2020 | Davalos |
| 10,828,086 B2 | 11/2020 | Davalos |
| 10,905,492 B2 | 2/2021 | Neal, II |
| 10,959,772 B2 | 3/2021 | Davalos |
| 11,254,926 B2 | 2/2022 | Neal, II |
| 11,272,979 B2 | 3/2022 | Garcia |
| 11,311,329 B2 | 4/2022 | Davalos |
| 11,382,681 B2 | 7/2022 | Arena |
| 11,406,820 B2 | 8/2022 | Sano |
| 11,453,873 B2 | 9/2022 | Davalos |
| 11,607,271 B2 | 3/2023 | Garcia |
| 11,607,537 B2 | 3/2023 | Latouche |
| 2001/0014819 A1 | 8/2001 | Ingle |
| 2001/0039393 A1 | 11/2001 | Mori |
| 2001/0044596 A1 | 11/2001 | Jaafar |
| 2001/0046706 A1 | 11/2001 | Rubinsky |
| 2001/0047167 A1 | 11/2001 | Heggeness |
| 2001/0051366 A1 | 12/2001 | Rubinsky |
| 2002/0002393 A1 | 1/2002 | Mitchell |
| 2002/0010491 A1 | 1/2002 | Schoenbach |
| 2002/0022864 A1 | 2/2002 | Mahvi |
| 2002/0040204 A1 | 4/2002 | Dev |
| 2002/0049370 A1 | 4/2002 | Laufer |
| 2002/0052601 A1 | 5/2002 | Goldberg |
| 2002/0055731 A1 | 5/2002 | Atala |
| 2002/0065541 A1 | 5/2002 | Fredricks |
| 2002/0072742 A1 | 6/2002 | Schaefer |
| 2002/0077314 A1 | 6/2002 | Falk |
| 2002/0077627 A1 | 6/2002 | Johnson |
| 2002/0077676 A1 | 6/2002 | Schroeppel |
| 2002/0082543 A1 | 6/2002 | Park |
| 2002/0091362 A1 | 7/2002 | Maginot |
| 2002/0095197 A1 | 7/2002 | Lardo |
| 2002/0099323 A1 | 7/2002 | Dev |
| 2002/0104318 A1 | 8/2002 | Jaafar |
| 2002/0111615 A1 | 8/2002 | Cosman |
| 2002/0112729 A1 | 8/2002 | Devore |
| 2002/0115208 A1 | 8/2002 | Mitchell |
| 2002/0119437 A1 | 8/2002 | Grooms |
| 2002/0120261 A1 | 8/2002 | Morris |
| 2002/0133324 A1 | 9/2002 | Weaver |
| 2002/0137121 A1 | 9/2002 | Rubinsky |
| 2002/0138075 A1 | 9/2002 | Edwards |
| 2002/0138117 A1 | 9/2002 | Son |
| 2002/0143365 A1 | 10/2002 | Herbst |
| 2002/0147462 A1 | 10/2002 | Mair |
| 2002/0156472 A1 | 10/2002 | Lee |
| 2002/0161361 A1 | 10/2002 | Sherman |
| 2002/0183684 A1 | 12/2002 | Dev |
| 2002/0183735 A1 | 12/2002 | Edwards |
| 2002/0183740 A1 | 12/2002 | Edwards |
| 2002/0188242 A1 | 12/2002 | Wu |
| 2002/0193784 A1 | 12/2002 | McHale |
| 2002/0193831 A1 | 12/2002 | Smith |
| 2003/0009110 A1 | 1/2003 | Tu |
| 2003/0009165 A1 | 1/2003 | Edwards |
| 2003/0014047 A1 | 1/2003 | Woloszko |
| 2003/0016168 A1 | 1/2003 | Jandrell |
| 2003/0055220 A1 | 3/2003 | Legrain |
| 2003/0055420 A1 | 3/2003 | Kadhiresan |
| 2003/0059945 A1 | 3/2003 | Dzekunov |
| 2003/0060856 A1 | 3/2003 | Chornenky |
| 2003/0074039 A1 | 4/2003 | Puskas |
| 2003/0078490 A1 | 4/2003 | Damasco |
| 2003/0088189 A1 | 5/2003 | Tu |
| 2003/0088199 A1 | 5/2003 | Kawaji |
| 2003/0096407 A1 | 5/2003 | Atala |
| 2003/0105454 A1 | 6/2003 | Cucin |
| 2003/0109871 A1 | 6/2003 | Johnson |
| 2003/0127090 A1 | 7/2003 | Gifford |
| 2003/0130711 A1 | 7/2003 | Pearson |
| 2003/0135242 A1 | 7/2003 | Mongeon |
| 2003/0149451 A1 | 8/2003 | Chomenky |
| 2003/0153960 A1 | 8/2003 | Chornenky |
| 2003/0154988 A1 | 8/2003 | Devore |
| 2003/0159700 A1 | 8/2003 | Laufer |
| 2003/0164168 A1 | 9/2003 | Shaw |
| 2003/0166181 A1 | 9/2003 | Rubinsky |
| 2003/0170898 A1 | 9/2003 | Gundersen |
| 2003/0194808 A1 | 10/2003 | Rubinsky |
| 2003/0195385 A1 | 10/2003 | Devore |
| 2003/0195406 A1 | 10/2003 | Jenkins |
| 2003/0199050 A1 | 10/2003 | Mangano |
| 2003/0208200 A1 | 11/2003 | Palanker |
| 2003/0208236 A1 | 11/2003 | Heil |
| 2003/0212394 A1 | 11/2003 | Pearson |
| 2003/0212412 A1 | 11/2003 | Dillard |
| 2003/0225360 A1 | 12/2003 | Eppstein |
| 2003/0228344 A1 | 12/2003 | Fields |
| 2003/0233091 A1 | 12/2003 | Whayne |
| 2004/0009459 A1 | 1/2004 | Anderson |
| 2004/0019371 A1 | 1/2004 | Jaafar |
| 2004/0055606 A1 | 3/2004 | Hendricksen |
| 2004/0059328 A1 | 3/2004 | Daniel |

(56) References Cited

U.S. PATENT DOCUMENTS

| | | |
|---|---|---|
| 2004/0059389 A1 | 3/2004 | Chornenky |
| 2004/0068228 A1 | 4/2004 | Cunningham |
| 2004/0116965 A1 | 6/2004 | Falkenberg |
| 2004/0133194 A1 | 7/2004 | Eum |
| 2004/0138715 A1 | 7/2004 | Van Groeningen |
| 2004/0146877 A1 | 7/2004 | Diss |
| 2004/0153057 A1 | 8/2004 | Davison |
| 2004/0167458 A1 | 8/2004 | Draghia-Akli |
| 2004/0172136 A1 | 9/2004 | Ralph |
| 2004/0176855 A1 | 9/2004 | Badylak |
| 2004/0187875 A1 | 9/2004 | He |
| 2004/0193042 A1 | 9/2004 | Scampini |
| 2004/0193097 A1 | 9/2004 | Hofmann |
| 2004/0199159 A1 | 10/2004 | Lee |
| 2004/0200484 A1 | 10/2004 | Springmeyer |
| 2004/0206349 A1 | 10/2004 | Alferness |
| 2004/0210248 A1 | 10/2004 | Gordon |
| 2004/0230187 A1 | 11/2004 | Lee |
| 2004/0236376 A1 | 11/2004 | Miklavcic |
| 2004/0243107 A1 | 12/2004 | Macoviak |
| 2004/0267189 A1 | 12/2004 | Mavor |
| 2004/0267256 A1 | 12/2004 | Garabedian |
| 2004/0267340 A1 | 12/2004 | Cioanta |
| 2005/0004507 A1 | 1/2005 | Schroeppel |
| 2005/0010209 A1 | 1/2005 | Lee |
| 2005/0010259 A1 | 1/2005 | Gerber |
| 2005/0013726 A1 | 1/2005 | Hill |
| 2005/0013870 A1 | 1/2005 | Freyman |
| 2005/0019830 A1 | 1/2005 | Penner |
| 2005/0020965 A1 | 1/2005 | Rioux |
| 2005/0033276 A1 | 2/2005 | Adachi |
| 2005/0043726 A1 | 2/2005 | McHale |
| 2005/0048651 A1 | 3/2005 | Ryttsen |
| 2005/0049541 A1 | 3/2005 | Behar |
| 2005/0054978 A1 | 3/2005 | Segal |
| 2005/0061322 A1 | 3/2005 | Freitag |
| 2005/0066974 A1 | 3/2005 | Fields |
| 2005/0096537 A1 | 5/2005 | Parel |
| 2005/0096709 A1 | 5/2005 | Skwarek |
| 2005/0107781 A1 | 5/2005 | Ostrovsky |
| 2005/0112141 A1 | 5/2005 | Terman |
| 2005/0135393 A1 | 6/2005 | Benco |
| 2005/0143817 A1 | 6/2005 | Hunter |
| 2005/0165393 A1 | 7/2005 | Eppstein |
| 2005/0171522 A1 | 8/2005 | Christopherson |
| 2005/0171523 A1 | 8/2005 | Rubinsky |
| 2005/0171571 A1 | 8/2005 | Goodin |
| 2005/0171574 A1 | 8/2005 | Rubinsky |
| 2005/0182462 A1 | 8/2005 | Chornenky |
| 2005/0197619 A1 | 9/2005 | Rule |
| 2005/0203489 A1 | 9/2005 | Saadat |
| 2005/0216047 A1 | 9/2005 | Kumoyama |
| 2005/0228373 A1 | 10/2005 | Kelly |
| 2005/0228459 A1 | 10/2005 | Levin |
| 2005/0228460 A1 | 10/2005 | Levin |
| 2005/0234445 A1 | 10/2005 | Conquergood |
| 2005/0234523 A1 | 10/2005 | Levin |
| 2005/0261672 A1 | 11/2005 | Deem |
| 2005/0261707 A1 | 11/2005 | Schatzberger |
| 2005/0267407 A1 | 12/2005 | Goldman |
| 2005/0282284 A1 | 12/2005 | Rubinsky |
| 2005/0283149 A1 | 12/2005 | Thorne |
| 2005/0288684 A1 | 12/2005 | Aronson |
| 2005/0288702 A1 | 12/2005 | McGurk |
| 2005/0288730 A1 | 12/2005 | Deem |
| 2006/0004356 A1 | 1/2006 | Bilski |
| 2006/0004400 A1 | 1/2006 | McGurk |
| 2006/0009748 A1 | 1/2006 | Mathis |
| 2006/0015147 A1 | 1/2006 | Persson |
| 2006/0020347 A1 | 1/2006 | Barrett |
| 2006/0024359 A1 | 2/2006 | Walker |
| 2006/0025760 A1 | 2/2006 | Podhajsky |
| 2006/0025821 A1 | 2/2006 | Gelfand |
| 2006/0030810 A1 | 2/2006 | Mandrusov |
| 2006/0074413 A1 | 4/2006 | Behzadian |
| 2006/0079838 A1 | 4/2006 | Walker |
| 2006/0079845 A1 | 4/2006 | Howard |
| 2006/0079883 A1 | 4/2006 | Elmouelhi |
| 2006/0085054 A1 | 4/2006 | Zikorus |
| 2006/0089635 A1 | 4/2006 | Young |
| 2006/0106379 A1 | 5/2006 | O'Brien |
| 2006/0121610 A1 | 6/2006 | Rubinsky |
| 2006/0127703 A1 | 6/2006 | Takekuma |
| 2006/0142801 A1 | 6/2006 | Demarais |
| 2006/0149123 A1 | 7/2006 | Vidlund |
| 2006/0173490 A1 | 8/2006 | Lafontaine |
| 2006/0182684 A1 | 8/2006 | Beliveau |
| 2006/0184163 A1 | 8/2006 | Breen |
| 2006/0195146 A1 | 8/2006 | Tracey |
| 2006/0206150 A1 | 9/2006 | Demarais |
| 2006/0212032 A1 | 9/2006 | Daniel |
| 2006/0212076 A1 | 9/2006 | Demarais |
| 2006/0212078 A1 | 9/2006 | Demarais |
| 2006/0217702 A1 | 9/2006 | Young |
| 2006/0217703 A1 | 9/2006 | Chornenky |
| 2006/0217704 A1 | 9/2006 | Cockburn |
| 2006/0224188 A1 | 10/2006 | Libbus |
| 2006/0224192 A1 | 10/2006 | Dimmer |
| 2006/0235474 A1 | 10/2006 | Demarais |
| 2006/0241366 A1 | 10/2006 | Falwell |
| 2006/0247619 A1 | 11/2006 | Kaplan |
| 2006/0264752 A1 | 11/2006 | Rubinsky |
| 2006/0264807 A1 | 11/2006 | Westersten |
| 2006/0269531 A1 | 11/2006 | Beebe |
| 2006/0271111 A1 | 11/2006 | Demarais |
| 2006/0276710 A1 | 12/2006 | Krishnan |
| 2006/0278241 A1 | 12/2006 | Ruano |
| 2006/0283462 A1 | 12/2006 | Fields |
| 2006/0293713 A1 | 12/2006 | Rubinsky |
| 2006/0293725 A1 | 12/2006 | Rubinsky |
| 2006/0293730 A1 | 12/2006 | Rubinsky |
| 2006/0293731 A1 | 12/2006 | Rubinsky |
| 2006/0293734 A1 | 12/2006 | Scott |
| 2007/0010805 A1 | 1/2007 | Fedewa |
| 2007/0016183 A1 | 1/2007 | Lee |
| 2007/0016185 A1 | 1/2007 | Tullis |
| 2007/0021803 A1 | 1/2007 | Deem |
| 2007/0025919 A1 | 2/2007 | Deem |
| 2007/0043345 A1 | 2/2007 | Davalos |
| 2007/0055142 A1 | 3/2007 | Webler |
| 2007/0055225 A1 | 3/2007 | Dodd, III |
| 2007/0060989 A1 | 3/2007 | Deem |
| 2007/0066957 A1 | 3/2007 | Demarais |
| 2007/0066971 A1 | 3/2007 | Podhajsky |
| 2007/0078391 A1 | 4/2007 | Wortley |
| 2007/0078453 A1 | 4/2007 | Johnson |
| 2007/0083239 A1 | 4/2007 | Demarais |
| 2007/0088347 A1 | 4/2007 | Young |
| 2007/0093789 A1 | 4/2007 | Smith |
| 2007/0096048 A1 | 5/2007 | Clerc |
| 2007/0118069 A1 | 5/2007 | Persson |
| 2007/0129711 A1 | 6/2007 | Altshuler |
| 2007/0129760 A1 | 6/2007 | Demarais |
| 2007/0137567 A1 | 6/2007 | Shimizu |
| 2007/0151848 A1 | 7/2007 | Novak |
| 2007/0156129 A1 | 7/2007 | Kovalcheck |
| 2007/0156135 A1 | 7/2007 | Rubinsky |
| 2007/0156136 A1 | 7/2007 | Godara |
| 2007/0173899 A1 | 7/2007 | Levin |
| 2007/0179380 A1 | 8/2007 | Grossman |
| 2007/0191589 A1 | 8/2007 | Hirota |
| 2007/0191889 A1 | 8/2007 | Lang |
| 2007/0197895 A1 | 8/2007 | Nycz |
| 2007/0203486 A1 | 8/2007 | Young |
| 2007/0203549 A1 | 8/2007 | Demarais |
| 2007/0230757 A1 | 10/2007 | Trachtenberg |
| 2007/0239099 A1 | 10/2007 | Goldfarb |
| 2007/0244521 A1 | 10/2007 | Bornzin |
| 2007/0249939 A1 | 10/2007 | Gerbi |
| 2007/0282407 A1 | 12/2007 | Demarais |
| 2007/0287950 A1 | 12/2007 | Kjeken |
| 2007/0295336 A1 | 12/2007 | Nelson |
| 2007/0295337 A1 | 12/2007 | Nelson |
| 2008/0015571 A1 | 1/2008 | Rubinsky |

(56) References Cited

U.S. PATENT DOCUMENTS

| | | |
|---|---|---|
| 2008/0015628 A1 | 1/2008 | Dubrul |
| 2008/0015664 A1 | 1/2008 | Podhajsky |
| 2008/0021371 A1 | 1/2008 | Rubinsky |
| 2008/0027314 A1 | 1/2008 | Miyazaki |
| 2008/0027343 A1 | 1/2008 | Fields |
| 2008/0033340 A1 | 2/2008 | Heller |
| 2008/0033417 A1 | 2/2008 | Nields |
| 2008/0045880 A1 | 2/2008 | Kjeken |
| 2008/0052786 A1 | 2/2008 | Lin |
| 2008/0065062 A1 | 3/2008 | Leung |
| 2008/0071262 A1 | 3/2008 | Azure |
| 2008/0071264 A1 | 3/2008 | Azure |
| 2008/0071265 A1 | 3/2008 | Azure |
| 2008/0082145 A1 | 4/2008 | Skwarek |
| 2008/0086115 A1 | 4/2008 | Stoklund |
| 2008/0091135 A1 | 4/2008 | Draghia-Akli |
| 2008/0097139 A1 | 4/2008 | Clerc |
| 2008/0097422 A1 | 4/2008 | Edwards |
| 2008/0103529 A1 | 5/2008 | Schoenbach |
| 2008/0121375 A1 | 5/2008 | Richason |
| 2008/0125772 A1 | 5/2008 | Stone |
| 2008/0125775 A1 | 5/2008 | Morris |
| 2008/0132826 A1 | 6/2008 | Shadduck |
| 2008/0132884 A1 | 6/2008 | Rubinsky |
| 2008/0132885 A1 | 6/2008 | Rubinsky |
| 2008/0140064 A1 | 6/2008 | Vegesna |
| 2008/0146931 A1 | 6/2008 | Zhang |
| 2008/0146934 A1 | 6/2008 | Czygan |
| 2008/0147056 A1 | 6/2008 | Van Der Weide |
| 2008/0154259 A1 | 6/2008 | Gough |
| 2008/0167649 A1 | 7/2008 | Edwards |
| 2008/0171985 A1 | 7/2008 | Karakoca |
| 2008/0190434 A1 | 8/2008 | Tjong Joe Wai |
| 2008/0200911 A1 | 8/2008 | Long |
| 2008/0200912 A1 | 8/2008 | Long |
| 2008/0208052 A1 | 8/2008 | LePivert |
| 2008/0210243 A1 | 9/2008 | Clayton |
| 2008/0213331 A1 | 9/2008 | Gelfand |
| 2008/0214986 A1 | 9/2008 | Ivorra |
| 2008/0224188 A1 | 9/2008 | Han |
| 2008/0234708 A1 | 9/2008 | Houser |
| 2008/0236593 A1 | 10/2008 | Nelson |
| 2008/0249503 A1 | 10/2008 | Fields |
| 2008/0255553 A1 | 10/2008 | Young |
| 2008/0262489 A1 | 10/2008 | Steinke |
| 2008/0269586 A1 | 10/2008 | Rubinsky |
| 2008/0269838 A1 | 10/2008 | Brighton |
| 2008/0275465 A1 | 11/2008 | Paul |
| 2008/0279995 A1 | 11/2008 | Schultheiss |
| 2008/0281319 A1 | 11/2008 | Paul |
| 2008/0283065 A1 | 11/2008 | Chang |
| 2008/0288038 A1 | 11/2008 | Paul |
| 2008/0294155 A1 | 11/2008 | Cronin |
| 2008/0294358 A1 | 11/2008 | Richardson |
| 2008/0300589 A1 | 12/2008 | Paul |
| 2008/0306427 A1 | 12/2008 | Bailey |
| 2008/0312599 A1 | 12/2008 | Rosenberg |
| 2009/0018206 A1 | 1/2009 | Barkan |
| 2009/0018565 A1 | 1/2009 | To |
| 2009/0018566 A1 | 1/2009 | Escudero |
| 2009/0018567 A1 | 1/2009 | Escudero |
| 2009/0024075 A1 | 1/2009 | Schroeppel |
| 2009/0024085 A1 | 1/2009 | To |
| 2009/0029407 A1 | 1/2009 | Gazit |
| 2009/0030336 A1 | 1/2009 | Woo |
| 2009/0036773 A1 | 2/2009 | Lau |
| 2009/0038752 A1 | 2/2009 | Weng |
| 2009/0062788 A1 | 3/2009 | Long |
| 2009/0062792 A1 | 3/2009 | Vakharia |
| 2009/0062795 A1 | 3/2009 | Vakharia |
| 2009/0076496 A1 | 3/2009 | Azure |
| 2009/0076499 A1 | 3/2009 | Azure |
| 2009/0076500 A1 | 3/2009 | Azure |
| 2009/0076502 A1 | 3/2009 | Azure |
| 2009/0081272 A1 | 3/2009 | Clarke |
| 2009/0088636 A1 | 4/2009 | Lau |
| 2009/0099544 A1 | 4/2009 | Munrow |
| 2009/0105703 A1 | 4/2009 | Shadduck |
| 2009/0114226 A1 | 5/2009 | Deem |
| 2009/0118725 A1 | 5/2009 | Auth |
| 2009/0118729 A1 | 5/2009 | Auth |
| 2009/0125009 A1 | 5/2009 | Zikorus |
| 2009/0138014 A1 | 5/2009 | Bonutti |
| 2009/0143705 A1 | 6/2009 | Danek |
| 2009/0157166 A1 | 6/2009 | Singhal |
| 2009/0163904 A1 | 6/2009 | Miller |
| 2009/0171280 A1 | 7/2009 | Samuel |
| 2009/0177111 A1 | 7/2009 | Miller |
| 2009/0186850 A1 | 7/2009 | Kiribayashi |
| 2009/0192508 A1 | 7/2009 | Laufer |
| 2009/0198227 A1 | 8/2009 | Prakash |
| 2009/0198231 A1 | 8/2009 | Esser |
| 2009/0204005 A1 | 8/2009 | Keast |
| 2009/0204112 A1 | 8/2009 | Kleyman |
| 2009/0209955 A1 | 8/2009 | Forster |
| 2009/0216543 A1 | 8/2009 | Pang |
| 2009/0221939 A1 | 9/2009 | Demarais |
| 2009/0228001 A1 | 9/2009 | Pacey |
| 2009/0240247 A1 | 9/2009 | Rioux |
| 2009/0247933 A1 | 10/2009 | Maor |
| 2009/0248012 A1 | 10/2009 | Maor |
| 2009/0269317 A1 | 10/2009 | Davalos |
| 2009/0270756 A1 | 10/2009 | Gamache |
| 2009/0275827 A1 | 11/2009 | Aiken |
| 2009/0281477 A1 | 11/2009 | Mikus |
| 2009/0281540 A1 | 11/2009 | Blomgren |
| 2009/0287081 A1 | 11/2009 | Grossman |
| 2009/0292342 A1 | 11/2009 | Rubinsky |
| 2009/0301480 A1 | 12/2009 | Elsakka |
| 2009/0306544 A1 | 12/2009 | Ng |
| 2009/0306545 A1 | 12/2009 | Elsakka |
| 2009/0318849 A1 | 12/2009 | Hobbs |
| 2009/0318905 A1 | 12/2009 | Bhargav |
| 2009/0326366 A1 | 12/2009 | Krieg |
| 2009/0326436 A1 | 12/2009 | Rubinsky |
| 2009/0326561 A1 | 12/2009 | Carroll, II |
| 2009/0326570 A1 | 12/2009 | Brown |
| 2010/0004623 A1* | 1/2010 | Hamilton, Jr. ...... A61B 18/1492 606/41 |
| 2010/0006441 A1 | 1/2010 | Renaud |
| 2010/0016783 A1 | 1/2010 | Bourke, Jr. |
| 2010/0023004 A1 | 1/2010 | Francischelli |
| 2010/0030211 A1 | 2/2010 | Davalos |
| 2010/0036291 A1 | 2/2010 | Darlington |
| 2010/0049190 A1 | 2/2010 | Long |
| 2010/0056926 A1 | 3/2010 | Deckman |
| 2010/0057074 A1 | 3/2010 | Roman |
| 2010/0057076 A1 | 3/2010 | Behnke |
| 2010/0069921 A1 | 3/2010 | Miller |
| 2010/0079215 A1 | 4/2010 | Brannan |
| 2010/0082022 A1 | 4/2010 | Haley |
| 2010/0082023 A1 | 4/2010 | Brannan |
| 2010/0082024 A1 | 4/2010 | Brannan |
| 2010/0082025 A1 | 4/2010 | Brannan |
| 2010/0082083 A1 | 4/2010 | Brannan |
| 2010/0082084 A1 | 4/2010 | Brannan |
| 2010/0087813 A1 | 4/2010 | Long |
| 2010/0090696 A1 | 4/2010 | Deimling |
| 2010/0100093 A1 | 4/2010 | Azure |
| 2010/0106025 A1 | 4/2010 | Sarfaty |
| 2010/0106047 A1 | 4/2010 | Sarfaty |
| 2010/0121173 A1 | 5/2010 | Sarfaty |
| 2010/0130975 A1 | 5/2010 | Long |
| 2010/0147701 A1 | 6/2010 | Field |
| 2010/0152725 A1 | 6/2010 | Pearson |
| 2010/0160850 A1 | 6/2010 | Ivorra |
| 2010/0168735 A1 | 7/2010 | Deno |
| 2010/0174282 A1 | 7/2010 | Demarais |
| 2010/0179436 A1 | 7/2010 | Sarfaty |
| 2010/0179530 A1 | 7/2010 | Long |
| 2010/0191112 A1 | 7/2010 | Demarais |
| 2010/0191235 A1 | 7/2010 | Moshe |
| 2010/0196984 A1 | 8/2010 | Rubinsky |
| 2010/0204560 A1 | 8/2010 | Salahieh |

(56) References Cited

U.S. PATENT DOCUMENTS

| | | |
|---|---|---|
| 2010/0204638 A1 | 8/2010 | Hobbs |
| 2010/0211061 A1 | 8/2010 | Leyh |
| 2010/0222677 A1 | 9/2010 | Placek |
| 2010/0228234 A1 | 9/2010 | Hyde |
| 2010/0228247 A1 | 9/2010 | Paul |
| 2010/0241117 A1 | 9/2010 | Paul |
| 2010/0249771 A1 | 9/2010 | Pearson |
| 2010/0250209 A1 | 9/2010 | Pearson |
| 2010/0255795 A1 | 10/2010 | Rubinsky |
| 2010/0256624 A1 | 10/2010 | Brannan |
| 2010/0256628 A1 | 10/2010 | Pearson |
| 2010/0256630 A1 | 10/2010 | Hamilton, Jr. |
| 2010/0261994 A1 | 10/2010 | Davalos |
| 2010/0262067 A1 | 10/2010 | Chornenky |
| 2010/0268223 A1 | 10/2010 | Coe |
| 2010/0268225 A1 | 10/2010 | Coe |
| 2010/0286690 A1 | 11/2010 | Paul |
| 2010/0292686 A1 | 11/2010 | Rick |
| 2010/0298822 A1 | 11/2010 | Behnke |
| 2010/0298823 A1 | 11/2010 | Cao |
| 2010/0298825 A1 | 11/2010 | Slizynski |
| 2010/0331758 A1 | 12/2010 | Davalos |
| 2010/0331911 A1 | 12/2010 | Kovalcheck |
| 2011/0009860 A1 | 1/2011 | Chornenky |
| 2011/0015630 A1 | 1/2011 | Azure |
| 2011/0017207 A1 | 1/2011 | Hendricksen |
| 2011/0021970 A1 | 1/2011 | Vo-Dinh |
| 2011/0034209 A1 | 2/2011 | Rubinsky |
| 2011/0054458 A1 | 3/2011 | Behnke |
| 2011/0064671 A1 | 3/2011 | Bynoe |
| 2011/0082362 A1 | 4/2011 | Schmidt |
| 2011/0082414 A1 | 4/2011 | Wallace |
| 2011/0092973 A1 | 4/2011 | Nuccitelli |
| 2011/0098695 A1 | 4/2011 | Brannan |
| 2011/0105823 A1 | 5/2011 | Single, Jr. |
| 2011/0106221 A1 | 5/2011 | Neal, II |
| 2011/0112434 A1 | 5/2011 | Ghabrial |
| 2011/0112531 A1 | 5/2011 | Landis |
| 2011/0118721 A1 | 5/2011 | Brannan |
| 2011/0118727 A1 | 5/2011 | Fish |
| 2011/0118729 A1 | 5/2011 | Heeren |
| 2011/0118732 A1 | 5/2011 | Rubinsky |
| 2011/0118734 A1 | 5/2011 | Auld |
| 2011/0130834 A1 | 6/2011 | Wilson |
| 2011/0135626 A1 | 6/2011 | Kovalcheck |
| 2011/0144524 A1 | 6/2011 | Fish |
| 2011/0144562 A1 | 6/2011 | Heeren |
| 2011/0144635 A1 | 6/2011 | Harper |
| 2011/0144638 A1 | 6/2011 | Heeren |
| 2011/0144641 A1 | 6/2011 | Dimalanta, Jr. |
| 2011/0144657 A1 | 6/2011 | Fish |
| 2011/0152678 A1 | 6/2011 | Aljuri |
| 2011/0152906 A1 | 6/2011 | Escudero |
| 2011/0152907 A1 | 6/2011 | Escudero |
| 2011/0160514 A1* | 6/2011 | Long ............... A61B 18/1477 606/41 |
| 2011/0166499 A1 | 7/2011 | Demarais |
| 2011/0172659 A1 | 7/2011 | Brannan |
| 2011/0176037 A1 | 7/2011 | Benkley, III |
| 2011/0178570 A1 | 7/2011 | Demarais |
| 2011/0202052 A1 | 8/2011 | Gelbart |
| 2011/0202053 A1 | 8/2011 | Moss |
| 2011/0207758 A1 | 8/2011 | Sobotka |
| 2011/0208096 A1 | 8/2011 | Demarais |
| 2011/0208180 A1 | 8/2011 | Brannan |
| 2011/0217730 A1 | 9/2011 | Gazit |
| 2011/0230874 A1 | 9/2011 | Epstein |
| 2011/0245756 A1 | 10/2011 | Arora |
| 2011/0251607 A1 | 10/2011 | Kruecker |
| 2011/0282354 A1 | 11/2011 | Schulte |
| 2011/0288545 A1 | 11/2011 | Beebe |
| 2011/0301587 A1 | 12/2011 | Deem |
| 2011/0306971 A1 | 12/2011 | Long |
| 2012/0034131 A1 | 2/2012 | Rubinsky |
| 2012/0046658 A1 | 2/2012 | Kreindel |
| 2012/0059255 A1 | 3/2012 | Paul |
| 2012/0071870 A1 | 3/2012 | Salahieh |
| 2012/0071872 A1 | 3/2012 | Rubinsky |
| 2012/0071874 A1 | 3/2012 | Davalos |
| 2012/0085649 A1 | 4/2012 | Sano |
| 2012/0089009 A1 | 4/2012 | Omary |
| 2012/0090646 A1 | 4/2012 | Tanaka |
| 2012/0095459 A1 | 4/2012 | Callas |
| 2012/0101538 A1 | 4/2012 | Ballakur |
| 2012/0109122 A1 | 5/2012 | Arena |
| 2012/0130289 A1 | 5/2012 | Demarais |
| 2012/0150172 A1 | 6/2012 | Ortiz |
| 2012/0165813 A1 | 6/2012 | Lee |
| 2012/0179091 A1 | 7/2012 | Ivorra |
| 2012/0220999 A1 | 8/2012 | Long |
| 2012/0226218 A1 | 9/2012 | Phillips |
| 2012/0226271 A1 | 9/2012 | Callas |
| 2012/0265186 A1 | 10/2012 | Burger |
| 2012/0277741 A1 | 11/2012 | Davalos |
| 2012/0303012 A1 | 11/2012 | Leyh |
| 2012/0303020 A1 | 11/2012 | Chornenky |
| 2012/0310236 A1 | 12/2012 | Placek |
| 2012/0310237 A1 | 12/2012 | Swanson |
| 2013/0030239 A1 | 1/2013 | Weyh |
| 2013/0030430 A1 | 1/2013 | Stewart |
| 2013/0035921 A1 | 2/2013 | Rodriguez-Ponce |
| 2013/0041436 A1 | 2/2013 | Ruse |
| 2013/0072858 A1 | 3/2013 | Watson |
| 2013/0090646 A1 | 4/2013 | Moss |
| 2013/0108667 A1 | 5/2013 | Soikum |
| 2013/0110106 A1 | 5/2013 | Richardson |
| 2013/0184702 A1 | 7/2013 | Neal, II |
| 2013/0196441 A1 | 8/2013 | Rubinsky |
| 2013/0197425 A1 | 8/2013 | Golberg |
| 2013/0202766 A1 | 8/2013 | Rubinsky |
| 2013/0218157 A1 | 8/2013 | Callas |
| 2013/0230895 A1 | 9/2013 | Koblizek |
| 2013/0238062 A1 | 9/2013 | Ron Edoute |
| 2013/0253415 A1 | 9/2013 | Sano |
| 2013/0261389 A1 | 10/2013 | Long |
| 2013/0281968 A1 | 10/2013 | Davalos |
| 2013/0296679 A1 | 11/2013 | Condie |
| 2013/0345697 A1 | 12/2013 | Garcia |
| 2013/0345779 A1 | 12/2013 | Maor |
| 2014/0005664 A1 | 1/2014 | Govari |
| 2014/0017218 A1 | 1/2014 | Scott |
| 2014/0039489 A1 | 2/2014 | Davalos |
| 2014/0046322 A1 | 2/2014 | Callas |
| 2014/0052118 A1 | 2/2014 | Laske |
| 2014/0066913 A1 | 3/2014 | Sherman |
| 2014/0081255 A1 | 3/2014 | Johnson |
| 2014/0088578 A1 | 3/2014 | Rubinsky |
| 2014/0094792 A1 | 4/2014 | Sharonov |
| 2014/0094793 A1 | 4/2014 | Sharonov |
| 2014/0107643 A1 | 4/2014 | Chornenky |
| 2014/0111224 A1 | 4/2014 | Agate |
| 2014/0121663 A1 | 5/2014 | Pearson |
| 2014/0121728 A1 | 5/2014 | Dhillon |
| 2014/0163551 A1 | 6/2014 | Maor |
| 2014/0207133 A1 | 7/2014 | Model |
| 2014/0296844 A1 | 10/2014 | Kevin |
| 2014/0309579 A1 | 10/2014 | Rubinsky |
| 2014/0378964 A1 | 12/2014 | Pearson |
| 2015/0025526 A1 | 1/2015 | Hua |
| 2015/0032105 A1 | 1/2015 | Azure |
| 2015/0066013 A1 | 3/2015 | Salahieh |
| 2015/0066020 A1 | 3/2015 | Epstein |
| 2015/0088120 A1 | 3/2015 | Garcia |
| 2015/0088220 A1 | 3/2015 | Callas |
| 2015/0112333 A1 | 4/2015 | Chorenky |
| 2015/0126922 A1 | 5/2015 | Willis |
| 2015/0141984 A1 | 5/2015 | Loomas |
| 2015/0152504 A1 | 6/2015 | Lin |
| 2015/0164584 A1 | 6/2015 | Davalos |
| 2015/0173824 A1 | 6/2015 | Davalos |
| 2015/0196351 A1 | 7/2015 | Stone |
| 2015/0201996 A1 | 7/2015 | Rubinsky |
| 2015/0265349 A1 | 9/2015 | Moss |
| 2015/0289923 A1 | 10/2015 | Davalos |

(56) References Cited

U.S. PATENT DOCUMENTS

| | | |
|---|---|---|
| 2015/0320478 A1 | 11/2015 | Cosman, Jr. |
| 2015/0320481 A1 | 11/2015 | Cosman, Jr. |
| 2015/0320488 A1 | 11/2015 | Moshe |
| 2015/0320999 A1 | 11/2015 | Nuccitelli |
| 2015/0327944 A1 | 11/2015 | Neal, II |
| 2016/0022957 A1 | 1/2016 | Hobbs |
| 2016/0066977 A1 | 3/2016 | Neal, II |
| 2016/0074114 A1 | 3/2016 | Pearson |
| 2016/0113708 A1 | 4/2016 | Moss |
| 2016/0143698 A1 | 5/2016 | Garcia |
| 2016/0235470 A1 | 8/2016 | Callas |
| 2016/0287313 A1 | 10/2016 | Rubinsky |
| 2016/0287314 A1 | 10/2016 | Arena |
| 2016/0338758 A9 | 11/2016 | Davalos |
| 2016/0338761 A1 | 11/2016 | Chornenky |
| 2016/0354142 A1 | 12/2016 | Pearson |
| 2016/0367310 A1 | 12/2016 | Onik |
| 2017/0035501 A1 | 2/2017 | Chornenky |
| 2017/0065339 A1 | 3/2017 | Mickelsen |
| 2017/0137512 A1 | 5/2017 | Van Hoorick |
| 2017/0189579 A1 | 7/2017 | Davalos |
| 2017/0209620 A1 | 7/2017 | Davalos |
| 2017/0266438 A1 | 9/2017 | Sano |
| 2017/0319851 A1 | 11/2017 | Athos |
| 2017/0348525 A1 | 12/2017 | Sano |
| 2017/0360326 A1 | 12/2017 | Davalos |
| 2018/0071014 A1 | 3/2018 | Neal |
| 2018/0125565 A1 | 5/2018 | Sano |
| 2018/0161086 A1 | 6/2018 | Davalos |
| 2018/0198218 A1 | 7/2018 | Regan |
| 2019/0029749 A1 | 1/2019 | Garcia |
| 2019/0046255 A1 | 2/2019 | Davalos |
| 2019/0069945 A1 | 3/2019 | Davalos |
| 2019/0076528 A1 | 3/2019 | Soden |
| 2019/0083169 A1 | 3/2019 | Single |
| 2019/0133671 A1 | 5/2019 | Davalos |
| 2019/0175248 A1 | 6/2019 | Neal, II |
| 2019/0175260 A1 | 6/2019 | Davalos |
| 2019/0223938 A1 | 7/2019 | Arena |
| 2019/0232048 A1 | 8/2019 | Latouche |
| 2019/0233809 A1 | 8/2019 | Neal, II |
| 2019/0256839 A1 | 8/2019 | Neal, II |
| 2019/0282294 A1 | 9/2019 | Davalos |
| 2019/0328445 A1 | 10/2019 | Sano |
| 2019/0351224 A1 | 11/2019 | Sano |
| 2019/0376055 A1 | 12/2019 | Davalos |
| 2020/0046432 A1 | 2/2020 | Garcia |
| 2020/0046967 A1 | 2/2020 | Ivey |
| 2020/0093541 A9 | 3/2020 | Neal et al. |
| 2020/0197073 A1 | 6/2020 | Sano |
| 2020/0260987 A1 | 8/2020 | Davalos |
| 2020/0289188 A1 | 9/2020 | Forsyth |
| 2020/0323576 A1 | 10/2020 | Neal |
| 2020/0405373 A1 | 12/2020 | O'Brien |
| 2021/0022795 A1 | 1/2021 | Davalos |
| 2021/0023362 A1 | 1/2021 | Lorenzo |
| 2021/0052882 A1 | 2/2021 | Wasson |
| 2021/0113265 A1 | 4/2021 | D'Agostino |
| 2021/0137410 A1 | 5/2021 | O'Brien |
| 2021/0186600 A1 | 6/2021 | Davalos |
| 2021/0361341 A1 | 11/2021 | Neal, II |
| 2021/0393312 A1 | 12/2021 | Davalos |
| 2022/0151688 A1 | 5/2022 | Garcia |
| 2022/0161027 A1 | 5/2022 | Aycock |
| 2022/0290183 A1 | 9/2022 | Davalos |
| 2022/0362549 A1 | 11/2022 | Sano |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| AU | 2012255070 | 1/2014 |
| AU | 2015259303 A1 | 11/2016 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| CN | 112807074 A | 5/2021 |
| DE | 863111 | 1/1953 |
| DE | 4000893 A1 | 7/1991 |
| DE | 60038026 T2 | 2/2009 |
| EP | 0218275 A1 | 4/1987 |
| EP | 0339501 A2 | 11/1989 |
| EP | 10378132 A2 | 7/1990 |
| EP | 0528891 A1 | 3/1993 |
| EP | 0528891 B1 | 3/1993 |
| EP | 0533511 A1 | 3/1993 |
| EP | 0908156 | 4/1999 |
| EP | 0935482 A1 | 8/1999 |
| EP | 0998235 A1 | 5/2000 |
| EP | 1011495 A1 | 6/2000 |
| EP | 1061983 A1 | 12/2000 |
| EP | 1061983 B1 | 12/2000 |
| EP | 1196550 A2 | 4/2002 |
| EP | 1207797 A1 | 5/2002 |
| EP | 1344497 | 9/2003 |
| EP | 1406685 A1 | 4/2004 |
| EP | 1406685 B1 | 4/2004 |
| EP | 1424970 A2 | 6/2004 |
| EP | 1424970 B1 | 6/2004 |
| EP | 1439792 A1 | 7/2004 |
| EP | 1442765 A1 | 8/2004 |
| EP | 1462065 A2 | 9/2004 |
| EP | 1493397 A1 | 1/2005 |
| EP | 1506039 A1 | 2/2005 |
| EP | 1011495 B1 | 11/2005 |
| EP | 1791485 B1 | 6/2007 |
| EP | 1796568 A1 | 6/2007 |
| EP | 1207797 B1 | 2/2008 |
| EP | 1962708 B1 | 9/2008 |
| EP | 1962710 B1 | 9/2008 |
| EP | 1962945 B1 | 9/2008 |
| EP | 2280741 A1 | 2/2011 |
| EP | 2373241 B1 | 10/2011 |
| EP | 2381829 A1 | 11/2011 |
| EP | 2413833 A1 | 2/2012 |
| EP | 2429435 | 3/2012 |
| EP | 2488251 A2 | 8/2012 |
| EP | 2593179 | 5/2013 |
| EP | 2627274 | 8/2013 |
| EP | 2642937 A2 | 10/2013 |
| EP | 2651505 | 10/2013 |
| EP | 3143124 A1 | 3/2017 |
| EP | 3852868 A1 | 7/2021 |
| ES | 2300272 T3 | 6/2008 |
| ES | 2315493 | 4/2009 |
| JP | H10243947 A | 9/1998 |
| JP | 2001510702 A | 8/2001 |
| JP | 2002360712 A | 12/2002 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2007516792 | 6/2007 |
| JP | 2008508946 A | 3/2008 |

(56) References Cited

FOREIGN PATENT DOCUMENTS

| | | |
|---|---|---|
| JP | 4252316 B2 | 4/2009 |
| JP | 200951850 A | 5/2009 |
| JP | 2009518130 A | 5/2009 |
| JP | 2009518151 A | 5/2009 |
| JP | 2009532077 A | 9/2009 |
| JP | 2010503496 A | 2/2010 |
| JP | 2010511467 A | 4/2010 |
| JP | 2011137025 A | 7/2011 |
| JP | 2012510332 A | 5/2012 |
| JP | 2012515018 A | 7/2012 |
| JP | 2012521863 A | 9/2012 |
| JP | 201450157 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 A | 4/2004 |
| WO | 9104014 A1 | 4/1991 |
| WO | 9614238 | 5/1996 |
| WO | 9634571 A1 | 11/1996 |
| WO | 9639531 A1 | 12/1996 |
| WO | 9810745 A1 | 3/1998 |
| WO | 9814238 A1 | 4/1998 |
| WO | 9901076 A1 | 1/1999 |
| WO | 9904710 A1 | 2/1999 |
| WO | 0020554 A1 | 4/2000 |
| WO | 0107583 A1 | 2/2001 |
| WO | 0107584 A1 | 2/2001 |
| WO | 0107585 A1 | 2/2001 |
| WO | 0110319 A1 | 2/2001 |
| WO | 2001048153 A1 | 7/2001 |
| WO | 0170114 A1 | 9/2001 |
| WO | 0181533 A1 | 11/2001 |
| WO | 0200554 A1 | 1/2002 |
| WO | 02078527 A2 | 10/2002 |
| WO | 02089686 A1 | 11/2002 |
| WO | 02100459 A2 | 12/2002 |
| WO | 2003020144 A1 | 3/2003 |
| WO | 2003047684 A2 | 6/2003 |
| WO | 03099382 A1 | 12/2003 |
| WO | 2004008153 | 1/2004 |
| WO | 2004037341 A2 | 5/2004 |
| WO | 2004080347 A2 | 9/2004 |
| WO | 2005065284 A2 | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2007137303 A2 | 11/2007 |
| WO | 2008034103 A3 | 3/2008 |
| WO | 2008063195 A1 | 5/2008 |
| WO | 2008101086 A2 | 8/2008 |
| WO | 2008101091 A2 | 8/2008 |
| WO | 200903468 A1 | 3/2009 |
| WO | 2009046176 A1 | 4/2009 |
| WO | 2009134876 A1 | 11/2009 |
| WO | 2009135070 A1 | 11/2009 |
| WO | 2009137800 A2 | 11/2009 |
| WO | 2010015592 | 2/2010 |
| WO | 2010064154 A1 | 6/2010 |
| WO | 2010080974 A1 | 7/2010 |
| WO | 2010085765 | 7/2010 |
| WO | 2010117806 A1 | 10/2010 |
| WO | 2010118387 A | 10/2010 |
| WO | 2010128373 | 11/2010 |
| WO | 2010132472 A1 | 11/2010 |
| WO | 2010151277 A1 | 12/2010 |
| WO | 2011028937 | 3/2011 |
| WO | 2011047387 A2 | 4/2011 |
| WO | 2011062653 A1 | 5/2011 |
| WO | 2011072221 A1 | 6/2011 |
| WO | 2011135294 A1 | 11/2011 |
| WO | 2012006533 A1 | 1/2012 |
| WO | 2012051433 A2 | 4/2012 |
| WO | 2012054560 A1 | 4/2012 |
| WO | 2012054573 A2 | 4/2012 |
| WO | 2012063266 | 5/2012 |
| WO | 2012071526 A2 | 5/2012 |
| WO | 2012088149 A2 | 6/2012 |
| WO | 2012140376 | 10/2012 |
| WO | 2013052138 | 4/2013 |
| WO | 2013176881 | 11/2013 |
| WO | 2014039320 | 3/2014 |
| WO | 2015175570 A1 | 11/2015 |
| WO | 2015192027 A1 | 12/2015 |
| WO | 2016100325 A1 | 6/2016 |
| WO | 2016164930 A1 | 10/2016 |
| WO | 2017024123 A1 | 2/2017 |
| WO | 2017117418 A1 | 7/2017 |
| WO | 2020061192 A1 | 3/2020 |
| WO | 2022066768 A1 | 3/2022 |

OTHER PUBLICATIONS

Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.

Griffiths, et al., A Dual-Frequency Electrical Impedance Tomography System, Phys. Med. Biol., 1989, vol. 34, No. 10, pp. 1465-1476.

Griffiths, The Importance of Phase Measurement in Electrical Impedance Tomography, Phys. Med. Biol., 1987, vol. 32, No. 11, pp. 1435-1444.

Griffiths, Tissue spectroscopy with electrical impedance tomography: Computer simulations, IEEE Transactions on Biomedical Engineering, Sep. 1995, vol. 42, No. 9, pp. 948-954.

Groen, M. H. A. et al., "In Vivo Analysis of the Origin and Characteristics of Gaseous Microemboli during Catheter-Mediated Irreversible Electroporation," Europace, 2021, 23(1), 139-146.

Guenther, E. et al., "Electrical breakdown in tissue electroporation," Biochem. Biophys. Res. Commun., vol. 467, No. 4, 736-741, Nov. 2015, 15 pages.

Gumerov, et al., The Dipole Approximation Method and Its Coupling with the Regular Boundary Element Method for Efficient Electrical Impedance Tomography, Boundary Element Technology XIII, 1999, 10 pp.

Guo, et al., Irreversible electroporation in the liver: Contrast-enhanced inversion-recovery MR imaging approaches to differentiate reversibly electroporated penumbra from irreversibly electroporated ablation zones, Radiology, Feb. 2011, vol. 258, No. 2, pp. 461-468.

Hall, et al, Nanosecond pulsed electric fields have differential effects on cells in the S-phase, DNA and Cell Biology, 2007, vol. 26, No. 3, pp. 160-171.

Hall, et al, Nanosecond pulsed electric fields induce apoptosis in p53-wildtype and p53-null HCT116 colon carcinoma cells, Apoptosis, May 23, 2007, 12, pp. 1721-1731.

Hapala, Breaking the Barrier: Methods for Reversible Permeabilization of Cellular Membranes, Critical Reviews in Biotechnology, 17(2): 105-122, 1997.

He, et al, Nonlinear current response of micro electroporation and resealing dynamics for human cancer cells, Bioelectrochemistry, Jan. 29, 2008, 72, pp. 161-168.

Helczynska et al., "Hypoxia promotes a dedifferentiated phenotype in ductal breast carcinoma in situ." Cancer Research, vol. 63, pp. 1441-1444 (2003).

Heller, et al., Clinical Applications of Electrochemotherapy, Advanced Drug Delivery Reviews, vol. 35, pp. 119-129, 1999.

Hjouj, et al, MRI study on reversible and irreversible electroporation induced blood brain barrier disruption, Aug. 10, 2012, Plos One, vol. 7, 8, e42817, pp. 1-9.

(56) References Cited

OTHER PUBLICATIONS

Hjouj, M., et al., "Electroporation-Induced BBB Disruption and Tissue Damage Depicted by MRI", Neuro-Oncology 13: issue suppl 3, abstract ET-32 (2011).
Hjouj, M., et al., "MRI Study on Reversible and Irreversible Electroporation Induced Blood Brain Barrier Disruption", PLOS One, Aug. 2012, 7:8, e42817.
Ho, et al., Electroporation of Cell Membranes: A Review, Critical Reviews in Biotechnology, 16(4): 349-362, 1996.
Hoejholt, K. L. et al. Calcium electroporation and electrochemotherapy for cancer treatment: Importance of cell Tiembrane composition investigated by lipidomics, calorimetry and in vitro efficacy. Scientific Reports (Mar. 18, 2019) 3:4758, p. 1-12.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.
Hong, et al., Cardiac ablation via electroporation, 31st Annual International Conference of the IEEE EMBS, IEEE, Sep. 2, 2009, pp. 3381-3384.
Hu, Q., et al., "Simulations of transient membrane behavior in cells subjected to a high-intensity ultrashort electric pulse", Physical Review E, 71(3) (2005).
Huang, et al., Micro-Electroporation: Improving the Efficiency and Understanding of Electrical Permeabilization of cells, Biomedical Microdevices, vol. 2, pp. 145-150,1999.
Hughes, et al., An analysis of studies comparing electrical impedance tomography with x-ray videofluoroscopy in the assessment of swallowing, Physiol. Meas. 1994, 15, pp. A199-A209.
Ibey et al., "Selective cytotoxicity of intense nanosecond-duration electric pulses in mammalian cells." Biochimica Et Biophysica Acta-General Subjects, vol. 1800, pp. 1210-1219 (2010).
International Application No. PCT/US2009/042100, International Search Report dated Jul. 9, 2009, 5 pages.
International Search Report 06751655_SESR dated Oct. 16, 2009.
International Search Report 07716249_SESR dated Jan. 19, 2009.
International Search Report 09739678_SESR dated May 3, 2012.
International Search Report 12002108_EPS dated May 30, 2012.
International Search Report 12002108.4 ESO dated Jun. 12, 2013.
International Search Report for 06751655 SESR dated Oct. 9, 2016.
International Search Report for 06751655.9 ESO dated Oct. 29, 2009.
International Search Report for 10824248.8 ESO dated Jan. 20, 2014.
International Search Report for 11833421 SESR dated Mar. 18, 2014.
International Search Report for IPRP, PCT/US2006/01645, dated Oct. 30, 2007, 5 pages.
International Search Report for PCT-US-10-053077 ISR dated Aug. 2, 2011.
International Search Report for PCT-US-10-053077 WOSA dated Aug. 2, 2011.
International Search Report for PCT/US06/16045 ISR dated Sep. 25, 2007, 1 page.
International Search Report for PCT/US2006/016045 IPRP dated Oct. 30, 2007.
International Search Report for PCT/US2007/000084 IPRP dated Jul. 8, 2008, 8 pages.
International Search Report for PCT/US2009/038661 IPRP dated Sep. 28, 2010.
International Search Report for PCT/US2009/042100 IPRP dated Nov. 2, 2010.
International Search Report for PCT/US2009/042100 WOSA dated Jul. 9, 2009.
International Search Report for PCT/US2009/047969 IPRP dated Dec. 21, 2010.
International Search Report for PCT/US2009/047969 ISR dated Jan. 21, 2010.
International Search Report for PCT/US2009/047969 WOSA dated Jan. 21, 2010.
International Search Report for PCT/US2009/048270 IPRP dated Jan. 5, 2011.
International Search Report for PCT/US2009/048270 ISR dated Feb. 11, 2010.
"TUNA—Suggested Local Anesthesia Guidelines." Published by VidaMed, Inc. (1 page) (2001).
Abiror, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).
Adeyanju, et al., The improvement of irreversible electroporation therapy using saline-irrigated electrodes: A theoretical study, Technology in Cancer Research and Treatment, Aug. 2011, vol. 10, No. 4, pp. 347-360.
Agerholm-Larsen, et al, Preclinical validation of electrochemotherapy as an effective treatment for brain tumors, Cancer Res, Jun. 1, 2011, 71, 11, pp. 3753-3762.
Al-Khadra, et al, The role of electroporation in defibrillation, Circulation Research, Oct. 27, 2000, 87, pp. 797-804.
Al-Sakere et al., "Tumor ablation with irreversible electroporation." PLoS One, Issue 11, e1135, 8 pages, 2007.
Al-Sakere, et al, A study of the immunological response to tumor ablation with irreversible electroporation, Technology in Cancer Research and Treatment, Aug. 2007, vol. 6, No. 4, pp. 301-305.
Albright, et al, Performance and complications associated with the Synchromed 10-ml infusion pump for intrathecal baclofen administration in children, J Neurosurg (Pediatrics 2), Aug. 2004, vol. 101, pp. 64-68.
Alinezhadbalalami, N. et al., "Generation of Tumor-activated T cells Using Electroporation", Bioelectrochemistry 142 (2021) 107886, Jul. 13, 2021, 11 pages.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cuit. Meth., 15:56-62, 1993.
Appelbaum, L., et al., "US Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle Contraction." Biomed. Eng. Online, vol. 10, 20 pages (2011).
Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.
Arena, C.B., et al., "A three-dimensional in vitro tumor platform for modeling therapeutic irreversible electroporation." Biophysical Journal, 2012.103(9): p. 2033-2042.
Arena, Christopher B., et al., "Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Arena, et al., Theoretical considerations of tissue electropration with high frequency biopolar pulses, IEEEE, pp. 1-7, (2010).
Arena, et al, Towards the development of latent heat storage electrodes for electroporation-based therapies, Applied Physics Letters, 2012, 101, 083902, pp. 1-4.
Asami et al., "Dielectric properties of Aouse lyAphocytes and erythrocytes." BiochiAica et Biophysica Acta (BBA)—Molecular Cell Research, 1010 (1989) pp. 49-55.
B0lland, F., et al., "Development and characterisation of a full-thickness acellular porcine bladder matrix for tissue engineering", Biomaterials, Elsevier Science Publishers, Barking, GB, vol. 28, No. 6,Nov. 28, 2006, pp. 1061-1070.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.

(56) References Cited

OTHER PUBLICATIONS

Ball, et al, Irreversible electroporation: A new challenge in "out of the operating theater" anesthesia, Anesth Analg, May 2010, 110, pp. 1305-1309.

Bancroft, et al, Design of a Flow Perfusion Bioreactor SysteA for Bone Tissue-Engineering Applications, Tissue Engineering, vol. 9, No. 3, 2003, p. 549-554.

Baptista et al., "The Use of Whole Organ Decellularization for the Generation of a Vascularized Liver Organoid," Heptatology, vol. 53, No. 2, pp. 604-617 (2011).

Barber, Electrical Impedance Tomography Applied Potential Tomography, Advances in Biomedical Engineering, Beneken and Thevenin, eds., IOS Press, pp. 165-173, 1993.

Bayazitoglu, et al, An overview of nanoparticle assisted laser therapy, International Journal of Heat and Mass Transfer, Sep. 11, 2013, 67, pp. 469-486.

Beebe, S.J., et al., "Diverse effects of nanosecond pulsed electric fields on cells and tissues", DNA and Cell Biology, 22(12): 785-796(2003).

Beebe, S.J., et al., Nanosecond pulsed electric field (nsPEF) effects on cells and tissues: apoptosis induction andt umor growth inhibition. PPPS-2001 Pulsed Power Plasma Science 2001,28th IEEE International Conference on plasma Science and 13th IEEE International Pulsed Power Conference, Digest of Technical Papers (Cat. No.01CH37251). IEEE, Part vol. 1, 2001, pp. 211-215, vol. I, Piscataway, NJ, USA.

Beebe, S.J., et al., "Nanosecond, high-intensity pulsed electric fields induce apoptosis in human cells", FASEB J, 17 (9): p. 1493-1495 (2003).

Beitel-White, N., S. Bhonsle, R. Martin, and R. V. Davalos, "Electrical characterization of human biological tissue or irreversible electroporation treatments," in 2018 40th Annual International Conference of the IEEE Engineering in Medicine and Biology Society (EMBC). IEEE, 2018, pp. 4170-4173.

Belehradek, J., et al., "Electropermeabilization of Cells in Tissues Assessed by the Qualitative and Quantitative Electroloading of Bleomycin", Biochimica Et Biophysica Acta-Biomembranes, 1190(1): p. 155-163 (1994).

Ben-David, E. et al., "Irreversible Electroporation: Treatment Effect Is Susceptible to Local Environment and Tissue Properties," Radiology, vol. 269, No. 3,2013, 738-747.

Ben-David, E., et al., "Characterization of Irreversible Electroporation Ablation in In Vivo Procine Liver" Am. J. Roentgenol. 198(1), W62-W68 (2012).

Benz, R., et al. "Reversible electrical breakdown of lipid bilayer membranes: a charge-pulse relaxation study". J Membr Biol, 48(2): p. 181-204 (1979).

Bertacchini, et al, Design of an irreversible electroporation system for clinical use, Technology in Cancer Research and Treatment, Aug. 2007, vol. 6, No. 4, pp. 313-320.

Bhonsle, S. et al., "Characterization of Irreversible Electroporation Ablation with a Validated Perfused Organ Model," J. Vase. Interv. Radiol., vol. 27, No. 12, pp. 1913-1922.e2, 2016.

Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.

Bhonsle, S., M. F. Lorenzo, A. Safaai-Jazi, and R. V. Davalos, "Characterization of nonlinearity and dispersion in issue impedance during high-frequency electroporation," IEEE Transactions on Biomedical Engineering, vol. 65, No. 10, pp. 2190-2201, 2018.

Blad, et al., Impedance Spectra of Tumour Tissue in Comparison with Normal Tissue; a Possible Clinical Application for Electrical Impedance Tomography, Physiol. Meas. 17 (1996) A105-A115.

Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.

Boone, et al., Review imaging with electricity: Report of the European concerted action on impedance tomography, Journal of Medical Engineering & Technology, Nov. 1997, vol. 21, No. 6, pp. 201-232.

Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.

Bower et al., "Irreversible electroporation of the pancreas: definitive local therapy without systemic effects." Journal of surgical oncology, 2011.104(1): p. 22-28.

Bown, S.G., Phototherapy of tumors. World J. Surgery, 1983. 7: p. 700-709.

BPH Management Strategies: Improving Patient Satisfaction, Urology Times, May 2001, vol. 29, Supplement 1.

Brown, et al., Blood Flow Imaging Using Electrical Impedance Tomography, Clin. Phys. Physiol. Meas., 1992, vol. 13, Suppl. A, 175-179.

Buist et al., "Efficacy of multi-electrode linear irreversible electroporation," Europace, vol. 23, No. 3, pp. 464-468, 2021, 5 pages.

Bulvik, B. E. et al. "Irreversible Electroporation versus Radiofrequency Ablation: A Comparison of Local and Systemic Effects in a Small Animal Model," Radiology, vol. 280, No. 2, 2016,413-424.

Maybody, An Overview of Image-Guided Percutaneous Ablation of Renal Tumors, Seminars in Interventional Radiology/vol. 27, No. 3, 2010, pp. 261-267.

Mazurek, et al, Effect of Short HV Pulses in Bacteria and Fungi, 1995, vol. 2, No. 3, pp. 418-425.

McCall, Nanoknife, liposomal doxorubicin show efficacy against liver cancer, European Congress of Radiology, Mar. 1, 2011, pp. 1-2.

McCarley, and Soulen, Percutaneous ablation of hepatic tumors, Seminars in Interventional Radiology, 2010, vol. 27, No. 3, pp. 255-260.

McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.

McNeal, D. R., "Analysis of a Model for Excitation of Myelinated Nerve," IEEE Trans. Biomed. Eng., vol. BME-23, No. 4 329-337, 1976, 9 pages.

McWilliams, et al, Image-guided tumor ablation: Emerging technologies and future directions, Seminars in Interventional Radiology, 2010, vol. 27, No. 3, pp. 302-313.

Mercadal, B. et al., "Avoiding nerve stimulation in irreversible electroporation: A numerical modeling study," Phys. Med. Biol., vol. 62, No. 20, 8060-8079, 2017, 28 pages.

Miklavcic, D. et al., "The effect of high frequency electric pulses on muscle contractions and antitumor efficiency in vivo for a potential use in clinical electrochemotherapy," Bioelectrochemistry, vol. 65, 121-128, 2004, 8 pages.

Miklavcic, et al., The Importance of Electric Field Distribution for Effective in Vivo Electroporation of Tissues, Biophysical Journal, vol. 74, May 1998, pp. 2152-2158.

Miller, L., et al., Cancer cells ablation with irreversible electroporation, Technology in Cancer Research and Treatment 4 (2005) 699-706.

Min, M., A. Giannitsis, R. Land, B. Cahill, U. Pliquett, T. Nacke, D. Frense, G. Gastrock, and D. Beckmann, Comparison of rectangular wave excitations in broad band impedance spectroscopy for microfluidic applications, in World Congress on Medical Physics and Biomedical Engineering, Sep. 7-12, 2009, Munich, Germany. Springer, 2009, pp. 85-88.

Min, M., U. Pliquett, T. Nacke, A. Barthel, P. Annus, and R. Land, "Broadband excitation for short-time impedance spectroscopy," Physiological measurement, vol. 29, No. 6, p. S185,2008.

Mir et al., "Mechanisms of Electrochemotherapy" Advanced Drug Delivery Reviews 35:107-118 (1999).

Mir et al., British Journal of Cancer, 77(12):2336-2342 (1998).

Mir, Chapter 1 application of electroporation gene therapy: Past, current and future, Electroporation Protocols: Preclinical and Clinical Gene Medicine, Methods in Molecular Biology, vol. 423, 2008, pp. 3-17.

(56) References Cited

OTHER PUBLICATIONS

Mir, et al., Effective Treatment of Cutaneous and Subcutaneous Malignant Tumours by Electrochemotherapy, British Journal of Cancer, vol. 77, No. 12, pp. 2336-2342, 1998.

Mir, et al., Electrochemotherapy Potentiation of Antitumour Effect of Bleomycin by Local Electric Pulses, European Journal of Cancer, vol. 27, No. 1, pp. 68-72, 1991.

Mir, et al., Electrochemotherapy, a Novel Antitumor Treatment: First Clinical Trial, C.R. Acad. Sci. Paris, Ser. III, vol. 313, pp. 613-618, 1991.

Mir, L.M. and Orlowski, S., "The basis of electrochemotherapy," Electrochemotherapy, Electrogenetherapy, and Transdermal Drug Delivery: Electrically Mediated Delivery of Molecules to Cells, M.J. Jaroszeski, R. Heller, R. Gilbert, Editors, Humana Press, Totowa, New Jersey p. 99-118 (2000).

Mir, L.M., et al., Electric Pulse-Mediated Gene Delivery to Various Animal Tissues, in Advances in Genetics, 'Academic Press, 2005, p. 83-114.

Mir, Orlowski, Introduction: Electropermeabilization as a new drug delivery approach, Methods in Molecular Medicine, 2000, vol. 37, pp. 99-117.

Mir, Therapeutic Perspectives of In Vivo Cell Electropermeabilization, Bioelectrochemistry, vol. 53, pp. 1-10, 2000.

Miklavcic, et al., A Validated Model of an in Vivo Electric Field Distribution in Tissues for Electrochemotherapy and For DNA Electrotransfer for Gene Therapy, Biochimica et Biophysica Acta 1523 (2000), pp. 73-83.

Mulhall et al., "Cancer, pre-cancer and normal oral cells distinguished by dielectrophoresis." Analytical and Bioanalytical Chemistry, vol. 401, pp. 2455-2463 (2011).

Narayan, et al., Establishment and Characterization of a Human Primary Prostatic Adenocarcinoma Cell Line (ND-1), The Journal of Urology, vol. 148, 1600-1604, Nov. 1992.

Naslund, Cost-effectiveness of minimally invasive treatments and transurethral resection (TURP) in benign prostatic hyperplasia (BPH), Unveristy of Maryland School of Medicine, 2001, pp. 1213.

Naslund, Michael J., Transurethral Needle Ablation of the Prostate, Urology, vol. 50, No. 2, Aug. 1997.

Neal II, et al., Experimental characterization and numerical modeling of tissue electrical conductivity during pulsed electric fields for irreversible electroporation treatment planning, IEEE Transactions on Biomedical Engineering, Apr. 2012, vol. 59, No. 4, pp. 1076-1085.

Neal II, et al, Successful treatment of a large soft tissue sarcoma with irreversible electroporaiton, Journal of Clinical Oncology, May 1, 2011, vol. 29, No. 13, pp. e372-e377.

Neal II, R. E et al. In Vitro and Numerical Support for Combinatorial Irreversible Electroporation and Electrochemotherapy Glioma Treatment. Annals of Biomedical Engineering, Oct. 29, 2013,13 pages.

Neal II, R.E., et al., "Treatment of breast cancer through the application of irreversible electroporation using a novel minimally invasive single needle electrode." Breast Cancer Research and Treatment, 2010. 123(1): p. 295-301.

Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.

Neal RE II, et al. (2013) Improved Local and Systemic Anti-Tumor Efficacy for Irreversible Electroporation in immunocompetent versus Immunodeficient Mice. PLoS One 8(5): e64559. https://doi.org/10.1371/journal.Done.0064559.

Neal, Davalos, The feasibility of irreversible electroporation for the treatment of breast cancer and other heterogeneous systems, Annals of Biomedical Engineering, Dec. 2009, vol. 37, No. 12, pp. 2615-2625.

Neal, et al., A study using irreversible electroporation to treat large, irregular tumors in a canine patient, 32nd Annual International Conference of the IEEE EMBS, IEEE, Aug. 2010, pp. 2747-2750.

Neal, et al., An "Off-the-Shelf" system for intraprocedural electrical current evaluation and monitoring of irreversible electroporation therapy, Cardiovasc Intervent Radiol, Feb. 27, 2014.

Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).

Neu, and Neu, Mechanism of irreversible electroporation in cells: Insight from the models, Irreversible Electroporation: BioMed, pp. 85-122.

Neumann, et al., Gene Transfer into Mouse Lyoma Cells by Electroporation in High Electric Fields, J. Embo., vol. 1, No. 7, pp. 841-845, 1982.

Neumann, et al., Permeability Changes Induced by Electric Impulses in Vesicular Membranes, J. Membrane Biol., vol. 10, pp. 279-290, 1972.

Neven et al., Epicardial Linear Electroporation Ablation and Lesion Size, Department of Cardiology, University of Medical Utrecht, Aug. 2014, vol. 11, No. 8.

Nikolova, B., et al., "Treatment of Melanoma by Electroporation of Bacillus Calmette-Guerin". Biotechnology & Biotechnological Equipment, 25(3): p. 2522-2524 (2011).

Nikolski, et al., Electroporation of the heart, Europace, 2005, 7, pp. S146-S154.

Nuccitelli, R., et al., "A new pulsed electric field therapy for melanoma disrupts the tumor's blood supply and causes complete remission without recurrence", Int J Cancer, 125(2): p. 438-445 (2009).

O'Brien, T. J. et al., "Effects of internal electrode cooling on irreversible electroporation using a perfused organ Model," Int. J. Hyperth., vol. 35, No. 1, pp. 44-55, 2018.

O'Brien et al., "Investigation of the Alamar Blue (resazurin) fluorescent dye for the assessment of mammalian cell cytotoxicity." European Journal of Biochemistry, vol. 267, pp. 5421-5426 (2000).

Ohio Environmental Protection Agency, Ground Water Flow and Fate and Transport Modeling, State of Ohio Environmental Protection Agency, 2007, pp. 14-1-14-32.

Okino, et al., Effects of High-Voltage Electrical Impulse and an Anticancer Drug on In Vivo Growing Tumors, Japanese Journal of Cancer Research, vol. 78, pp. 1319-1321, 1987.

Onik, and Rubinsky, Irreversible electroporation: First patient experience focal therapy of prostate cancer, Irreversible Electroporation, BioMed, pp. 235-247.

Dupuy, and Shulman, Current status of thermal ablation treatments for lung malignancies, Seminars in Interventional Radiology, 2010, vol. 27, No. 3, pp. 268-275.

Dupuy, et al, Irreversible electroporation in a swine lung model, Cardiovasc Intervent Radiol, Dec. 30, 2010, 34, pp. 391-395.

Duraiswami, et al., Boundary Element Techniques for Efficient 2-D and 3-D Electrical Impedance Tomography, Chemical Engineering Science, vol. 52, No. 13, pp. 2185-2196, 1997.

Duraiswami, et al., Efficient 2D and 3D Electrical Impedance Tomography Using Dual Reciprocity Boundary Element Techniques, Engineering Analysis with Boundary Elements 22, (1998) 13-31.

Duraiswami, et al., Solution of Electrical Impedance Tomography Equations Using Boundary Element Methods, Boundary Element Technology XII, 1997, pp. 226-237.

Edd et al., "Mathematical modeling of irreversible electroporation for treatment planning." Technology in Cancer Research and Treatment, vol. 6, No. 4, pp. 275-286 (2007).

Edd, et al, In vivo results of a new focal tissue ablation technique: Irreversible electroporation, IEEE Transactions on Biomedical Engineering, Jun. 2006, vol. 53, No. 5, pp. 1409-1415.

Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).

Eppich et al., "Pulsed electric fields for selection of hematopoietic cells and depletion of tumor cell contaminants." Nature Biotechnology 18, pp. 882-887 (2000).

(56) References Cited

OTHER PUBLICATIONS

Erez, et al., Controlled Destruction and Temperature Distributions in Biological Tissues Subjected to Monoactive Electrocoagulation, Transactions of the ASME: Journal of Mechanical Design, vol. 102, Feb. 1980, pp. 42-49.
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
European Search Report for the European Patent Application No. 16777511, dated Dec. 4, 2018, 1 page.
Extended European Search Report for the European Patent Application No. EP16777511, dated Mar. 20, 2019, 4 pages.
Faroja, et al, Irreversible electroporation ablation: Is all the damage nonthermal?, Radiology, Feb. 2013, vol. 266, No. 2, pp. 462-470.
Fischbach, et al, Engineering tumors with 3D scaffolds, Nature Methods, Sep. 2, 2007, vol. 4, No. 10, pp. 855-860.
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997, 9 pages.
Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41,2012.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Garcia et al., "Irreversible electroporation (IRE) to treat brain cancer." ASME Summer Bioengineering Conference, Marco Island, FL, Jun. 25-29, 2008, 2 pages.
Garcia P.A., et al., "7.0-T Magnetic Resonance Imaging Characterization of Acute Blood-Brain-Barrier Disruption Achieved with Intracranial Irreversible Electroporation", PLOS One, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia-Sanchez, T., A. Azan, I. Leray, J. Rosell-Ferrer, R. Bragos, and L. M. Mir, "Interpulse multifrequency electrical impedance measurements during electroporation of adherent differentiated myotubes," Bioelectrochemistry, vol. 105, pp. 123-135, 2015.
Garcia, et al, A parametric study delineating irreversible electroporation from thermal damage based on a minimally invasive intracranial procedure, Biomedical Engineering Online, 2011, 10: 34, pp. 1-21.
Garcia, et al, Irreversible electroporation (IRE) to treat brain tumors, Proceedings of the ASME 2008 Summer Bioengineering Conference (SBC2008), Jun. 25, 2008, pp. 6-7.
Garcia, et al, Non-thermal irreversible electroporation (N-TIRE) and adjuvant fractionated radiotherapeutic multimodal therapy for intracranial malignant glioma in a canine patient, Feb. 2011, vol. 10, No. 1, pp. 73-83.
Garcia, et al, Non-thermal irreversible electroporation for deep intracranial disorders, 32nd Annual International Conference of the IEEE EMBS, IEEE, Aug. 2010, pp. 2747463.
Garcia, et al, Position paper concerning the use of Angiodynamics' nanoknife system for treatment of brain gliomas, Virgina Tech—Wake Forest University, May 22, 2013, pp. 1-46.
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., Intracranial Nonthermal Irreversible Electroporation: In Vivo Analysis. Journal of Membrane Biology, 2010. 236(1): p. 127-136.
Garcia, P.A., R.V. Davalos, and D. Miklavcic, A Numerical Investigation of the Electric and Thermal Cell Kill Distributions in Electroporation-Based Therapies in Tissue. Plos One, 2014. 9(8).
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010,22 pages.
Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).
Gauger, et al., A Study of Dielectric Membrane Breakdown in the Fucus Egg, J. Membrane Biol., vol. 48, No. 3, pp. 249-264, 1979.
Gawad, S., T. Sun, N. G. Green, and H. Morgan, "Impedance spectroscopy using maximum length sequences: Application to single cell analysis," Review of Scientific Instruments, vol. 78, No. 5, p. 054301,2007.
Gehl, et al., In Vivo Electroporation of Skeletal Muscle: Threshold, Efficacy and Relation to Electric Field Distribution, Biochimica et Biphysica Acta 1428, 1999, pp. 233-240.
Gencer, et al., Electrical Impedance Tomography: Induced-Current Imaging Achieved with a Multiple Coil System, IEEE Transactions on Biomedical Engineering, vol. 43, No. 2, Feb. 1996, pp. 139-149.
Gilbert, et al., Novel Electrode Designs for Electrochemotherapy, Biochimica et Biophysica Acta 1334, 1997, pp. 3-14.
Gilbert, et al., The Use of Ultrasound Imaging for Monitoring Cryosurgery, Proceedings 6th Annual Conference, IEEE Engineering in Medicine and Biology, 107-111,1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa, et al., Dielectric spectroscopy of single human erythrocytes at physiological ionic strength: Dispersion of the cytoplasm, Biophysical Journal, Jul. 1996, vol. 71, pp. 495-506.
Glidewell, et al., The Use of Magnetic Resonance Imaging Data and the Inclusion of Anisotropic Regions in Electrical Impedance Tomography, Biomed. Sci. Instrum. 1993; 29: 251-7.
Golberg, A. and Rubinsky, B., "A statistical model for multidimensional irreversible electroporation cell death in tissue." Biomed Eng Online, 9,13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar et al., An Approach to electrical modeling of single and multiple cells, Mar. 18, 2003, PNAS, vol. 100 No. 6, pp. 3203-3208.
International Search Report for PCT/US2009/048270 WOSA dated Feb. 11, 2010.
International Search Report for PCT/US2009/062806 WOSA dated Jan. 19, 2010.
International Search Report for PCT/US2010/022011 IPRP dated Jul. 26, 2011.
International Search Report for PCT/US2010/022011 ISR dated Aug. 30, 2010.
International Search Report for PCT/US2010/022011 WOSA dated Aug. 30, 2010.
International Search Report for PCT/US2010/029243 IPRP dated Oct. 4, 2011.
International Search Report for PCT/US2010/029243 WOSA dated Jul. 30, 2010.

(56) References Cited

OTHER PUBLICATIONS

International Search Report for PCT/US2010/036734 IPRP dated Nov. 29, 2011.
International Search Report for PCT/US2010/036734 IRO dated Dec. 23, 2010.
International Search Report for PCT/US2010/036734 WOSA dated Dec. 23, 2010.
International Search Report for PCT/US2010/053077 IPRP dated Apr. 17, 2012.
International Search Report for PCT/US2011/024909 IPRP dated Aug. 21, 2012.
International Search Report for PCT/US2011/024909 ISR dated Oct. 18, 2011.
International Search Report for PCT/US2011/024909 WOSA dated Oct. 18, 2011.
International Search Report for PCT/US2011/025003 IPRP dated Aug. 21, 2012.
International Search Report for PCT/US2011/025003 ISR dated Oct. 24, 2011. 10 pages.
International Search Report for PCT/US2011/025003 WOSA dated Oct. 24, 2011.
International Search Report for PCT/US2011/056177 ESO dated Mar. 28, 2014.
International Search Report for PCT/US2011/056177 IPRP dated Apr. 16, 2013.
International Search Report for PCT/US2011/056177 ISR dated May 30, 2012.
International Search Report for PCT/US2011/056177 WOSA dated May 30, 2012.
International Search Report for PCT/US2011/062067 IPRP dated May 28, 2013.
International Search Report for PCT/US2011/062067 ISR dated Jul. 25, 2012.
International Search Report for PCT/US2011/062067 WOSA dated Jul. 25, 2012.
International Search Report PCT-US-07-000084 ISR dated Dec. 14, 2007, 2 pages.
International Search Report PCT/US07/00084 WOSA dated Dec. 14, 2007, 7 pages.
International Search Report PCT/US2009/038661 ISR dated Jun. 12, 2009.
International Search Report PCT/US2009042100 ESO dated May 11, 2012.
Issa, et al, Recent Reports: The TUNA procedure for BPH: Review of the technology, Infections in Urology, Jul. 1998, 8 pages.
Issa, et al, Specialty Surgery: The TUNA procedure for BPH: Basic procedure and clinical results, Infections in Urology, Sep. 1998, 6 pages.
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998, pp. 1-16.
Ivanusa, et al., MRI Macromolecular Contrast Agents as Indicators of Changed Tumor Blood Flow, Radiol. Oncol. 2001; 35(2): 139-47.
Ivey, J_ W., E. L. Latouche, M. B. Sano, J_ H. Rossmeisl, R. V. Davalos, and S. S. Verbridge, "Targeted cellular ablation based on the morphology of malignant cells," Sci. Rep., vol. 5, pp. 1-17, 2015.
Ivorra et al., "In vivo electric impedance measurements during and after electroporation of rat live." Bioelectrochemistry, vol. 70, pp. 287-295 (2007).
Ivorra, Bioimpedance monitoring for physicians: an overview, Biomedical Applications Group, Centre Nacional de Microelectronica, Jul. 2003, pp. 1-35.
Ivorra, et al, In vivo electrical conductivity measurements during and after tumor electroporation: conductivity changes reflect the treatment outcome,Phys. Med. Biol., Sep. 17, 2009, 54, pp. 5949-5963.
Ivorra, et al., Impedance analyzer for in vivo electroporation studies, Proceedings of the 28th IEEE EMBS Annual International Conference, IEEE, Aug. 30, 2006, pp. 5056-5059.
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8:16, 9 Pages 2008).
Jiang, et al, Membrane-targeting approaches for enhanced cancer cell destruction with irreversible electroporation, Annuals of Biomedical Engineering, Aug. 15, 2013.
Jordan, D.W., et al., "Effect of pulsed, high-power radiofrequency radiation on electroporation of mammalian cells", Ieee Transactions on Plasma Science, 32(4): p. 1573-1578 (2004).
Jossinet et al., Electrical Impedance Endo-Tomography: Imaging Tissue From Inside, IEEE Transactions on Medical Imaging, vol. 21, No. 6, Jun. 2002, pp. 560-565.
Kanduser, et al, Cell membrane fluidity related to electroporation and resealing, Eur Biophys J, Oct. 8, 2006, 35, pp. 196-204.
Katsuki, S., et al., "Biological effects of narrow band pulsed electric fields", Ieee Transactions on Dielectrics and Electrical Insulation,. 14(3): p. 663-668 (2007).
Kingham et al., "Ablation of perivascular hepatic malignant tumors with irreversible electroporation." Journal of the American College of Surgeons, 2012. 215(3), p. 379-387.
Kinosita et al., "Electroporation of cell membrane visualized under a pulsed-laser fluorescence microscope." Biophysical Journal, vol. 53, pp. 1015-1019 (1988).
Kinosita et al., "Voltage-induced pore formation and hemolysis of human erythrocytes." Biochimica et Biophysica Acta (BBA)—Biomembranes, 471 (1977) pp. 227-242.
Kinosita, et al., Hemolysis of Human Erythrocytes by a Transient Electric Field, Proc. Natl. Acad. Sci. USA, vol. 74, No. 5, pp. 1923-1927, 1977.
Kinosita, Jr., et al., Formation and resealing of pores of controlled sizes in human erythrocyte membrane, Aug. 1977, vol. 268, pp. 438-441.
Butikofer, R. et al., "Electrocutaneous Nerve Stimulation-I: Model and Experiment," IEEE Trans. Biomed. Eng., vol. BME-25, No. 6, 526-531, 1978,6 pages.
Butikofer, R. et al., "Electrocutaneous Nerve Stimulation-II: Stimulus Waveform Selection," IEEE Trans. Biomed. Eng., vol. BME-26, No. 2, 69-75, 1979.
Cannon et al., "Safety and early efficacy of irreversible electroporation for hepatic tumors in proximity to vital structures." Journal of Surgical Oncology, 6 pages (2012).
Carmi, and Georgiades, Combination percutaneous and intraarterial therapy for the treatment of hepatocellular carcinoma: A review, Seminars in Interventional Radiology, 2010, vol. 27, No. 3, pp. 296-301.
Carpenter A.E. et al., "CellProfiler: image analysis software for identifying and quantifying cell phenotypes." Genome Biol. 2006; 7(10): R100. Published online Oct. 31, 2006,11 pages.
Carson, et al, Improving patient satisfaction, BPH management strategies, Supplement to Urology Times, May 2001, Vo. 29, Suppl. 1, pp. 1-22.
Castellvi, Q., B. Mercadal, and A. Ivorra, "Assessment of electroporation by electrical impedance methods," in Handbook of electroporation. Springer-Verlag, 2016, pp. 671-690.
Cemazar, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year rollow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652(1989).
Charpentier, et al., Irreversible electroporation of the liver an dliver hilum in swine, HBP, 2011, 13, pp. 168-173.

(56) References Cited

OTHER PUBLICATIONS

Charpentier, K.P., et al., "Irreversible electroporation of the pancreas in swine: a pilot study." HPB: the official journal of the International Hepato Pancreato Biliary Association, 2010.12(5): p. 348-351.

Chen et al., "Classification of cell types using a microfluidic device for mechanical and electrical measurement on single cells." Lab on a Chip, vol. 11, pp. 3174-3181 (2011).

Chen, et al, Preclinical study of locoregional therapy of hepatocellular carcinoma by bioelectric ablation with microsecond pulsed electric fields (usPEFs), Scientific Reports, Apr. 2015, 5, 9851, pp. 1-10.

Chen, M.T., et al., "Two-dimensional nanosecond electric field mapping based on cell electropermeabilization", PMC Biophys, 2(1):9 (2009).

Choi, et al, Preclinical analysis of irreversible electroporation on rat liver tissues using a microfabricated electroporator, Tissue Engineering Part C, 2010, vol. 16, No. 6, pp. 1245-1253.

Clark et al., "The electrical properties of resting and secreting pancreas." The Journal of Physiology, vol. 189, pp. 247-260 (1967).

Coates, et al., The electric discharge of the electric eel, Electrophorus electricus (Linnaeus), Zoologica: New York Zoological Society, Apr. 5, 1937, pp. 1-32.

Cook, et al, ACT3: a high-speed, high-precision electrical impedance tomograph, IEEE Transactions on Biomedical Engineering, 1994, vol. 41, No. 8, pp. 713-722.

Corovic, et al, Analytical and numerical quantification and comparison of the local electric field in the tissue for different electrode configurations, BioMedical Engineering Online, Oct. 15, 2007, 6, 37, pp. 1-14.

Cosman, E. R. et al., "Electric and Thermal Field Effects in Tissue Around Radiofrequency Electrodes," Pain Med., vol. 6, No. 6, 405-424, 2005, 20 pages.

Cowley, Good News for Boomers, Newsweek, Dec. 30, 1996/Jan. 6, 1997, p. 1.

Cox, et al., Surgical Treatment of Atrial Fibrillation: A Review, Europace (2004) 5, S20-S29.

Craiu, Scadden, Chapter 22 flow electroporation with pulsed electric fields for purging tumor cells, Electroporation Protocols: Preclinical and Clinical Gene Medicine, Methods in Molecular Biology, vol. 423, 2008, pp. 301-310.

Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.

Crowley, Electrical Breakdown of Biomolecular Lipid Membranes as an Electromechanical Instability, Biophysical Journal, vol. 13, pp. 711-724, 1973.

Cukjati, et al., Real time electroporation control for accurate and safe in vivo non-viral gene therapy, Bioelectrochemistry, Nov. 10, 2006, 70, pp. 501-507.

Dahl et al., "Nuclear shape, mechanics, and mechanotransduction." Circulation Research vol. 102, pp. 1307-1318 (2008).

Daniels, Rubinsky, Electrical field and temperature model of nonthermal irreversible electroporation in heterogeneous tissues, Journal of Biomedical Engineering, Jul. 2009, vol. 131, 071006, pp. 1-12.

Daniels, Rubinsky, Temperature modulation of electric fields in biological matter, PLOS One, vol. 6, Iss. 6, e20877, pp. 1-9, Jun. 2011.

Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).

Daud, et al, Phase I trial of Interleukin-12 plasmid electroporation in patients with metastatic melanoma, Journal of clinical Oncology, Dec. 20, 2008, vol. 26, No. 36, pp. 5896-5903.

Davalos et al., "Electrical impedance tomography for imaging tissue electroporation," IEEE Transactions on Biomedical Engineering, 51, pp. 761-767, 2004.

Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002, pp. 400-403.

Davalos, et al., Theoretical Analysis of the Thermal Effects During In Vivo Tissue Electroporation, Bioelectrochemistry, vol. 61, pp. 99-107, 2003.

Davalos, et al., Tissue Ablation with Irreversible Electroporation, Annals of Biomedical Engineering, vol. 33, No. 2, p. 223-231, Feb. 2005.

Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).

Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002, pp. 1-237.

De Senneville, B. D. et al., "MR thermometry for monitoring tumor ablation," European radiology, vol. 17, No. 9, pp. 2401-2410, 2007.

De Vuyst, E., et al., "In situ bipolar Electroporation for localized cell loading with reporter dyes and investigating gap functional coupling", Biophysical Journal, 94(2): p. 469-479 (2008).

Dean, Nonviral Gene Transfer to Skeletal, Smooth, and Cardiac Muscle in Living Animals, Am J. Physiol Cell Physiol 289: 233-245, 2005.

Demirbas, M. F., "Thermal Energy Storage and Phase Change Materials: An Overview" Energy Sources Part B 1(1), 35-95 (2006).

Deodhar, et al., Irreversible electroporation near the heart: Ventricular arrhythmias can be prevented with ECG synchronization, AJR, Mar. 2011, 196, pp. W330-W335.

Deodhar, et al., Renal tissue ablation with irreversible electroporation: Preliminary results in a porcine model, Technology and Engineering, Urology, 2010, 1-7.

Dev, et al, Electric field of a six-needle array electrode used in drug and DNA delivery in vivo: Analytical versus numerical solution, IEEE Transactions on Biomedical Engineering, Nov. 2003, vol. 50, No. 11, pp. 1296-1300.

Dev, et al., Medical Applications of Electroporation, IEEE Transactions of Plasma Science, vol. 28, No. 1, pp. 206-223, Feb. 2000.

Dev, et al, Sustained Local Delivery of Heparin to the Rabbit Arterial Wall with an Electroporation Catheter, Catheterization and Cardiovascular Diagnosis, Nov. 1998, vol. 45, No. 3, pp. 337-343.

Diederich, et al, Catheter-based ultrasound applicators for selective thermal ablation: progress towards MRI-guided applications in prostate, Int. J. Hyperthermia, Nov. 2004, vol. 20, No. 7, pp. 739-756.

Du Pre, et al, Minimal coronary artery damage by myocardial electroporation ablation, European Society of Cardiology, Europace, May 31, 2012, pp. 1-6.

Dunki-Jacobs, et al., Evaluation of resistance as a measure of successful tumor ablation during irreversible electroporation of the pancreas, American College of Surgeons, Feb. 2014, vol. 218, No. 2, pp. 179-187.

Teissie, J. and T.Y. Tsong, "Electric-Field Induced Transient Pores in Phospholipid-Bilayer Vesicles". Biochemistry, 20(6): p. 1548-1554(1981).

Tekle, et al., "Electroporation by using bipolar oscillating electric field: An improved method for DNA transfection of NIF 3T3 cells," Proc. Natl. Acad. Sci., Biochemistry, vol. 88, pp. 4230-4234, May 1991.

Thompson, et al., To determine whether the temperature of 2% lignocaine gel affects the initial discomfort which may be associated with its instillation into the male urethra, BJU International (1999), 84, 1035-1037.

Thomson, Human experience with irreversible electroporation, Irreversible Electroporation, BioMed, 2010, pp. 249-354.

Thomson, K. R., et al., "Investigation of the Safety of Irreversible Electroporation in Humans" J. Vascular Int. Radiol. 22 (5), 611-621 (2011).

Tibbitt et al., "Hydrogels as Extracellular Matrix Mimics for 3D Cell Culture", Jul. 2009, Biotechnol Bioeng, 103 (4),655-663.

(56) References Cited

OTHER PUBLICATIONS

Tijink, et al., How we do it: Chemo-electroporation in the head and neck for otherwise untreatable patients, Correspondence, Clinical Otolaryngology, 2006, 31, pp. 447-451.

Tracy, et al, Irreversible electroporation (IRE): A novel method for renal tissue ablation, BJU International, 107, pp. 1982-1987.

Trimmer, et al, Minimally invasive percutaneous treatment of small renal tumors with irreversible electroporation: a single-center experience, J Vasc Intery Radiol, 2015, 26: pp. 1465-1471.

Troszak, et al., Self-powered electroporation using a singularity-induced nano-electroporation configuration, Biochemical and Biophysical Research Communications, Sep. 28, 2011, 414, pp. 419-424.

Tsivian, Polascik, Recent advances in focal therapy of prostate and kidney cancer, Medicine Reports, Jan. 18, 2010, 2, 1, pp. 1-3.

Valdez, C. M. et al., "The interphase interval within a bipolar nanosecond electric pulse modulates bipolar cancellation," Bioelectromagnetics, vol. 39, No. 6, 441-450, 2018, 28 pages.

Van Den Bos, W. et al., "MRI and contrast-enhanced ultrasound imaging for evaluation offocal irreversible electroporation treatment: results from a phase i-ii study in patients undergoing ire followed by radical prostatectomy," European radiology, vol. 26, No. 7, pp. 2252-2260, 2016.

Verbridge et al., "Oxygen-Controlled Three-Dimensional Cultures to Analyze Tumor Angiogenesis." Tissue Engineering, Part A vol. 16, pp. 2133-2141 (2010).

Verma, A. et al., "Primer on Pulsed Electrical Field Ablation: Understanding the Benefits and Limitations," Circ. Arrhythmia Electrophysiol., No. September, pp. 1-16,2021,16 pages.

Vernier, P.T., et al., "Nanoelectropulse-driven membrane perturbation and small molecule permeabilization", Bmc Cell Biology, 7 (2006).

Vidamed, Inc., "Highlights from Worldwide Clinical Studies: Transurethral Needle Ablation (TUNA)," Vidamed's Office TUNA System, (4 pages) (2001).

Vizintin, A. et al., "Effect of interphase and interpulse delay in high-frequency irreversible electroporation pulses on cell survival, membrane permeabilization and electrode material release," Bioelectrochemistry, vol. 134, Aug. 2020,14 Pages.

Voyer, D., A. Silve, L. M. Mir, R. Scorretti, and C. Poignard, "Dynamical modeling of tissue electroporation," Bioelectrochemistry, vol. 119, pp. 98-110, 2018.

Wandel, A. et al. "Optimizing Irreversible Electroporation Ablation with a Bipolar Electrode," Journal of Vascular and Interventional Radiology, vol. 27, Issue 9, 1441-1450.e2, 2016.

Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.

Weaver et al., "A brief overview of electroporation pulse strength-duration space: A region where additional ntracellular effects are expected." Bioelectrochemistry vol. 87, pp. 236-243 (2012).

Weaver, Electroporation: A General Phenomenon for Manipulating Cells and Tissues, Journal of Cellular Biochemistry, 51: 426-435, 1993.

Weaver, et al., Theory of Electroporation: A Review, Bioelectrochemistry and Bioenergetics, vol. 41, pp. 136-160, 1996.

Weaver, J. C., Electroporation of biological membranes from multicellular to nano scales, IEEE Tms. Dielectr. Electr. Insul. 10, 754-768 (2003).

Weaver, J.C., "Electroporation of cells and tissues", IEEE Transactions on Plasma Science, 28(1): p. 24-33 (2000).

Weisstein: Cassini Ovals. From MathWorld—A. Wolfram Web Resource; Apr. 30, 2010; http://mathworld.wolfram.com/ (updated May 18, 2011) 2 pages.

Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.

Wittkampf, et al, Myocardial lesion depth with circular electroporation ablation, Circ Arrhythm Electrophysiol, 2012, 5, pp. 581-586.

Wood et al., Technologies for Guidance of Radiofrequency Ablation in the Multimodality Interventional Suite of the Future, Jan. 2007, National Institutes of Health, pp. 1-26.

Wright, On a relationship between the arrhenius parameters from thermal damage studies, Technical Brief, Journalof Biomechanical Engineering, Transactions of the ASME, Apr. 2003, vol. 125, pp. 300-304.

Yang et al., "Dielectric properties of human leukocyte subpopulations determined by selectrorotation as a cell separation criterion." Biophysical Journal, vol. 76, pp. 3307-3314 (1999).

Yao et al., "Study of transmembrane potentials of inner and outer membranes induced by pulsed-electric-field model and simulation." IEEE Trans Plasma Sci, 2007. 35(5): p. 1541-1549.

Yarmush, M. L. et al., "Electroporation-Based Technologies for Medicine: Principles, Applications, and Challenges," Annu. Rev. Biomed. Eng., vol. 16, No. 1,295-320, 2014, 29 pages.

Ybarra, Gary A, et al. "Breast Imaging using Electrical Impedance Tomography." in Suri, J.S., R.M. Rangayyan, and S. Laxminarayan, Emerging Technologies in Breast Imaging and Mammography2008: American Scientific Publishers.

Zhang, et al, MR imaging to assess immediate response to irreversible electroporation for targeted ablation of liver tissues: Preclinical feasibility studies in a rodent model, Radiology, Aug. 2010, vol. 256, No. 2, pp. 424-432.

Zhao, J. et al. "Irreversible electroporation reverses resistance to immune checkpoint blockade in pancreatic cancer", Nature Communications (2019) 10:899,14 pages.

Zhao, Y., S. Bhonsle, S. Dong, Y. Lv, H. Liu, A. Safaai-Jazi, R. V. Davalos, and C. Yao, "Characterization of conductivity changes during high-frequency irreversible electroporation for treatment planning," IEEE Transactions on Biomedical Engineering, vol. 65, No. 8, pp. 1810-1819,2017.

Zhou, et al, Electroporation-mediated transfer of plasmids to the lung results in reduced TLR9 signaling and Inflammation, Gene Therapy, Mar. 8, 2007, 14, pp. 775-780.

Zimmermann, etal., Dielectric Breakdown of Cell Membranes, Biophysical Journal, vol. 14, No. 11, pp. 881-899, 1974.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.

Onik, et al, Irreversible electroporation: Implications for prostate ablation, Technology in Cancer Research and Treatment, Aug. 2007, vol. 6, No. 4, pp. 295-300.

Onik, et al., Sonographic Monitoring of Hepatic Cryosurgery in an Experimental Animal Model, AJR American J. of Roentgenology, vol. 144, pp. 1043-1047, May 1985.

Onik, et al., Ultrasonic Characteristics of Frozen Liver, Cryobiology, vol. 21, pp. 321-328, 1984.

Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.

Onik, G.,P. Mikus, and B. Rubinsky, "Irreversible electroporation: implications for prostate ablation." Technol Cancer Res Treat, 2007. 6(4): p. 295-300.

Organ, L.W., Electrophysiological principles of radiofrequency lesion making, Apply. Neurophysiol., 1976. 39: p. 69-76.

Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.

Pakhomova, O. N., Gregory, B., Semenov 1., and Pakhomov, A. G., BBA— Biomembr., 2014, 1838, 2547-2554.

Partridge, B. R. et al., "High-Frequency Irreversible Electroporation for treatment of Primary Liver Cancer: A Proof-of-Principle Study

(56) References Cited

OTHER PUBLICATIONS in Canine Hepatocellular Carcinoma," J. Vasc. Interv. Radiol, vol. 31, No. 3, 482-491.e4, Mar. 2020, 19 pages.
Paszek et al., "Tensional homeostasis and the malignant phenotype." Cancer Cell, vol. 8, pp. 241-254 (2005).
Pavseij, N. et al. The course of tissue permeabilization studied on a mathematical model of a subcutaneous tumor in small animals. IEEE Trans Biomed Eng 52,1373-1381 (2005).
Pavselj, N., et al., "A numerical model of skin electroporation as a method to enhance gene transfection in skin. 11th Mediterranean Conference on Medical and Biological Engineering and Computing", vols. 1 and 2,16(1-2): p. 597-601 [2007].
PCT Application No. PCT/US 19/51731, International Search Report and Written Opinion dated Feb. 20, 2020,19 pgs.
PCT Application No. PCT/US09/62806, International Search Report (Jan. 19, 2010), Written Opinion (Jan. 19, 2010), and International Preliminary Report on Patentability (Jan. 4, 2010), 15 pgs.
PCT Application No. PCT/US10/53077, International Search Report (Aug. 2, 2011), Written Opinion (Aug. 2, 2011), and International Preliminary Report on Patentability (Apr. 17, 2012).
PCT Application No. PCT/US15/30429, International Search Report and Written Opinion dated Oct. 16, 2015,19 pages.
PCT Application No. PCT/US15/65792, International Search Report (Feb. 9, 2016), Written Opinion (Feb. 9, 2016), and International Preliminary Report on Patentability (Jun. 20, 2017), 15 pages.
PCT Application No. PCT/US2004/043477, International Search Report (Aug. 26, 2005), Written Opinion (Aug. 26, 2005), and International Preliminary Report on Patentability (Jun. 26, 2006).
PCT Application No. PCT/US2009/042100, International Search Report (Jul. 9, 2009), Written Opinion (Jul. 9, 2009), and International Preliminary Report on Patentability (Nov. 2, 2010).
PCT Application No. PCT/US2010/030629, International Search Report (Jul. 15, 2010), Written Opinion (Jul. 15, 2010), and International Preliminary Report on Patentability (Oct. 11, 2011).
PCT Application No. PCT/US2011/062067, International Search Report and Written Opinion dated Jul. 25, 2012.
PCT Application No. PCT/US2011/066239, International Search Report (Aug. 22, 2012), and Written Opinion (Aug. 22, 2012).
PCT International Search Report and Written Opinion from PCT/US2010/053077, dated Aug. 2, 2011.
PCT International Search Report for PCT/US10/29243 dated Jul. 30, 2010, 4 pages.
PCT International Search Report for PCT/US2009/062806, dated Jan. 19, 2010.
PCT International Search Report for WO 2012/051433 dated May 30, 2012.
Pech, et al, Irreversible electroporation of renal cell carcinoma: A first-in-man phase I clinical study, Cardiovasc Intervent Radiol, Aug. 15, 2010.
Pending Application No. 19861489.3 Extended European Search Report dated May 16, 2022 (8 pages).
Pending Application No. EP 09739678.2 Extended European Search Report dated May 11, 2012, 1 pages.
Pending Application No. EP 10824248.8, Extended Search Report (Jan. 20, 2014), 6 pages.
Pending Application No. EP 11842994.3, Extended European Search Report dated Apr. 9, 2014, 34 pages.
Pending Application No. EP 15793361.5, European Search Report dated Dec. 4, 2017, 9 pages.
Pending Application No. PCT/US21/51551, International Search Report and Written Opinion dated Dec. 29, 2021,14 pages.
Philips, IntelliVue Patient Monitor, Jan. 2008, Philips, pp. 1-532 (Year: 2008).
Phillips, et al., Irreversible electroporation on the small intestine, British Journal of Cancer, 2012, pp. 1-6.
Phillips, et al., Nonthermal irreversible electroporation for tissue decellularization, Journal of Biomedical Engineering, Aug. 16, 2010, vol. 132, 091003, pp. 1-8.

Pinero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Polajzer, T. et al., "Cancellation effect is present in high-frequency reversible and irreversible electroporation," Bioelectrochemistry, vol. 132, 2020, 11 pages.
Polak, et al, On the electroporation thresholds of lipid bilayers: Molecular dynamics simulation investigations, J Membrane Biol, Jun. 13, 2013, 246, pp. 843-850.
Precision Office TUNA System, "When Patient Satisfaction is Your Goal." Product Literature Published by VidaMed, Inc., 11 pages (2001).
Pucihar et al, "Numerical determination of transmembrane voltage induced on irregularly shaped cells." Annals of Biomedical Engineering, vol. 34, pp. 642-652 (2006).
Qiao et al. Electrical properties of breast cancer cells from impedance measurement of cell suspensions, 2010, Journal of Physics, 224, 1-4 (2010).
Radeva, et al, Induction of apoptosis and necrosis in cancer cells by electric fields, electromagnetic fields, and photodynamically active quinoids, Electromagnetic Biology and Medicine, 2003, 23, pp. 185-200.
Rajagopal, V. and S.G. Rockson, Coronary restenosis: a review of mechanisms and management, The American Journal of Medicine, 2003, 115(7): p. 547-553.
Rebersek, et al., Advantages and disadvantages of different concepts of electroporation pulse generation, Automatika, 2011, 52, 1, pp. 12-19.
Reilly, J. P. et al., "Sensory Effects of Transient Electrical Stimulation-Evaluation with a Neuroelectric Model," IEEE Trans. Biomed. Eng., vol. BME-32, No. 12, 1001-1011, 1985, 11 pages.
Ringel-Scaia, V. M. et al., High-frequency irreversible electroporation is an effective tumor ablation strategy that induces immunologic cell death and promotes systemic anti-tumor immunity. EBioMedicine, 2019,44,112-125.
Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rossmeisl, John H. et al. Safety and feasibility of the NanoKnife system for irreversible electroporation ablative treatment of canine spontaneous intracranial gliomas. J. Neurosurgery 123.4 (2015): 1008-1025.
Rowland, et al., Transvenous ablation of atrioventricular conduction with a low energy power source, Br Heart J, 1989, 62, pp. 361-366.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Rubinsky, et al, Optimal parameters for the destruction of prostate cancer using irreversible electroporation, The Journal of Urology, Dec. 2008, vol. 180, pp. 2668-2674.
Rubinsky, L. et al., "Electrolytic Effects During Tissue Ablation by Electroporation," Technol. Cancer Res. Treat., vol. 15, No. 5, NP95-103, 2016, 9 pages.
Sabuncu, et al., Dielectrophoretic separation of mouse melanoma clones, Biomicrofluidics, Jun. 16, 2010, 4, 021101, pp. 1-7.

(56) References Cited

OTHER PUBLICATIONS

SAI Infusion Technologies, "Rabbit Ear Vein Catheters", https://www.sai-infusion.com/products/rabbit-ear-catheters, Aug. 10, 2017 webpage printout, 5 pages.

Saldanha, et al., Current tumor ablation technologies: Basic science and device review, Seminars in Interventional Radiology, 2010, vol. 27, No. 3, pp. 247-254.

Salford, L.G., et al., "A new brain tumour therapy combining bleomycin with in vivo electropermeabilization", Biochem. Biophys. Res. Commun., 194(2): 938-943 (1993).

Salmanzadeh et al., "Investigating dielectric properties of different stages of syngeneic murine ovarian cancer cells" Biomicrofluidics 7, 011809 (2013), 12 pages.

Salmanzadeh et al., "Sphingolipid Metabolites Modulate Dielectric Characteristics of Cells in a Mouse Ovarian Cancer Progression Model." Integr. Biol., 5(6), pp. 843-852 (2013).

Salmanzadeh et al., "Dielectrophoretic differentiation of mouse ovarian surface epithelial cells, macrophages, and fibroblasts using contactless dielectrophoresis." Biomicrofluidics, vol. 6,13 Pages (2012).

Sanchez, B., G. Vandersteen, R. Bragos, and J. Schoukens, "Basics of broadband impedance spectroscopy measurements using periodic excitations," Measurement Science and Technology, vol. 23, No. 10, p. 105501,2012.

Sanchez, B., G. Vandersteen, R. Bragos, and J. Schoukens, "Optimal multisine excitation design for broadband electrical impedance spec-troscopy," Measurement Science and Technology, vol. 22, No. 11, p. 115601,2011.

Sanders, et al., Nanosecond pulse generator with scalable pulse amplitude, IEEE, 2008, pp. 65-68.

Sankaranarayanan, et al., Effect of irreversible electroporation on cell proliferation in fibroblasts, Proc. ESA Annual Meeting on Electrostatics, 2011, pp. 1-8.

Sano et al., "In-vitro bipolar nano- and microsecond electro-pulse bursts for irreversible electroporation therapies." Bioelectrochemistry vol. 100, pp. 69-79 (2014).

Sano et al., "Modeling and Development of a Low Frequency Contactless Dielectrophoresis (cDEP) Platform to Sort cancer Cells from Dilute Whole Blood Samples." Biosensors & Bioelectronics, 8 pages (2011).

Sano et al., "Contactless Dielectrophoretic Spectroscopy: Examination of the Dielectric Properties of Cells Found in Blood." Electrophoresis, 32, pp. 3164-3171, 2011.

Sano, et al, Towards the creation of decellularized organ constructs using irreversible electroporation and active mechanical perfusion, Biomedical Engineering Online, 2010, 9, 83, pp. 1-16.

Sano, M. B. et al., "Burst and continuous high frequency irreversible electroporation protocols evaluated in a 3D tumor model," Phys. Med. Biol., vol. 63, No. 13, 2018, 17 pages.

Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. Interv. Radiol., vol. 29, No. 6, 893-898.e4, Jun. 2018, 18 pages.

Saur et al., "CXCR4 expression increases liver and lung metastasis in a mouse model of pancreatic cancer." Gastroenterology, vol. 129, pp. 1237-1250 (2005).

Savader, et al."Treatment of Hemodialysis Catheter-associated Fibrin Sheaths by rt-PA Infusion: Critical Analysis of 124 Procedures," J Vasc Intery Radiol 2001; 12:711-715.

Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.

Schoenbach et al., "Intracellular effect of ultrashort electrical pulses." Bioelectromagnetics, 22 (2001) pp. 440-448.

Schoenbach, et al., Bioelectric effects of intense nanosecond pulses, IEEE Transactions on Dielectric and Electrical Insulation, 2007, vol. 14, Iss. 5, pp. 1088-1109.

Seibert, et al., Clonal variation of MCF-7 breast cancer cells in vitro and in athymic nude mice, Cancer Research, May 1983, 43, pp. 2223-2239.

Seidler et al., "A Cre-IoxP-based mouse model for conditional somatic gene expression and knockdown in vivo by using avian retroviral vectors." Proceedings of the National Academy of Sciences, vol. 105, p. 10137-10142 (2008).

Sel, D. et al. Sequential finite element model of tissue electropermeabilization. IEEE Transactions on Biomedical Engineering 52, 816-827, doi:10.1109/tbme.2005.845212 (2005).

Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).

Sersa, et al, Tumor blood flow modifying effect of electrochemotherapy with Bleomycin, Anticancer Research, 1999, 19, pp. 4017-4022.

Sersa, et al., Reduced Blood Flow and Oxygenation in SA-I Tumours after Electrochemotherapy with Cisplatin, British Journal of Cancer, 87, 1047-1054, 2002.

Sersa, et at, Tumour Blood Flow Modifying Effects of Electrochemotherapy: a Potential Vascular Targeted Mechanism, Radiol. Oncol., 37(1): 43-8,2003.

Shafiee, et al, A preliminary study to delineate irreversible electroporation from thermal damage using the Arrhenius equation, Journal of Biomedical Engineering, Jul. 2009, vol. 131, 074509, pp. 1-5.

Shao, Qi et al. Engineering T cell response to cancer antigens by choice of focal therapeutic conditions, International Journal of Hyperthermia, 2019, DOI: 10.1080/02656736.2018.1539253.

Sharma, A., et al., "Review on Thermal Energy Storage with Phase Change Materials and Applications", Renewable Sustainable Energy Rev. 13(2), 318-345 (2009).

Sharma, et al, Poloxamer 188 Decreases Susceptibility of Artificial Lipid Membranes to Electroporation, Biophysical Journal, vol. 71, No. 6, pp. 3229-3241, Dec. 1996.

Shiina, et al., Percutaneous ethanol injection therapy for hepatocellular carcinoma: Results in 146 patients, AJR, May 1993, 160, pp. 1023-1028.

Soden, et al., Successful application of targeted electrochemotherapy using novel flexible electrodes and low dose bleomycin to solid tumors, Cancer Letters, 2006, 232 pp. 300-310.

Son, et al., Basic features of a cell electroporation model: illustrative behavior for tw overy different pulses, J Membrane Biol, Jul. 22, 2014, 247, pp. 1209-1228.

Song, Z.Q., et al., Mechanisms for steep pulse irreversible electroporation technology to kill human large cell lung cancer cells L9981. International Journal of Clinical and Experimental Medicine, 2014. 7(8): p. 2386-2394.

Szot et al., "3D in vitro bioengineered tumors based on collagen I hydrogels." Biomaterials vol. 32, pp. 7905-7912 (2011).

Talele, S. and P. Gaynor, "Non-linear time domain model of electropermeabilization: Effect of extracellular conductivity and applied electric field parameters", Journal of Electrostatics,66(5-6): p. 328-334 (2008).

Talele, S. and P. Gaynor, "Non-linear time domain model of electropermeabilization: Response of a single cell to an arbitrary applied electric field", Journal of Electrostatics, 65(12): p. 775-784 (2007).

Talele, S., et al., "Modelling single cell electroporation with bipolar pulse parameters and dynamic pore radii". Journal of Electrostatics, 68(3): p. 261-274 (2010).

Kirson et al., "Alternating electric fields arrest cell proliferation in animal tumor models and human brain tumors." Proceedings of the National Academy of Sciences vol. 104, p. 10152-10157 (2007).

Knight, et al, Direct imaging of transvenous radiofrequency cardiac ablation using a steerable fiberoptic infrared endoscope, Heart Rhythm Society, Oct. 2005, vol. 2, No. 10, pp. 1116-1121.

Kolb, J.F., et al., "Nanosecond pulsed electric field generators for the study of subcellular effects", Bioelectromagnetics, 27(3): p. 172-187 (2006).

Kotnik and Miklavcic, "Theoretical evaluation of voltage inducement on internal membranes of biological cells exposed o electric fields." Biophysical Journal, vol. 90(2), pp. 480-491 (2006).

(56) References Cited

OTHER PUBLICATIONS

Kotnik et al., "Sensitivity of transmembrane voltage induced by applied electric fields—A theoretical analysis", Bioelectrochemistry and Bioenergetics, vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses". Part I. Increased efficiency of permeabilization. Bioelectrochemistry, 54(1): p. 83-90 (2001).
Kotnik, T., et al., "Role of pulse shape in cell membrane electropermeabilization", Biochimica Et Biophysica Acta-iomembranes, 1614(2): p. 193-200 (2003).
Kotnik, T., et al., "Cell membrane electropermeabilization by symmetrical bipolar rectangular pulses. Part II. Reducec electrolytic contamination", Bioelectrochemistry, 54(1): p. 91-5 (2001).
Kranjc, M., S. Kranjc, F. Bajd, G. Sersa, I. Sersa, and D. Miklavcic, "Predicting irreversible electroporation-induced issue damage by means of magnetic resonance electrical impedance tomography," Scientific reports, vol. 7, No. 1, pp. 1-10, 2017.
Kroeger, et al., Curvature-driven pore growth in charged membranes during charge-pulse and voltage-clamp experiments, Biophysical Journal, Feb. 2009, 96, 3, pp. 907-916.
Kurup, et al, Image-Guided Percutaneous Ablation of Bone and soft Tissue Tumors, Semin Intervent Radiol 2010, 27:276-284.
Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Laufer et al., "Electrical impedance characterization of normal and cancerous human hepatic tissue." Physiological Measurement, vol. 31, pp. 995-1009 (2010).
Lavee, et al., "A Novel Nonthermal Energy Source for Surgical Epicardial Atrial Ablation: Irreversible Electroporation," The Heart Surgery Forum #2006-1201, vol. 10 (2): 96-101 (2007).
Lebar et al., "Inter-pulse interval between rectangular voltage pulses affects electroporation threshold of artificial lipid bilayers." IEEE Transactions on Nano Bioscience, vol. 1 (2002) pp. 116-120.
Lee, Cassinian Oval, Nov. 2004, Mathematics Department of The University of California at Irvine, pp. 1-5.
Lee, E. W. et al. Advanced Hepatic Ablation Technique for Creating Complete Cell Death : Irreversible Electroporation. Radiology 255, 426-433, doi:10.1148/radiol. 10090337 (2010).
Lee, et al, Imaging guided percutaneous irreversible electroporation: Ultrasound and immunohistological correlation, Technology in Cancer Research and Treatment, Aug. 2007, vol. 6, No. 4, pp. 287-293.
Lee, et al, Irreversible electroporation: A novel image-guided cancer therapy, Gut and Liver, Sep. 2010, vol. 4, Supp. 1, pp. S99-S104.
Lee, R. C., D. J. Canaday, and S. M. Hammer. Transient and stable ionic permeabilization of isolated skeletal muscle cells after electrical shock. J. Burn Care Rehabil. 14:528-540,1993.
Li, et al, The effects of irreversible electroporation (IRE) on nerves, PLOS One, Apr. 14, 2011, vol. 6, Iss. 4, e18831, pp. 1-7.
Lin, et al., An optically induced cell lysis device using dielectrophoresis, Applied Physics Letters, Jan. 20, 2009, 94, 033901, pp. 1-3.
Lion, et al., Poly(I:C) enhances the susceptibility of leukemic cells to NK cell cytotoxicity and phagocytosis by DC, PLOS One, vol. 6, Iss. 6, e20952, pp. 1-10, Jun. 17, 2011.
Liu, et al., Measurement of Pharyngeal Transit Time by Electrical Impedance Tomography, Clin. Phys. Physiol. Meas., 1992, vol. 13, Suppl. A, pp. 197-200.
Long, G., et al., "Targeted Tissue Ablation With Nanosecond Pulses", Ieee Transactions on Biomedical Engineering, 58(8) (2011).
Lu, et al, Irreversible electroporation: Ready for prime time?, Techniques in Vascular and Interventional Radiology, 2013, 16, pp. 277-286.
Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.
Lurquin, Review: Gene transfer by electroporation, Molecular Biotechnology, 1997, vol. 7, pp. 5-31.
Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).
Lynn, et al., A New Method for the Generation and Use of Focused Ultrasound in Experimental Biology, The Journal of General Physiology, vol. 26,179-193,1942.
Macek Lebar and Miklavcic, "Cell electropermeabilization to small molecules in vitro: control by pulse parameters." Radiology and Oncology, vol. 35(3), pp. 193-202 (2001).
Machado-Aranda, et al, Gene transfer of the Na+, K+K—ATPase B1 subunit using electroporation increases lung liquid clearance, American Journal of Respiratory and Critical Care Medicine, 2004, vol. 171, pp. 204-211.
Macherey, O et al., "Asymmetric pulses in cochlear implants: Effects of pulse shape, polarity, and rate," JARO—J. Assoc. Res. Otolaryngol., vol. 7, No. 3, 253-266, 2006, 14 pages.
Mahmood, F., et al., "Diffusion-Weighted MRI for Verification of Electroporation-Based Treatments", Journal of Membrane Biology 240:131-138 (2011).
Mahmood, Gehl, Optimizing clinical performance and geometrical robustness of a new electrode device for ntracranial tumor electroporation, Bioelectrochemistry, Jan. 6, 2011, 81, pp. 10-16.
Mahnic-Kalamiza, et al., "Educational application for visualization and analysis of electric field strength in multiple electrode electroporation," BMC Med Educ, vol. 12:102,13 pp. 2012.
Mali, et al., "The Effect of Electroporation Pulses on Functioning of the Heart," Med Biol Eng Comput (2008) 46:745-757.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech, in Cancer Res. and Treatment, vol. 6, No. 4, Aug. 2007, pp. 307-312.
Maor, et al, Intravascular irreversible electroporation: Theoretical and experimental feasibility study, 30th Annual International IEEE EMBS Conference, IEEE, Aug. 20, 2008, pp. 2051-2054.
Maor, et al, Irreversible electroporation attenuates neointimal formation after angioplasty, IEEE Transactions on Biomedical Engineering, Sep. 2008, vol. 55, No. 9, pp. 2268-2274.
Maor, et al., Non Thermal Irreversible Electroporation: Novel Technology for Vascular Smooth Muscle Cells Ablation, PLoS One, Mar. 2009, 4(3): p. e4757, 9 pages.
Maor, Rubinsky, Endovascular nonthermal irreversible electroporation: A finite element analysis, Journal of Biomedical Engineering, Feb. 7, 2010, vol. 132, 031008, pp. 1-7.
Marszalek et al., "Schwan equation and transmembrane potential induced by alternating electric field." Biophysical Journal, vol. 58, pp. 1053-1058 (1990).
Martin et al., "Gene Transfer to Intact Mesenteric Arteries by Electroporation" Journal of Vascular Research, 37:372-380 (2000).
Martin, n.R.C.G., et al., "Irreversible electroporation therapy in the management of locally advanced pancreatic adenocarcinoma." Journal of the American College of Surgeons, 2012.215(3): p. 361-369.
Martinsen, O. G. and Grimnes, S., Bioimpedance and bioelectricity basics. Academic press, 2011.
Marty, IM., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.

\* cited by examiner

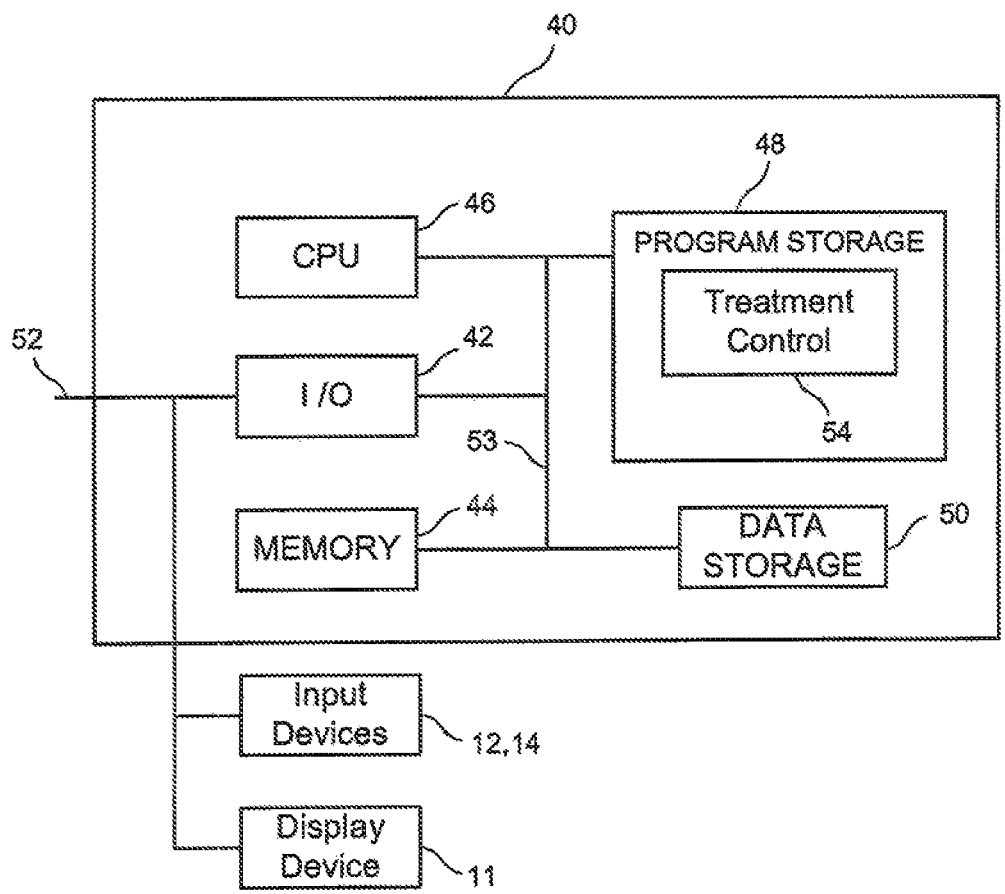
F I G. 2

Probe Selection

Probe type
- ● Bipolar probe
- ○ Two probe array
- ○ Three probe array
- ○ Four probe array
- ○ Five probe array
- ○ Six probe array
- ○ Six probe array 10mm
- ○ Six probe array 15mm Side view — 30mm Top view — 15mm Diagrams shown for examples only

Probes Connection Status
- ☑ (1) Connected
- ☐ (2) Not Connected
- ☐ (3) Not Connected
- ☐ (4) Not Connected
- ☐ (5) Not Connected
- ☐ (6) Not Connected Back  Settings  About  Next

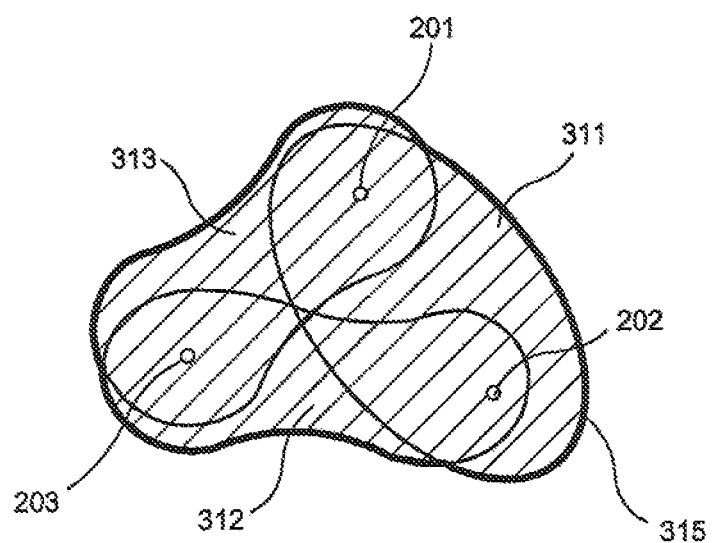
F I G. 15

FIG. 16

| Y\X | 0x0000 | 0x0001 | 0x0002 | 0x0003 | 0x0004 | 0x0005 | 0x0006 | 0x0007 | 0x0008 | 0x0009 | 0x000A | 0x000B | 0x000C | 0x000D | 0x000E | 0x000F | 0x0010 | 0x0011 | 0x0012 | 0x0013 | 0x0014 |
|---|---|---|---|---|---|---|---|---|---|---|---|---|---|---|---|---|---|---|---|---|---|
| 0x0000 | 657 | 682 | 705 | 725 | 742 | 753 | 760 | 761 | 757 | 749 | 737 | 721 | 703 | 683 | 662 | 640 | 617 | 594 | 571 | 548 | 526 |
| 0x0001 | 703 | 734 | 763 | 788 | 809 | 823 | 831 | 831 | 826 | 815 | 799 | 779 | 757 | 733 | 707 | 680 | 653 | 626 | 600 | 574 | 549 |
| 0x0002 | 755 | 794 | 831 | 864 | 890 | 908 | 917 | 917 | 908 | 892 | 871 | 847 | 819 | 789 | 757 | 725 | 693 | 661 | 631 | 601 | 573 |
| 0x0003 | 814 | 864 | 912 | 955 | 990 | 1014 | 1024 | 1021 | 1007 | 985 | 957 | 924 | 889 | 852 | 814 | 775 | 737 | 699 | 664 | 630 | 597 |
| 0x0004 | 880 | 944 | 1009 | 1069 | 1118 | 1149 | 1160 | 1151 | 1128 | 1096 | 1057 | 1015 | 971 | 924 | 877 | 830 | 785 | 740 | 699 | 659 | 623 |
| 0x0005 | 953 | 1039 | 1129 | 1215 | 1287 | 1330 | 1340 | 1319 | 1279 | 1230 | 1177 | 1122 | 1065 | 1008 | 950 | 892 | 837 | 784 | 735 | 689 | 649 |
| 0x0006 | 1033 | 1147 | 1276 | 1409 | 1523 | 1589 | 1591 | 1541 | 1469 | 1393 | 1320 | 1248 | 1177 | 1105 | 1032 | 962 | 894 | 831 | 774 | 722 | 675 |
| 0x0007 | 1114 | 1267 | 1456 | 1673 | 1883 | 2001 | 1970 | 1845 | 1706 | 1588 | 1489 | 1400 | 1311 | 1220 | 1128 | 1040 | 957 | 881 | 813 | 753 | 700 |
| 0x0008 | 1190 | 1388 | 1660 | 2038 | 2498 | 2785 | 2610 | 2260 | 1990 | 1815 | 1693 | 1588 | 1479 | 1361 | 1241 | 1127 | 1024 | 932 | 853 | 784 | 724 |
| 0x0009 | 1248 | 1487 | 1852 | 2479 | 3685 | 5049 | 3828 | 2767 | 2289 | 2067 | 1837 | 1702 | 1541 | 1376 | 1225 | 1094 | 983 | 890 | 812 | 745 | 745 |
| 0x000A | 1276 | 1533 | 1945 | 2736 | 5016 | #DIV/0! | 5135 | 3104 | 2523 | 2338 | 2217 | 2036 | 1784 | 1538 | 1330 | 1164 | 1030 | 923 | 836 | 763 | 763 |
| 0x000B | 1266 | 1510 | 1883 | 2521 | 3744 | 5135 | 3959 | 2974 | 2643 | 2853 | 3859 | 2610 | 2118 | 1719 | 1433 | 1225 | 1069 | 949 | 854 | 776 | 776 |
| 0x000C | 1225 | 1433 | 1719 | 2118 | 2610 | 2946 | 2853 | 2643 | 2632 | 2923 | 3194 | 2610 | 2118 | 1719 | 1433 | 1266 | 1097 | 964 | 864 | 783 | 783 |
| 0x000D | 1164 | 1330 | 1538 | 1784 | 2036 | 2217 | 2289 | 2338 | 2289 | 2289 | 3828 | 2610 | 2118 | 1719 | 1487 | 1276 | 1097 | 966 | 864 | 784 | 783 |
| 0x000E | 1094 | 1225 | 1376 | 1541 | 1702 | 1837 | 1945 | 2067 | 2260 | 2767 | 5049 | 2785 | 1852 | 1538 | 1376 | 1248 | 1079 | 953 | 855 | 775 | 775 |
| 0x000F | 1024 | 1128 | 1241 | 1361 | 1479 | 1588 | 1693 | 1815 | 1990 | 2289 | 3049 | 2498 | 1660 | 1376 | 1241 | 1190 | 1042 | 927 | 836 | 761 | 761 |
| 0x0010 | 957 | 1040 | 1127 | 1220 | 1311 | 1409 | 1523 | 1591 | 1706 | 1883 | 2001 | 1845 | 1455 | 1267 | 1127 | 1114 | 991 | 892 | 810 | 742 | 742 |
| 0x0011 | 894 | 962 | 1032 | 1105 | 1177 | 1248 | 1320 | 1393 | 1469 | 1523 | 1589 | 1541 | 1276 | 1147 | 1039 | 1033 | 934 | 850 | 779 | 718 | 718 |
| 0x0012 | 837 | 892 | 950 | 1008 | 1065 | 1122 | 1177 | 1230 | 1279 | 1287 | 1330 | 1319 | 1129 | 1039 | 953 | 953 | 875 | 806 | 745 | 692 | 692 |
| 0x0013 | 785 | 830 | 877 | 924 | 971 | 1015 | 1057 | 1096 | 1128 | 1149 | 1160 | 1118 | 1009 | 944 | 880 | 880 | 818 | 761 | 710 | 663 | 663 |
| 0x0014 | 737 | 775 | 814 | 852 | 889 | 924 | 955 | 985 | 1007 | 1021 | 1024 | 1014 | 912 | 864 | 814 | 814 | 765 | 718 | 675 | 635 | 635 |

Lesion: 2.5 x 1.5 @ 0°

| Locked | | 2 | 3 | 4 | 5 | 6 |
|---|---|---|---|---|---|---|
| ☐ | 1 | 22.0 | | | 20.0 | |
| ☒ | 2 | | 19.0 | 17.0 | 14.0 | |
| ☐ | 3 | | | 11.0 | | |
| ☐ | 4 | | | | 21.0 | |
| ☐ | 5 | | | | | |
| ☐ | 6 | | | | | |

Probe Distance Adjuster — 333

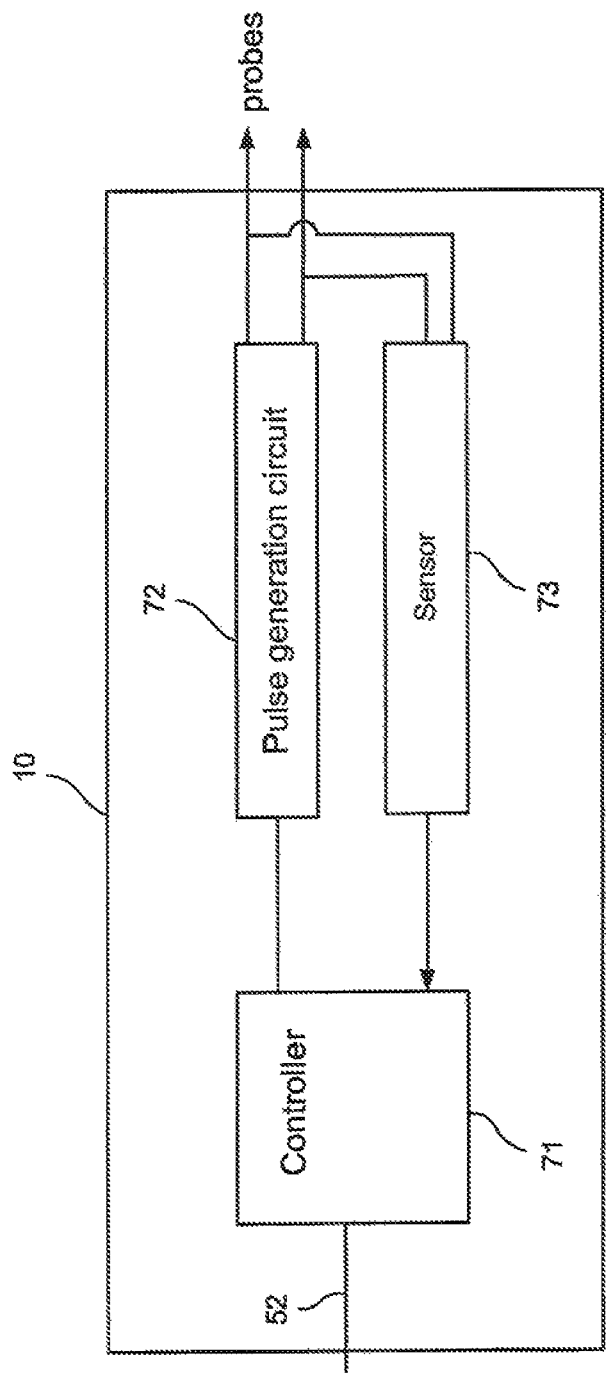
F I G. 29

Pulse Generation

| | Probe + | Probe - | Initial Voltage | Voltage | Pulse Length | Num. Pulses | Total Pulses Delivered | Status |
|---|---|---|---|---|---|---|---|---|
| △ | 1 | 3 | 3000 | 3000 | 100 | 90 | 90 | ⊘ Completed |
| | 2 | 4 | 3000 | 3000 | 100 | 90 | 20 | ⚠ High Current |
| | 1 | 2 | 2700 | 2700 | 100 | 90 | 90 | ⊘ Completed |
| | 3 | 4 | 2700 | 2700 | 100 | 90 | 90 | ⊘ Completed |
| | 2 | 3 | 2100 | 2100 | 100 | 90 | 90 | ⊘ Completed |
| | 4 | 1 | 2100 | 2100 | 100 | 90 | 90 | ⊘ Completed |

220  221  229  222  223  224  401  402

426 △ Continue Procedure

Delivery completed

427 △ Stop Procedure

Run section
✕ Abort delivery
ECG disabled
△ Arm ⊙ Pulse

Charge section
2998V
🔍 Charge

Ⓑ Back    Export ⬚    About ⑦    New Probe Selection ⓘ    New pattern →

FIG. 30

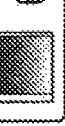
F I G. 31

FIG. 32

METHODS OF STERILIZATION AND TREATING INFECTION USING IRREVERSIBLE ELECTROPORATION

CROSS REFERENCE TO RELATED APPLICATIONS

This application is related to U.S. non-provisional application Ser. No. 12/488,070, filed Jun. 19, 2009; Ser. No. 12/751,826, filed Mar. 31, 2010; and Ser. No. 12/751,854, filed Mar. 31, 2010; and claims priority to U.S. provisional application No. 61/834,471 filed on Jun. 13, 2013; all of which are incorporated by reference herein.

FIELD OF THE INVENTION

The present invention relates to methods of treating infections in mammals using irreversible electroporation (IRE) to destroy the pathogenic microorganisms comprising the infection and methods of sterilization of implanted medical devices using IRE.

BACKGROUND OF THE INVENTION

Infections are caused by parasitic microorganisms such as viruses, bacteria or fungi which invade the host and rapidly reproduce. The body's natural immune system is designed to combat most infections. Some infections may become chronic, particularly if the host has a compromised immune system. Uncontrolled infections may cause serious health problems including death. Infections are frequently associated with wounds and may also occur in the locale of implanted devices such as ports, catheters, stents, artificial cartilaginous implants, orthopedic prosthetics, pacemakers, PICCs, prosthetic knee or hip implants, tooth implants, heart valves, spinal implants, and other types of plastic and/or metallic devices, to name a few. These medical devices can become infected after implanted into a patient. Long-term implants can be particularly susceptible to infection. Infection of implanted medical devices can constitute one of the most serious complications after surgery. Removing these infected medical devices can require lengthy procedures to remove and replace the old infected devices with a new device. Such procedures can involve steps such as removing the infected implant through surgical procedure, and/or administering antibiotics, waiting for any infection to heal, and then performing another surgical procedure to re-insert a new medical implant into the patient. In the case of cartilaginous implants, this may have to be repeated several times and may require administering not only a new cartilage implant but also numerous doses of antibiotics in order to enable the infection and the patient's skin to heal and then to reinsert a new artificial cartilage implant. Thus, multiple surgeries can be required. This can greatly increase procedure time and costs and can cause much discomfort to the patient. Pharmaceuticals such as antimicrobial agents and antibiotics can be used to fight infections in such cases, but there are drawbacks to the use of these agents including allergic reactions, negative interactions with other drugs, and ineffective treatment due to an increase in resistant strains of these microorganisms. Sometimes a membrane can develop over infected areas, thereby creating an impassable barrier to antibiotics.

Despite the many problems with infections of implantable medical devices, little has been done to address the cost, pain, and increased procedure time and to present effective solutions for sterilizing and/or treating infections that occur as a result of implanted medical devices. Most procedures involve removing infected devices and/or sterilizing medical devices through external application of bactericidal solutions or temperature extremes such as thermal heating or freezing, UV light, RF, microwave, or other radiation measures.

Therefore, it is desirable to provide a cost-effective, painless, efficient method for treating infections by sterilizing infected implanted medical devices which methods can overcome the problems of traditional pharmaceutical treatment, such as, for example, resistance to systemic antibiotics. The methods provided herein use irreversible electroporation to sterilize implanted medical devices, thereby treating infection in patients, providing increased treatment efficacy, and eliminating or minimizing allergic reactions, which eliminates the chance of interactions with other drugs. This could also enhance patient quality of life, which would be very beneficial for patients having extreme arthritis, for example.

What is provided herein is a method of using irreversible electroporation (IRE) to treat parts of the human body that have been subject to infection. This method avoids surgical methods that require removal surgery, a waiting period, then replacement of an infected medical device. This method can greatly improve outcomes, particularly for devices where infection may be catastrophic, i.e., a prosthetic knee or hip implant. It can also greatly improve costs and improve the longevity of implanted medical devices which are susceptible to infection, such as, for example, implantable ports. Such infection can be on or within a medical device that is implanted within a patient, as described above. Alternatively, a patient's tissue can be infected due to some other type of infection, for example, gangrene. IRE can be used to treat such infections and/or simultaneously sterilize an implanted medical device, as described herein to solve the above-mentioned problems.

Electroporation is defined as a phenomenon that makes cell membranes permeable by exposing them to certain electric pulses. As a function of the electrical parameters, electroporation pulses can have two different effects on the permeability of the cell membrane. The permeabilization of the cell membrane can be reversible or irreversible as a function of the electrical parameters used. Reversible electroporation is the process by which the cellular membranes are made temporarily permeable. The cell membrane will reseal a certain time after the pulses cease, and the cell will survive. Reversible electroporation is most commonly used for the introduction of therapeutic or genetic material into the cell. Irreversible electroporation also creates pores in the cell membrane but these pores do not reseal, resulting in cell death.

Irreversible electroporation has recently been discovered as a viable alternative for the ablation of undesired tissue. See, in particular, PCT Application No. PCT/US04/43477, filed Dec. 21, 2004. An important advantage of irreversible electroporation, as described in the above reference application, is that the undesired tissue is destroyed without creating a thermal effect. When tissue is ablated with thermal effects, not only are the cells destroyed, but the connective structure (tissue scaffold) and the structure of blood vessels are also destroyed, and the proteins are denatured. This thermal mode of damage detrimentally affects the tissue, that is, it destroys the vasculature structure and bile ducts, and produces collateral damage.

Irreversible and reversible electroporation without thermal effect to ablate tissue offers many advantages. One advantage is that it does not result in thermal damage to target tissue or other tissue surrounding the target tissue. Another advantage is that it only ablates cells and does not damage blood vessels or other non-cellular or non-living materials such as implanted medical devices.

Although the following examples discuss using the present invention and method to destroy various infectious cells, for example, such as implanted medical device-related bacteremia, that may substantially cover various implanted medical devices, persons of ordinary skill in the art will appreciate that the present devices and methods can be used to treat any undesirable cellular growth, including infectious cells, as well as to sterilize implanted medical devices.

SUMMARY OF THE DISCLOSURE

A method of treating an infection in patient that involves providing an ablation device, wherein the device comprises at least one electrode inserting the ablation device into a target tissue of the patient. The tissue at least partially surrounds an implanted medical device, and the outer surface of the medical device is at least partially covered by infectious cells. The method also involves positioning the at least one electrode in or near the implanted medical device and delivering electrical pulses to or near the implanted medical device sufficient to irreversibly electroporate the infectious cells.

BRIEF DESCRIPTION OF THE DRAWINGS

FIG. 2 is a schematic diagram of a treatment control computer of the present invention.

FIG. 4 is a screen shot of a "Probe Selection" screen of the treatment control module showing a side view and top view of the bipolar probe and an example of the general shape of the treatment zone that can be generated by such a probe type. The "treatment zone", as defined herein, can comprise infected tissue cells.

FIG. 7 is a screen shot of a "Probe Selection" screen of the treatment control module showing a side view and top view of the four probe array and an example of the general shape of the treatment zone that can be generated by a four probe array.

FIG. 9 is a screen shot of a "Probe Selection" screen of the treatment control module showing a side view and top view of the six probe array and an example of the general shape of the treatment zone that can be generated by a six probe array.

FIG. 15 illustrates an example of a three probe array defining three individual treatment zones, which combine to form a combined treatment region.

FIG. 16 is an example of a spreadsheet of the E-field values that are determined for x, y coordinates on the grid, as will be further described below in reference to Example 2.

FIG. 29 illustrates details of the generator shown in FIG. 1, including elements for detecting an over-current condition.

FIG. 30 is a screen shot of a "Pulse Generation" screen of the treatment control module showing the status of the treatment parameters after the treatment procedure.

FIG. 31 is a screen shot of a "Pulse Generation" screen of the treatment control module showing a dialogue box that pops up if the "continue procedure" button is pressed in the example.

FIG. 32 is a screen shot of a "Pulse Generation" screen of the treatment control module showing the status of the treatment parameters during the re-treatment procedure.

DETAILED DESCRIPTION OF THE INVENTION

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Disclosed herein are methods for treating infection in mammals using irreversible electroporation to destroy pathogenic microorganisms comprising the infection. In particular, the methods involve using a medical device to deliver electrical pulses to the treatment zone that comprises an implanted medical device and potentially infectious cells within a non-thermal irreversible electroporation range. A probe comprising at least one electrode is adapted to receive from a voltage generator a plurality of electrical pulses in an amount sufficient to cause destruction of cells comprising the infection. The number of pulses, pulse length, pulse amplitude can be used to irreversibly electroporate a target tissue. Also presented herein is a method for sterilizing an implanted medical device using irreversible electroporation.

Figure 1:
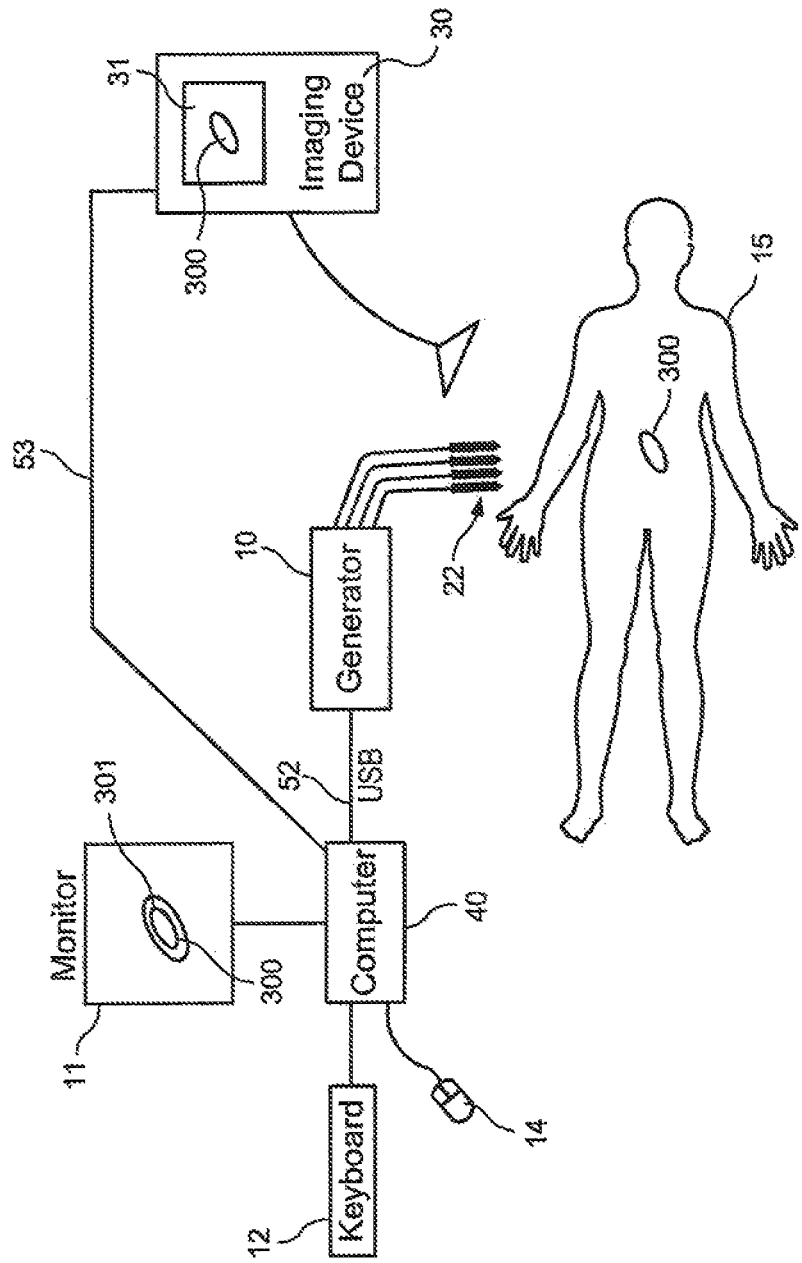
FIG. 1 illustrates several components that can be used with the present invention to treat a patient using IRE or to sterilize an implanted medical device.

One embodiment of the present invention is illustrated in FIGS. 1 through 35. The components that can be used with the present invention are illustrated in FIG. 1. One or more probes 22 can deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 can include six separate receptacles for receiving up to six individual probes 22 which are adapted to be plugged into the respective receptacle. The receptacles are each labeled with a number in consecutive order. In other embodiments, the voltage pulse generator 10 can have any number of receptacles for receiving more or less than six probes.

In the embodiment shown, each probe 22 includes either a monopolar electrode or bipolar electrodes having two electrodes separated by an insulating sleeve. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein. The generator 10 is connected to a treatment control computer 40 having input devices such as keyboard 12 and a pointing device 14, and an output device such as a display device 11 for viewing an image of a target treatment area such as a target tissue 300 surrounded by a safety margin 301. The therapeutic energy delivery device 20 is used to treat a target tissue 300 inside a patient 15. In one aspect, the target tissue can comprise infectious cells and/or an implanted medical device comprising infectious cells. An imaging device 30 includes a monitor 31 for viewing the target tissue 300 inside the patient 15 in real time. Examples of imaging devices 30 include ultrasonic, CT, MRI and fluoroscopic devices as are known in the art.

The present invention includes computer software (treatment control module 54) which assists a user to plan for, execute, and review the results of a medical treatment procedure, as will be discussed in more detail below. For example, the treatment control module 54 assists a user to plan for a medical treatment procedure by enabling a user to more accurately position each of the probes 22 of the therapeutic energy delivery device 20 in relation to the target tissue 300 in a way that will generate the most effective treatment zone. The treatment control module 54 can display the anticipated treatment zone based on the position of the probes and the treatment parameters. The treatment control module 54 can display the progress of the treatment in real time and can display the results of the treatment procedure after it is completed. This information can be used to determine whether the treatment was successful and whether it is necessary to re-treat the patient.

For purposes of this application, the terms "code", "software", "program", "application", "software code", "software module", "module" and "software program" are used interchangeably to mean software instructions that are executable by a processor.

The "user" can be a physician or other medical professional. The treatment control module 54 executed by a processor outputs various data including text and graphical data to the monitor 11 associated with the generator 10.

Referring now to FIG. 2, the treatment control computer 40 of the present invention manages planning of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment control module 54 which includes a user interface module that interacts with the user in planning for, executing and reviewing the result of a treatment. Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communications link 52. In a preferred embodiment, the communication link 52 is a USB link.

In one embodiment, the imaging device 30 is a stand alone device which is not connected to the computer 40. In the embodiment as shown in FIG. 1, the computer 40 is connected to the imaging device 30 through a communications link 53. As shown, the communication link 53 is a USB link. In this embodiment, the computer can determine the size and orientation of the target tissue 300 by analyzing the data such as the image data received from the imaging device 30, and the computer 40 can display this information on the monitor 11. In this embodiment, the target tissue generated by the imaging device 30 can be directly displayed on the grid 200 of the monitor 11 of the computer running the treatment control module 54. This embodiment would provide an accurate representation of the target tissue on the grid 200, and may eliminate the step of manually inputting the dimensions of the target tissue in order to create the target tissue on the grid 200. This embodiment would also be useful to provide an accurate representation of the target tissue if the target tissue has an irregular shape.

The basic functionality of the computer software (treatment control module 54) will now be discussed in relation to the following example. It should be noted that the software can be used independently of the generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment.

Figure 3:
FIG. 3 is a screen shot of an "Information" screen of a treatment control module showing various input boxes.

After the treatment control module 54 is initialized, it displays an "Information" screen with various input boxes as shown in FIG. 3. A keyboard or other input device 12, together with a mouse or other pointing device 14 (see FIG. 1) are used to input the data. Any data that is inputted into the input boxes can be saved into internal or external memory along with a record of the treatment as described below for future reference. The basic patient information can be inputted, such as a patient ID number in input box 100, the name of the patient in input box 101, and the age of the patient in input box 102. The user can enter clinical data, such as the clinical indication of the treatment in input box 114. The date of the procedure is automatically displayed at 111 or can be inputted by the user in another embodiment. The user can enter other case information such as the name of the physician in input box 112 and any specific case notes in input box 113.

The dimensions of the target tissue 300 are determined from viewing it on the monitor 31 of the imaging device 30 (see FIG. 1) such as an ultrasonic imaging device and using known methods to calculate the dimensions from the image generated from the imaging device 30. The dimensions of the target tissue 300 (length at input box 103, width at input box 104, and depth at input box 105) are inputted into the program. A safety margin is selected at input box 106 which will surround the entire target tissue 300 in three dimensions. According to the size of the safety margin that is selected, a target treatment region is automatically calculated and is displayed in boxes 107, 108, and 109 as shown. In one embodiment, the safety margin value may be set to zero. For example, when treating a benign tumor, a safety margin may not be necessary.

In the embodiment shown in FIG. 3, the user has indicated that the target tissue that will be treated has a length of 2 cm, width of 1 cm and a depth of 1 cm. With a user specified margin of 1 cm (which is a default margin setting), the target treatment region has a length of 4 cm, width of 3 cm and a depth of 3 cm.

Figure 38:
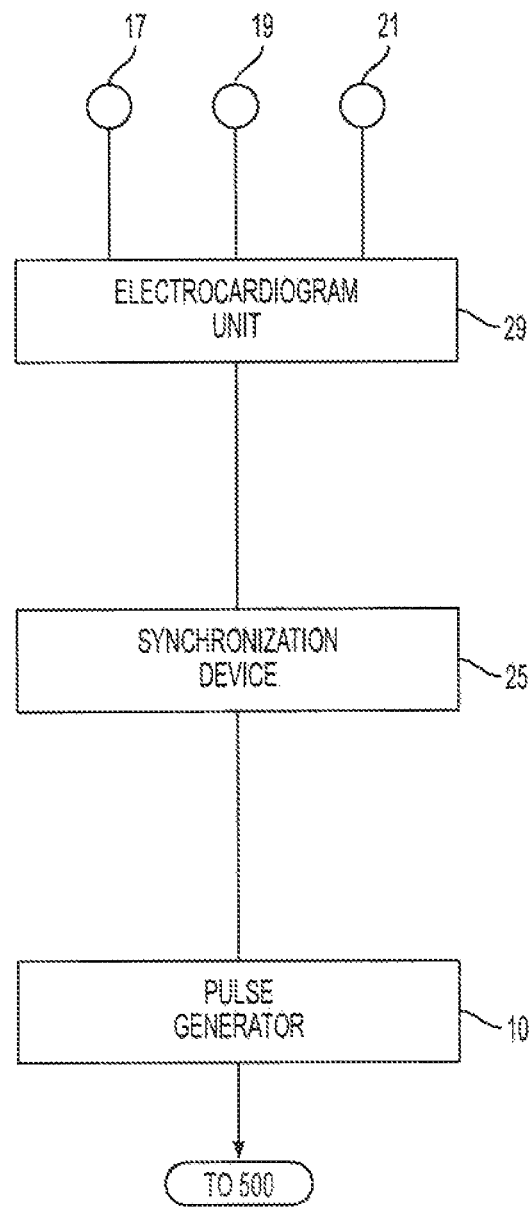
FIG. 38 illustrates a treatment setup for a patient for synchronization of the delivery of electroporation pulses with a specific portion of the cardiac rhythm.

The user can select the "ECG synchronization" option by clicking the circle in the box 110 in order to synchronize the pulses with an electrocardiogram (ECG) device, if such a device is being used during the procedure (FIG. 38). The other options available for treatment that are included in box 110 can include an option for "90 PPM" (pulses per minute) or "240 PPM". The user should select at least one of the three options provided in box 110. After all of the necessary data has been inputted, the user clicks on the "Next" button with a pointing device 14 to proceed to the next screen described below.

Further regarding the ECG synchronization option, if this circle is selected in window 110, the treatment control module 54 will test this functionality to verify that the system is working properly. The treatment control module 54 can automatically detect whether an error has occurred during the testing phase of the ECG feature. The detectable errors include, but are not limited to, "no signal" (such as no pulses for 3.5 seconds) and "noisy" (such as pulses occurring at a rate greater than 120 beats per minute for at least 3.5 seconds).

The treatment control module 54 can synchronize energy release with cardiac rhythm by analyzing cardiac output such as electrocardiogram results (or other cardiac function output) and sending synchronization signals to a controller of the pulse generator 10. The control module 54 is also capable of generating internal flags such as a synchronization problem flag and a synchronization condition flag to indicate to users on a graphic user interface a synchronization status, so that energy pulse delivery can be synchronized with the cardiac rhythm for each beat (in real-time) or aborted as necessary for patient safety and treatment efficiency.

Specifically, the control module 54 synchronizes energy pulses such as IRE (irreversible electroporation) pulses with a specific portion of the cardiac rhythm. The module uses the R-wave of the heartbeat and generates a control signal to the pulse generator 10 indicating that this portion of the heartbeat is optimal for release of IRE pulses. For clarity, the S wave would be an optimal time for delivery of an energy pulse, but due to the fact that the S wave ends nebulously in some cases, the R wave is used as an indicator to start timing of energy release.

More specifically, the synchronization feature of the control module 54 allows for monitoring of heart signals so as to ensure that changes, maladies, and other alterations associated with the heartbeat are coordinated such that pulses from the pulse generator 10 are released at the proper time, and that if the heartbeat is out of its normal rhythm, that the release of energy is either altered or aborted.

Next, the user can select the type of therapeutic energy delivery device according to the number of probes that the user believes will be necessary to produce a treatment zone which will adequately cover the target tissue 300 and any safety margin 301. The selection is made by clicking the circle next to each type of device, as shown in the "Probe Selection" screen, illustrated in FIGS. 4-9.

In one embodiment, a "Probes Selection Status" box 199 identifies which of the receptacles, if any, on the generator 10 have been connected to a probe by displaying the phrase "Connected" or the like next to the corresponding probe number. In one embodiment, each receptacle includes an RFID device and a connector (not shown) for each probe which connects to the receptacle and includes a compatible RFID device, so that the treatment control module 54 can detect whether or not an authorized probe has been connected to the receptacle on the generator 10 by detecting a connection of the compatible RFID devices. If an authorized probe is not connected to a receptacle on the generator, the phrase "Not Connected" or the like will appear next to the probe number. In addition, the colors of each probe shown in the "Probes Selection Status" box 199 can be used to indicate whether or not each receptacle on the generator is connected to a compatible probe. This feature allows the user to verify that the requisite number of probes is properly connected to the generator 10 before selecting a probe type for the treatment procedure. For example, if the treatment control module 54 detects a problem with the probe connection status (e.g. selecting a three probe array when only two probes are connected to the generator), it can notify the user by displaying an error message.

The user can select which of the connected probes will be used to perform the treatment procedure, by clicking on the box next to the selected probes in the "Probes Selection Status" box 199. By default the treatment control module 54 will automatically select probes in ascending numerical order, as they are labeled.

Referring to FIG. 4, circle 120 is used to select a bipolar probe. FIG. 4 illustrates a side view 121 and top view 122 of the bipolar probe and an example of the general shape of the treatment zone that can be generated by such a probe type. The side view 121 shows an example of the general shape of the treatment zone that can be generated by an arrangement of two electrodes 123 separated by an insulation sleeve.

Figure 5:
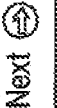
FIG. 5 is a screen shot of a "Probe Selection" screen of the treatment control module showing a side view and top view of the two probe array and an example of the general shape of the treatment zone that can be generated by a two probe array.

Referring to FIG. 5, circle 130 is used to select a two probe array. FIG. 5 illustrates a side view 131 and top view 132 of the two probe array and an example of the general shape of the treatment zone that can be generated by a two probe array. In the illustrated example, the exposed portion of each of the electrodes as shown is 20 mm in length and the two probes are spaced from each other by 15 mm.

Figure 6:
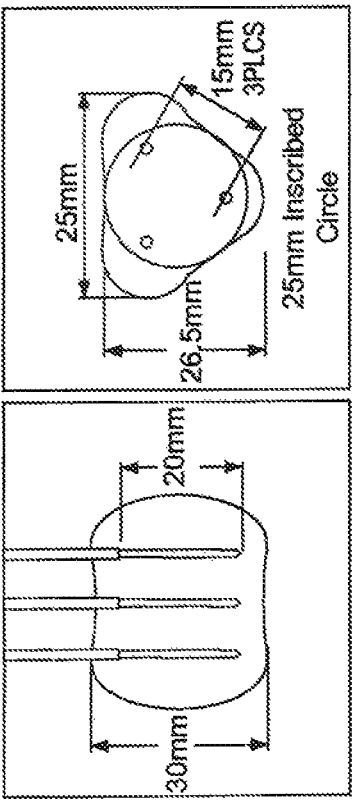
FIG. 6 is a screen shot of a "Probe Selection" screen of the treatment control module showing a side view and top view of the three probe array and an example of the general shape of the treatment zone that can be generated by a three probe array.

Referring to FIG. 6, circle 140 is used to select a three probe array. FIG. 6 illustrates a side view 141 and top view 142 of the three probe array and an example of the general shape of the treatment zone that can be generated by a three probe array. In the illustrated example, the exposed portion of each of the electrodes as shown is 20 mm in length and each pair of the three probes are equally spaced from each other by 15 mm, as measured at three places (PLCS), meaning that there are three pairs (pairs 1-2, 2-3 and 1-3) where the spacing is equal to 15 mm.

Figure 7:
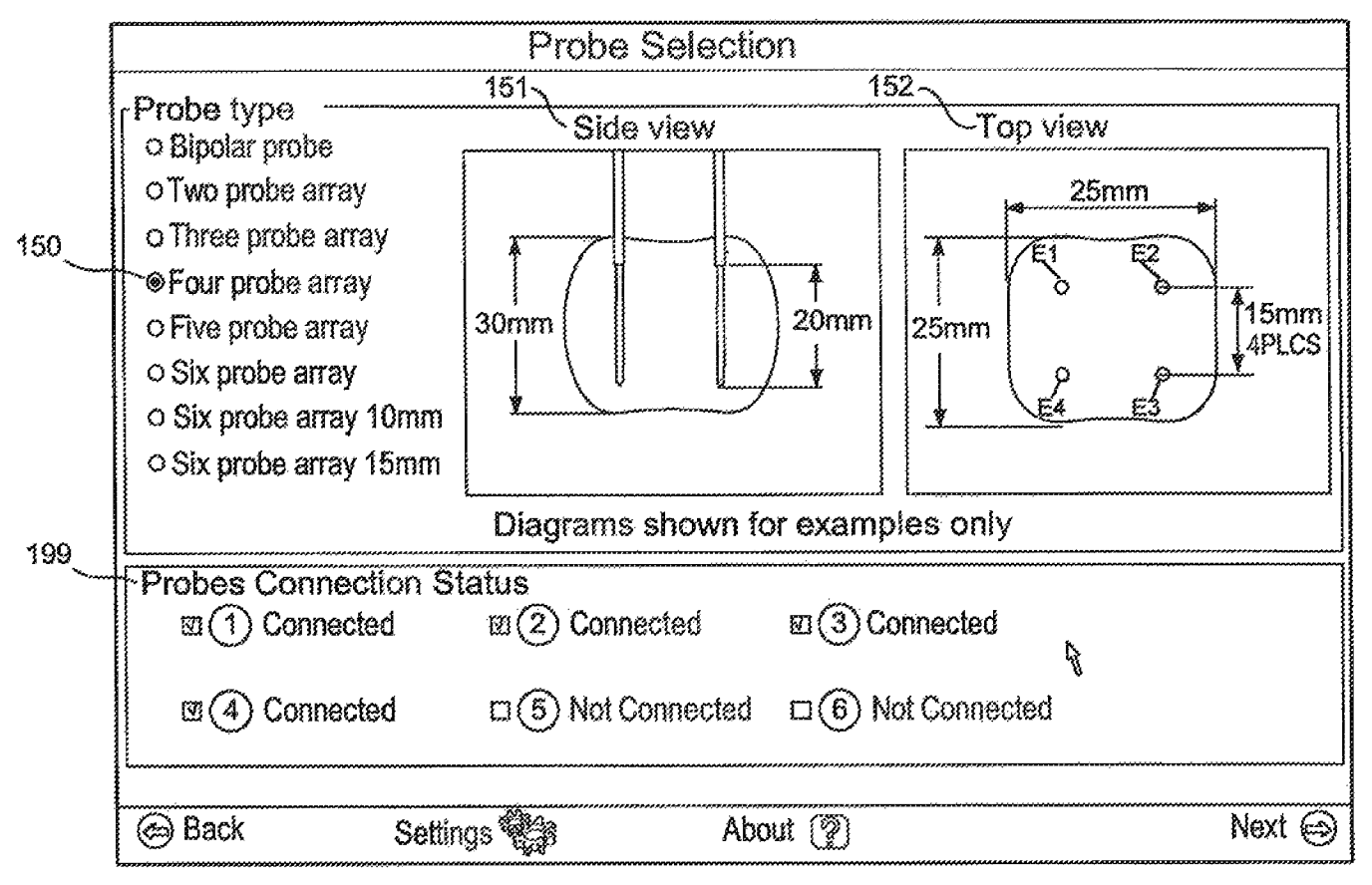

Referring to FIG. 7, circle 150 is used to select a four probe array. FIG. 7 illustrates a side view 151 and top view 152 of the four probe array and an example of the general shape of the treatment zone that can be generated by a four probe array. In the illustrated example, the exposed portion of each of the electrodes as shown is 20 mm in length and each pair of the four probes are equally spaced from each other by 15 mm, as measured at four places (PLCS) along the perimeter.

Figure 8:
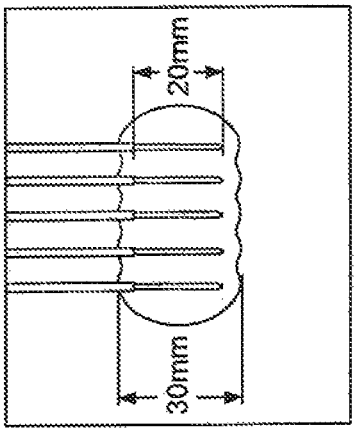
FIG. 8 is a screen shot of a "Probe Selection" screen of the treatment control module showing a side view and top view of the five probe array and an example of the general shape of the treatment zone that can generated by a five probe array.

Referring to FIG. 8, circle 160 is used to select a five probe array. FIG. 8 illustrates a side view 161 and top view 162 of the five probe array and an example of the general shape of the treatment zone that can be generated by a five probe array. In the illustrated example, the exposed portion of each of the electrodes as shown is 20 mm in length and each pair of the five probes are equally spaced from each other by 15 mm, as measured at seven places (PLCS).

Figure 9:
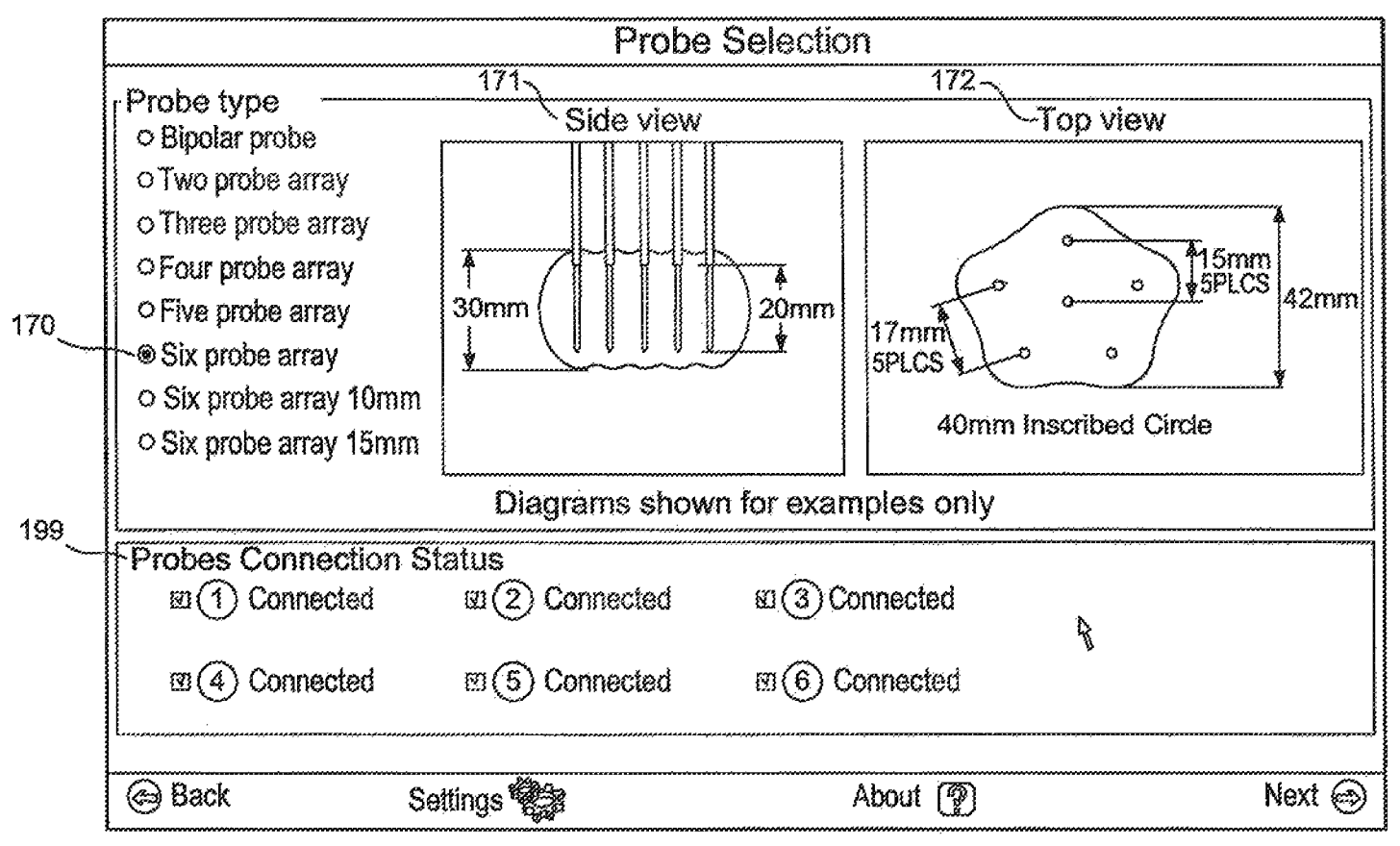

Referring to FIG. 9, circle 170 is used to select a six probe array. FIG. 9 illustrates a side view 171 and top view 172 of the six probe array and an example of the general shape of the treatment zone that can be generated by a six probe array. In the illustrated example, the exposed portion of each of the electrodes as shown is 20 mm in length and each pair of the six probes are equally spaced from each other by 15 mm, as measured at five places (PLCS) from the center probe. Each pair of the six probes are equally spaced from each other by 17 mm, as measured at 5 places (PLCS) along the perimeter.

Other probe type selection can include a "six probe array 10 mm" and "six probe array 15 mm", which refers to probe types utilizing a template which can be used to align a group of six needles in a fixed predetermined arrangement for treatment, wherein each pair of probes are equally spaced by 10 mm and 15 mm, respectively.

Other probe device types having seven or more probes can be used. The user can select a probe type having a number of probes 22 which will work most effectively to treat the specific size and shape of the target tissue 300 together with a safety margin 301.

After the user has selected a probe type on the "Probe Selection" screen, the user clicks on the "Next" button with a pointing device 14 to proceed to the "Probe Placement Process" screen described below.

Figure 10:
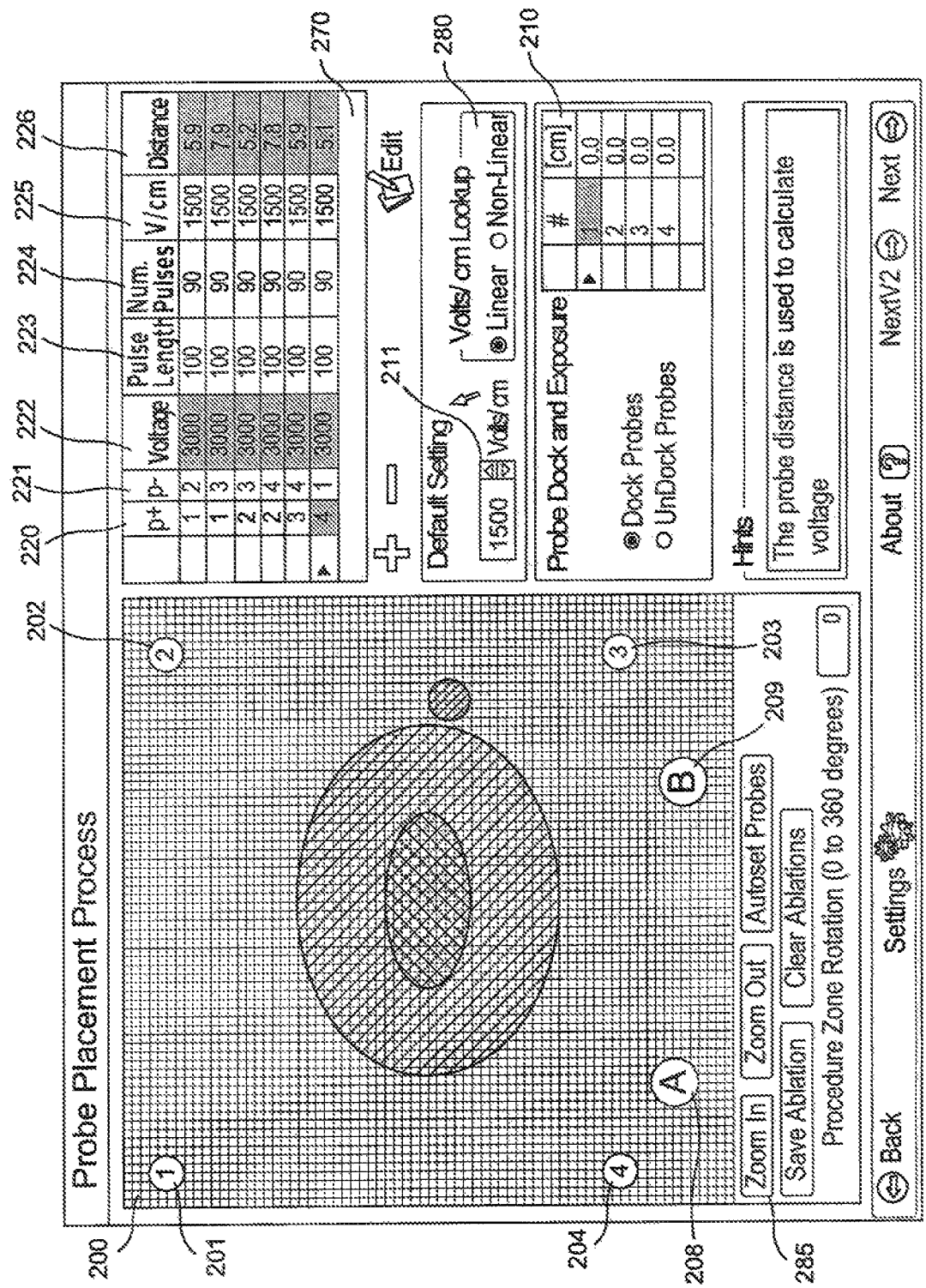
FIG. 10 is a screen shot of a "Probe Placement Process" screen of the treatment control module.

FIG. 10 illustrates a "Probe Placement Process" screen of one aspect of the invention. The screen illustrated by FIG. 10 shows a target tissue 300 according to the dimensions which were inputted on the "Information" screen (see FIG. 3) along with a safety margin 301, if any, that was previously inputted. In the example depicted in FIG. 10, the target tissue 300 has a length of 2.0 cm and a width of 1.0 cm, and the device selected on the "Probe Selection" screen (see FIGS. 4-9) is a four probe array. The target tissue 300 is displayed near the center of an x-y grid 200 with the distance between two adjacent grid lines representing 1 mm. Each of the four probes 201, 202, 203, 204 is displayed in the grid 200 and each probe can be manually positioned within the grid by clicking and dragging the probe with the pointing device 14. Two fiducials 208, 209 labeled "A" and "B", respectively, are also displayed on the grid 200 and are used as a point of reference or a measure as will be described below.

The amount of longitudinal exposure of the active electrode portion for each probe that has already been manually adjusted by the user as explained above can be manually inputted in input box 210, which can be selected by the user according to the depth (z) of the target tissue. In this way, the treatment control module 54 can generate an estimated treatment zone according to the treatment parameters, and locations and depths of the probes. In one embodiment, a second x-z grid is displayed on the monitor 11 of the computer running the treatment control module 54. In one embodiment, the treatment control module 54 can automatically calculate preferred values for the amount of longitudinal exposure of the active electrode portions based on the size and shape of the target tissue. The depth (z) of the electric field image can be calculated analytically or with interpolation and displayed on the x-z grid. Because the distribution of the electric field (i.e., expected treatment region) between two monopolar electrodes may "dip in" along the boundary line (see, for example, the peanut shaped treatment region in FIG. 13 where the width of the region is smaller in the middle) depending on the electrode location and the applied voltage, it is beneficial to have an x-z grid included on the monitor. For example, if this "dip" of the boundary line travels into, rather than surround, the target tissue region, then the targeted region may not be fully treated. As a default to ensure treatment of the entire target tissue region, the probe depth placement and the exposure length may be set unnecessarily higher to ensure erring on the safe side. However, this will potentially treat a much larger volume than needed, killing healthy surrounding tissue, which can be an issue when treating sensitive tissues such as the pancreas, brain, etc. By optimizing the treatment depth (z) together with the width (x) and height (y), this effect may be reduced, further enhancing procedural protocol and clinical outcome.

The probe dock status is indicated in box 210, by indicating if the probes are "docked" or "undocked". The "UnDock Probes" button allows the user to "unplug" the probes from the generator while the "Probe Placement Process" screen is displayed without causing error messages. In normal operation, the user plugs the probes into the generator on the "Probe Selection" screen, and then the probes are "authorized" as being compatible probes according to the RFID devices, as discussed above. When the user proceeds to the "Probe Placement Process" screen, the software requires that all the selected probes remain plugged into the generator, or else the software will display an error message (e.g. "Probe #2 unplugged", etc.), and will also force the user back to the "Probe Selection" screen. However, sometimes users may want to perform another scan of the target tissue 300 or perform some other procedure while leaving the probes inserted in the patient. But, if the procedure cannot be performed near the generator, the probes are unplugged from the generator. If the user selects the "UnDock Probes" button, this will allow the probes to be unplugged from the generator without causing an error message. Then, after the user has performed the other procedure that was required, the user can re-attach the probes to the generator, and then select "Dock Probes" in input box 210. In this way, the user will not receive any error messages while the "Probe Placement Process" screen is displayed.

There is a default electric field density setting (Volts/cm) which is shown in input box 211. In the example, the default setting is 1500 Volts/cm. This number represents the electric field density that the user believes is needed to effectively treat the cells, e.g., ablate the tissue cells. For example, 1500 Volts/cm is an electric field density that is needed to irreversibly electroporate the tissue cells. Based on the number selected in input box 211, the treatment control module 54 automatically adjusts the voltage (treatment energy level) applied between the electrodes, as shown in column 222.

Box 280 allows a user to select between two different Volts/cm types, namely "Linear" or "Non-Linear Lookup".

The default Volts/cm setting is "Linear", in which case the Voltage that is applied between a given pair of electrodes, as shown in column 222, is determined by the following formula:

$$\text{Voltage} = xd, \quad (1)$$

where x=the electric field density setting (Volts/cm) shown in column 225, which is based on the value from box 211, and where d=the distance (cm) between the given pair of electrodes shown in column 226.

Therefore, when "Linear" is selected, the Voltage that is applied between a given pair of electrodes is directly proportional to the Distance between the given electrode pair in a linear relationship.

If the user selects "Non-Linear Lookup" in box 280, then the Voltage that is applied between the given pair of electrodes will be similar to the Voltage values for a "Linear" selection when a pair of electrodes are closely spaced together (e.g. within about 1 cm). However, as a pair of given electrodes are spaced farther from one another, a "Non-Linear Lookup" will produce lower Voltages between the given pair of electrodes as compared to the Voltage values for a "Linear" selection at any given distance. The "Non-Linear Lookup" feature is particularly useful for reducing "popping" during treatment. "Popping" refers to an audible popping noise that sometimes occurs, which is believed to be caused by a plasma discharge from high voltage gradients at the tip of the electrodes. The "Non-Linear Lookup" feature can also minimize any swelling of the tissue that might occur as a result of a treatment. The Voltage values used for the "Non-Linear Lookup" selection can be pre-determined based on animal experiments and other research. In one embodiment, different tissue types can each have their own "Non-Linear Lookup" table. In the example shown, the tissue being treated is prostate tissue.

The details of the treatment parameters are displayed in window 270. The firing (switching) sequence between probes is listed automatically in window 270. In the example, the firing sequence involves six steps beginning with between probes 1 and 2, then probes 1 and 3, then probes 2 and 3, then probes 2 and 4, then probes 3 and 4, and then probes 4 and 1. As shown, the polarity of each of the probes may switch from negative to positive according to step of the firing sequence. Column 220 displays which probe is the positive probe (according to a number assigned to each probe) for each step. Column 221 displays which probe is the negative probe (according to a number assigned to each probe) for each step. Column 222 displays the actual voltage generated between each probe during each step of the firing sequence. In the example, the maximum voltage that can be generated between probes is limited by the capabilities of the generator 10, which in the example is limited to a maximum of 3000 Volts. Column 223 displays the length of each pulse that is generated between probes during each respective step of the firing sequence. In the example, the pulse length is predetermined and is the same for each respective step, and is set at 100 microseconds. Column 224 displays the number of pulses that is generated during each respective step of the firing sequence. In the example, the number of pulses is predetermined and is the same for each respective step, and is set at 90 pulses which are applied in a set of 10 pulses at a time. Column 225 displays the setting for Volts/cm according to the value selected at input box 211. Column 226 displays the actual distance between the electrodes (measured in cm), which is automatically calculated according to the placement of each probe in the grid 200.

Figure 11:
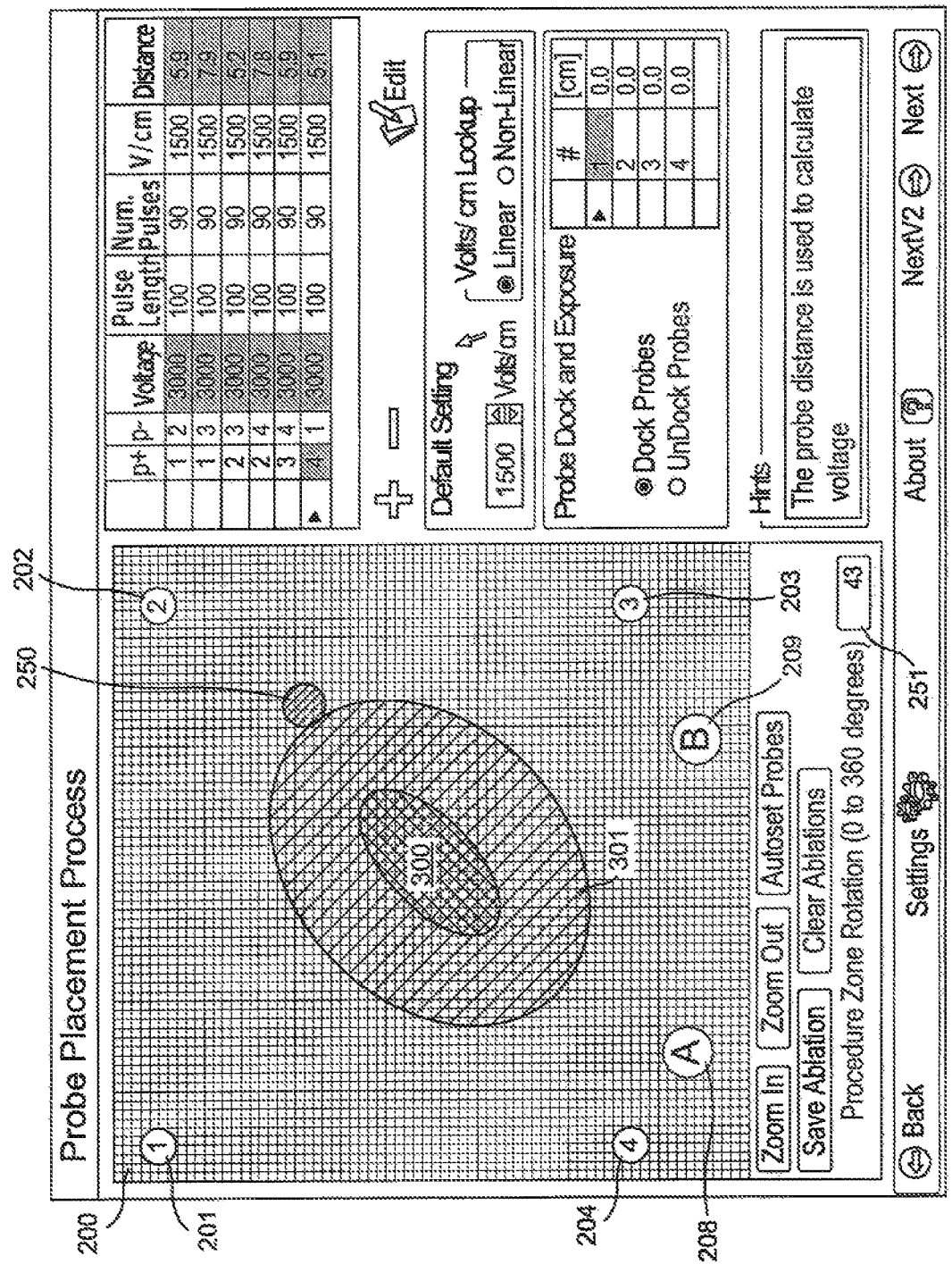
FIG. 11 is a screen shot of a "Probe Placement Process" screen of the treatment control module showing a rotation feature of the treatment control module.

FIG. 11 illustrates a rotation feature of the treatment control module 54. The user can rotate the image of target tissue 300 on the grid 200 about its center in order to approximate the actual orientation of the target tissue 300 within the body of the patient 15 (see FIG. 1), as shown by the imaging device 30. To do so, the user can view the actual orientation of the target tissue 300 within the body of the patient 15 by viewing the monitor 31 of the imaging device 30 shown in FIG. 1. While viewing, the user can rotate the target tissue 300 on the grid 200 in order to match the orientation of the target tissue 300 shown on the monitor 31 of the imaging device 30. There are at least three ways to rotate the target tissue 300 on the grid 200. The user can click on a tab 250 (to select the tab) with a pointing device 14 and drag the tab 250 to a new location which will rotate the target tissue 300. The user can alternatively click on any part of the safety margin 301 or the target tissue 300 and drag it to rotate the target tissue 300. Alternatively, the user can manually input the treatment zone rotation angle in input box 251, which represents the degree of rotation of the target tissue 300 measured from the horizontal "x" axis on the grid 200.

Figure 12:
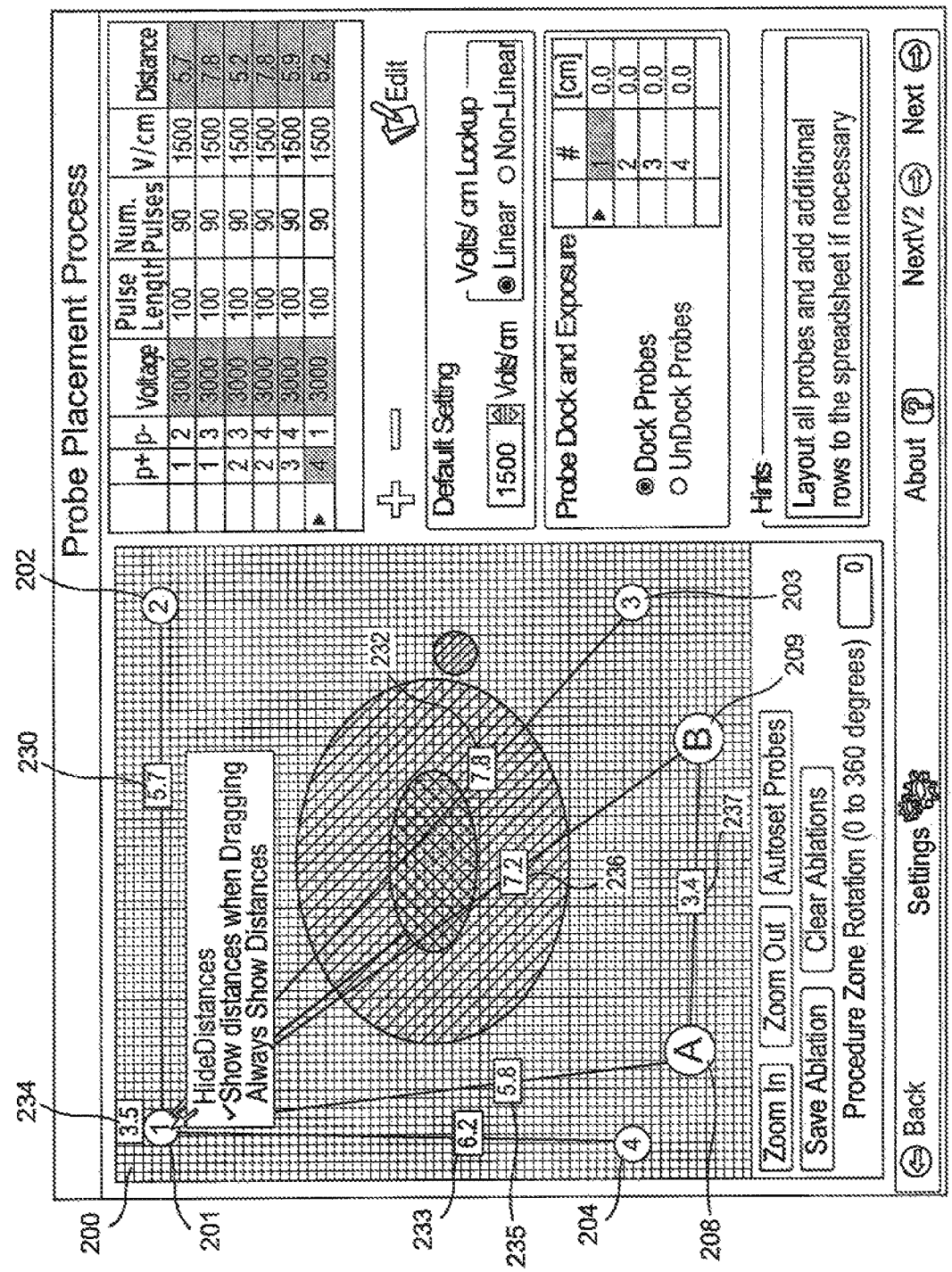
FIG. 12 is a screen shot of a "Probe Placement Process" screen of the treatment control module showing an automatic measurement feature of the treatment control module.

FIG. 12 illustrates an automatic measurement feature of the treatment control module 54. When the user clicks on a probe and drags it with the pointing device 14, the treatment control module 54 automatically and continuously displays the distance (cm) from that electrode 201 to each of the other electrodes 202 (distance displayed in box 230), 203 (distance displayed in box 232), 204 (distance displayed in box 233) as the probe is being dragged. The treatment control module 54 also displays the distance (cm) from that electrode 201 to the closest point on the outer surface of the target tissue 300 (distance displayed in box 234). The treatment control module 54 also displays the distance (cm) from that electrode 201 to fiducial "A" 208 (distance displayed in box 235), fiducial "B" 209 (distance displayed in box 236). The treatment control module 54 also displays the distance (cm) from fiducial "A" 208 to fiducial "B" 209 with the distance being displayed in box 237. This feature assists the user in placing the electrodes in preferred locations. This feature is especially beneficial if the imaging device 30 (see FIG. 1) allows the calculation of measurements as is known in the art.

Figure 13:
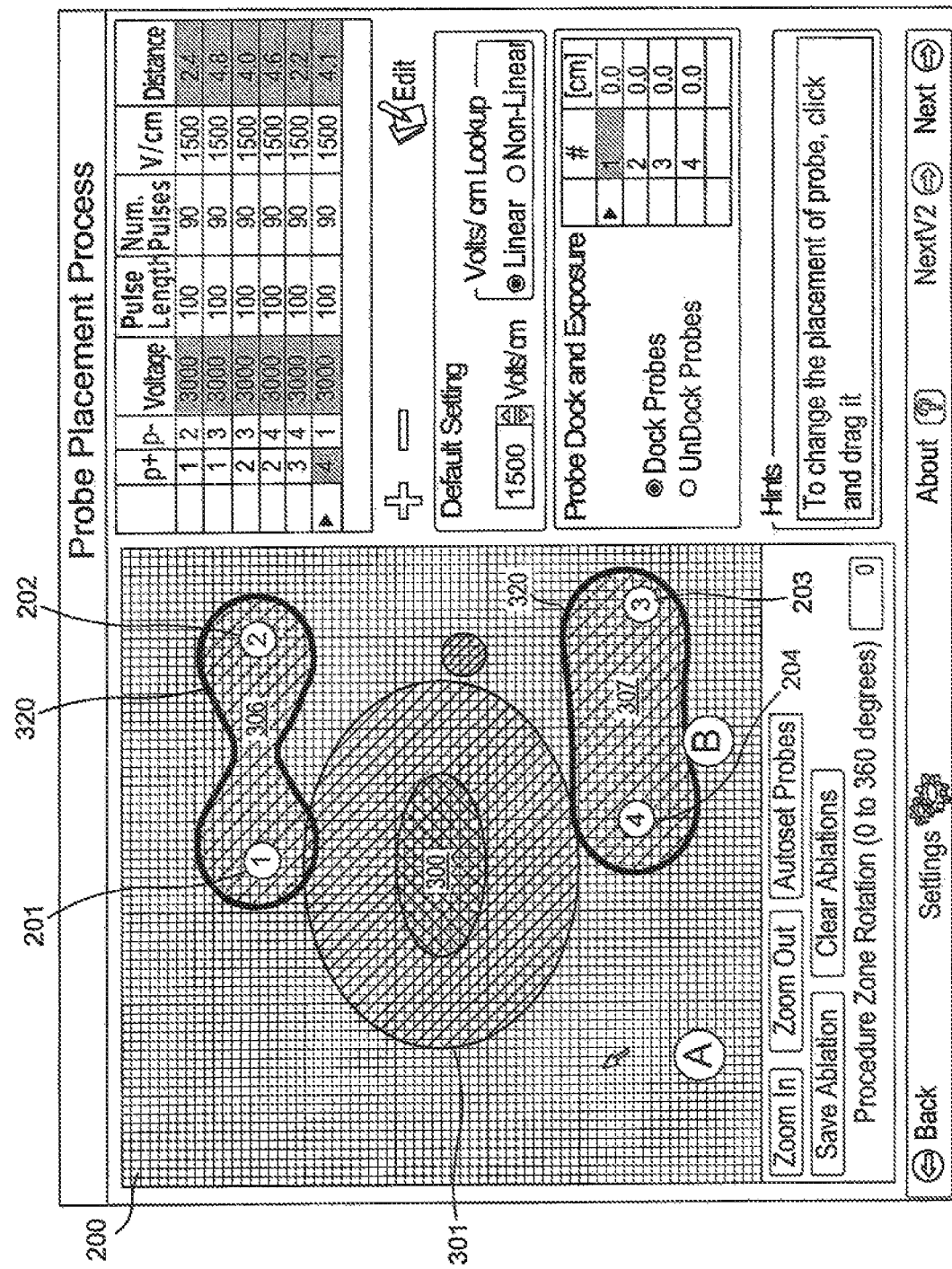
FIG. 13 is a screen shot of a "Probe Placement Process" screen of the treatment control module showing examples of treatment zones that can be created between the electrodes.

FIG. 13 illustrates examples of the treatment zones that are automatically created between the electrodes by the treatment control module 54. The treatment control module 54 automatically calculates the treatment zones which are created and displays the area of the treatment zone. In a preferred embodiment, the monitor 11 of the generator 10 is in color and the color of the treatment zones 306, 307, the target tissue 300, and the safety margin 301 are all different to easily differentiate them from one another. In one embodiment, the target tissue 300 is yellow and the safety margin 301 is blue. In addition, the treatment control module 54 can be programmed to adjust the color of the target tissue 300 and/or the boundary line of the target tissue 300 if the treatment zones 306, 307 do not effectively cover the target tissue, which could otherwise result in a clinical failure.

Figure 14:
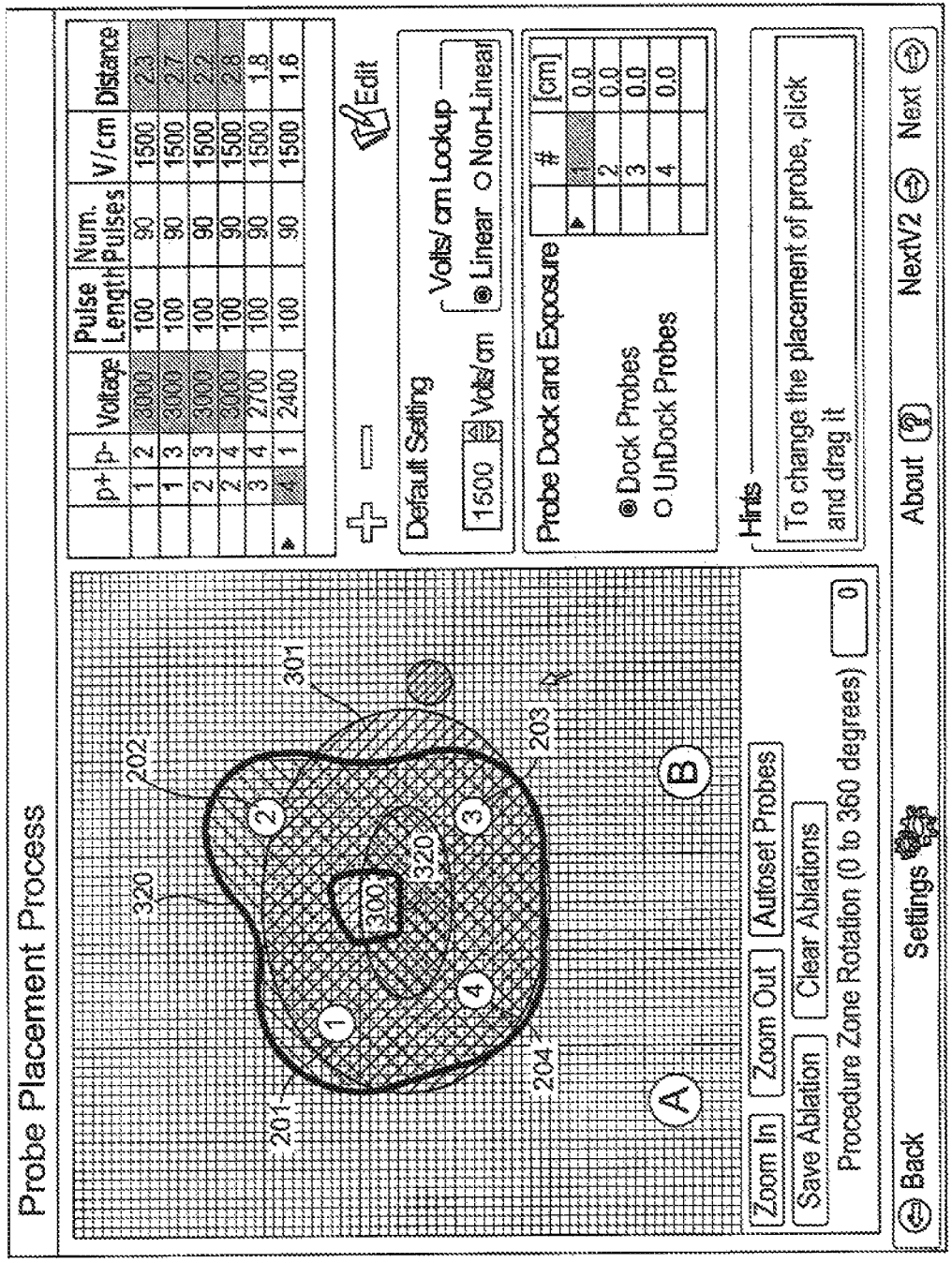
FIG. 14 is a screen shot of a "Probe Placement Process" screen of the treatment control module showing an example of a combined treatment zone generated by a four probe array.

In addition, the treatment control module 54 can be programmed to display a boundary line 320 that surrounds the areas of the treatment zones 306, 307 in a highlighted manner so that the outer boundaries of the treatment zones are readily identifiable. In one embodiment, the boundary line is a black line having sufficient thickness to provide a sharp contrast against the displayed target tissue and the grid. FIG. 14 illustrates a combined treatment region that is created by a four probe array 201, 202, 203, 204. The control module 54 displays a boundary line 320 to identify the outer boundary of the combined treatment zone. The control module 54 also displays a boundary line 320 to identify one or more inner boundaries of the combined treatment zone, if applicable. This allows the user to easily identify the presence of any incomplete treatment coverage areas of the target tissue 300. The inner boundary line 320 is especially useful to identify incomplete treatment areas that may have not otherwise been readily detectable on the computer screen. Since even a few surviving infectious cells can be detrimental in terms of recurrence of infection, this feature is especially important when treating an area with an implanted medical device having infectious cells.

The treatment control module can be programmed to calculate and display the area of the combined treatment regions on the grid 200 by one of the following three methods, although other methods can be used.

Each of the following methods determines a boundary line surrounding a treatment zone that is created between a pair of electrodes. By combining a plurality of treatment zones with each treatment zone being defined by a pair of electrodes, a combined treatment region can be displayed on the x-y grid. FIG. 15 illustrates three electrodes 201, 202, 203 defining three individual treatment zones 311, 312, 313, which combine to form a combined treatment region 315 which is shown with hatched lines.

As discussed above, the monitor can further include an x-z grid to illustrate the depth of the target tissue and the shape of treatment region. The shape of the treatment zone in the x-z grid will vary according to the selected amounts of electrode exposure for each probe and can be determined by one or more methods.

In one embodiment, the treatment boundary line that is created between two points on the x-y grid can be rotated about an axis joining the two points in order to generate the treatment region boundary line on the x-z grid. In this embodiment, several points may be selected along the exposed length of the active electrode portion for each probe at various depths (z). A three-dimensional combined treatment region can then be generated by determining the boundary line on the x-y grid between each individual pair of points and then rotating the boundary line along the axis joining each pair of points. The resulting boundary lines can be combined to create a three dimensional image that is displayed on the monitor.

The following is an alternate method for determining a boundary line on the x-z grid, thereby determining a three dimensional treatment region. This example describes a two probe array with the probes being inserted in a parallel relationship and with the probes having the same amount of exposed portions of the electrode. In this example, the exposed portions of each probe start at the same "uppermost" depth (z) and end at the same "lowermost" depth (z). First, a treatment zone boundary line is created in the x-y plane at the uppermost depth (z). Next, the treatment zone boundary line is repeatedly created stepwise for all subsequently lower depths (z), preferably evenly spaced, until the lowermost depth (z) is reached. The result is a 3-D volume (stacked set of treatment zone boundary lines) having a flat top surface and a flat bottom surface. Next, two new focus points are selected, with the first focus point positioned midway between the probe positions in the x-y grid and near the uppermost depth (z) of the exposed electrode. The second focus point is also positioned midway between the probe positions in the x-y grid, but near the lowermost depth (z) of the exposed electrode. Next, a treatment zone boundary line is created in the x-z grid using one of the methods described earlier. The actual placement of each focus point may be closer together, namely, not positioned in the uppermost and lowermost x-y planes defined by the exposed portions. The placement of each focus point should be selected so that the treatment zone boundary line that is created in the x-z grid closely matches the treatment zone boundary lines that were created in the uppermost and lowermost x-y grids. Next, the treatment zone boundary line that was created in the x-z grid according to the two focus points is rotated about the axis joining the two focus points. This creates the shapes for the upper and lower 3-D volumes which are added to the flat top surface and the flat bottom surface described above.

The above methods can be applied by persons of ordinary skill in the art to create 3-D treatment zones between exposed portions of electrodes even when the probes are not parallel to each other and even when the amount of the exposed portion varies with each probe.

Furthermore, there are situations where it is advantageous to show multiple boundary zones as a result of a therapy. For example, indicating which regimes undergo no change, reversible electroporation, irreversible electroporation, and conventional thermal damage is possible in accordance with the present invention. In addition, it is possible to output the entire distribution rather than just delineating boundaries. For example, the "Second Method" (as discussed below) can be used to determine the entire potential field or temperature distribution within the domain.

It has been shown repeatedly in the literature that tissue properties are highly variable between tissue types, between individuals, and even within an individual. These changes may result from differences in body fat composition, hydration levels, and hormone cycles. Due to the large dependence of IRE (irreversible electroporation) treatments on tissue conductivity, it is imperative to have accurate values. Therefore, to obtain viable conductivity values prior to treatment, a low amplitude voltage pulse is used between the electrode conductors and the resultant impedance/conductance is measured as a way to determine pertinent tissue property data such as the predicted current. The value determined may then be implemented when assessing field strength and treatment protocol in real time. For example, the resulting impedance or predicted current can be used to set the default electric field density.

As discussed in the background, one accurate numerical model based method for generating a treatment zone between a pair of treatment probes involves finite element analysis (FEA). For example, U.S. Patent Application Publication No. 2007/0043345, which is hereby incorporated by reference, discloses using FEA models to generate treatment zones between a pair of electrodes (the calculations were performed using MATLAB's finite element solver, Femlab v2.2 (The MathWorks, Inc. Natick, Mass.)).

Most engineering problems can be solved by breaking the system into cells where each corner of the cell or mesh is a node. FEA is used to relate each node to each of the other nodes by applying sets of partial differential equations. This type of a system can be coded by scratch, but most people use one of many commercial FEA programs that automatically define the mesh and create the equations given the model geometry and boundary conditions. Some FEA programs only work in one area of engineering, for example, heat transfer and others are known as multiphysics. These systems can convert electricity to heat and can be used for studying the relationships between different types of energy.

Typically the FEA mesh is not homogeneous and areas of transition have increased mesh density. The time and resources (memory) required to solve the FEA problem are proportional to the number of nodes, so it is generally unwise to have a uniformly small mesh over the entire model. If possible, FEA users also try to limit the analysis to 2D problems and/or use planes of symmetry to limit the size of the model being considered because even a modest 2D model often requires 30 minutes to several hours to run. By comparison, a 3D Model usually takes several hours to several days to run. A complicated model like a weather system or a crash simulation may take a super computer several days to complete.

Depending on the complexity of the FEA models that are required, the purchase price of the FEA modeling software can cost several thousand dollars for a low end system to $30 k for a non-linear multiphysics system. The systems that model the weather are custom made and cost tens of millions of dollars.

In one example, the steps which are required for generating a treatment zone between a pair of treatment probes using finite element analysis include: (1) creating the geometry of interest (e.g., a plane of tissue with two circular electrodes); (2) defining the materials involved (e.g., tissue, metal); (3) defining the boundary conditions (e.g., Initial voltage, Initial temperature); (4) defining the system load (e.g., change the voltage of the electrodes to 3,000V); (5) determining the type of solver that will be used; (6) determining whether to use a time response or steady state solution; (7) running the model and wait for the analysis to finish; and (8) graphing the results.

As discussed above, using FEA is not at all practical for use in calculating and displaying a treatment zone that is created between a pair of treatment probes in accordance with the present invention because of the time required to run these types of analyses. For the present invention, the system should allow a user to experiment with probe placement and should calculate a new treatment zone in less than a few seconds. Accordingly, the FEA model is not appropriate for such use and it would be desirable to find an analytic solution (closed form solution), which can calculate the treatment zones with only simple equations, but which closely approximate the solutions from a numerical model analysis such as the finite element analysis. The closed loop solutions should preferably generate the treatment zone calculation in a fraction of a second so as to allows a physician/user to experiment with probe placement in real time.

According to the present invention, there are several closed loop (analytical model analysis) methods for estimating and displaying a treatment zone between a pair of treatment probes, which produce similar results to what would have been derived by a numerical model analysis such as FEA, but without the expense and time of performing FEA. Analytical models are mathematical models that have a closed form solution, i.e., the solution to the equations used to describe changes in a system can be expressed as a mathematical analytic function. The following three methods represent non-limiting examples of such alternative closed loop solutions.

The First Method

In mathematics, a Cassini oval is a set (or locus) of points in the plane such that each point p on the oval bears a special relation to two other, fixed points $q_1$ and $q_2$: the product of the distance from p to $q_1$ and the distance from p to $q_2$ is constant. That is, if the function dist(x,y) is defined to be the distance from a point x to a point y, then all points p on a Cassini oval satisfy the equation:

$$\text{dist}(q_1,p) \times \text{dist}(q_2,p) = b^2 \qquad (2)$$

where b is a constant.

The points $q_1$ and $q_2$ are called the foci of the oval.

Suppose $q_1$ is the point (a,0), and $q_2$ is the point (−a,0). Then the points on the curve satisfy the equation:

$$((x-a)^2+y^2)((x+a)^2+y^2) = b^4 \qquad (3)$$

The equivalent polar equation is:

$$r^4 - 2a^2 r^2 \cos 2\theta = b^4 - a^4 \qquad (4)$$

The shape of the oval depends on the ratio b/a. When b/a is greater than 1, the locus is a single, connected loop. When b/a is less than 1, the locus comprises two disconnected loops. When b/a is equal to 1, the locus is a lemniscate of Bernoulli.

The Cassini equation provides a very efficient algorithm for plotting the boundary line of the treatment zone that was created between two probes on the grid 200. By taking pairs of probes for each firing sequence, the first probe is set as $q_1$ being the point (a,0) and the second probe is set as $q_2$ being the point (−a,0).

The polar equation for the Cassini curve was used because it provides a more efficient equation for computation. The current algorithm can work equally as well by using the Cartesian equation of the Cassini curve. By solving for $r^2$ from eq. (4) above, the following polar equation was developed:

$$r^2 = a^2 \cos(2*\text{theta}) +/- \text{sqrt}(b^4 - a^4 \sin^2(2*\text{theta})) \qquad (5)$$

where a=the distance from the origin (0,0) to each probe in cm; and where b is calculated from the following equation:

$$b^2 = \left[\frac{V}{[\ln(a)(595.28) + 2339]\left(\frac{A}{650}\right)}\right]^2 \quad (6)$$

where V=the Voltage (V) applied between the probes;
where a=the same a from eq. (5); and
where A=the electric field density (V/cm) that is required to ablate the desired type of tissue according to known scientific values.

As can be seen from the mathematics involved in the equation, r can be up to four separate values for each given value for theta.

Example 1

If V=2495 Volts; a=0.7 cm; and A=650 V/cm;
Then $b^2$=1.376377
and then a cassini curve can be plotted by using eq. (5) above by solving for r, for each degree of theta from 0 degrees to 360 degrees.

A portion of the solutions for eq. (5) are shown in Table 1 below:
where M=$a^2$ cos(2*theta); and L=sqrt($b^4$−$a^4$ $\sin^2$(2*theta))

TABLE 1

| Theta (degrees) | r = sqrt (M + L) | r = −sqrt (M + L) | r = sqrt (M − L) | r = −sqrt (M − L) |
|---|---|---|---|---|
| 0 | 1.366154 | −1.36615 | 0 | 0 |
| 1 | 1.366006 | −1.36601 | 0 | 0 |
| 2 | 1.365562 | −1.36556 | 0 | 0 |
| 3 | 1.364822 | −1.36482 | 0 | 0 |
| 4 | 1.363788 | −1.36379 | 0 | 0 |
| 5 | 1.362461 | −1.36246 | 0 | 0 |
| 6 | 1.360843 | −1.36084 | 0 | 0 |
| 7 | 1.358936 | −1.35894 | 0 | 0 |
| 8 | 1.356743 | −1.35674 | 0 | 0 |
| 9 | 1.354267 | −1.35427 | 0 | 0 |
| 10 | 1.351512 | −1.35151 | 0 | 0 |
| 11 | 1.348481 | −1.34848 | 0 | 0 |
| 12 | 1.34518 | −1.34518 | 0 | 0 |
| 13 | 1.341611 | −1.34161 | 0 | 0 |
| 14 | 1.337782 | −1.33778 | 0 | 0 |
| 15 | 1.333697 | −1.3337 | 0 | 0 |

The above eq. (6) was developed according to the following analysis.

The curve from the cassini oval equation was calibrated as best as possible to the 650 V/cm contour line using two 1-mm diameter electrodes with an electrode spacing between 0.5-5 cm and an arbitrary applied voltage.

For this worksheet, $q_1$ and $q_2$ reference points (taken to be +/− electrodes) could be moved to locations along the x-axis to points of (±a,0). A voltage could then be selected, and an arbitrary scaling factor ("gain denominator") would convert this voltage to the corresponding "b" used in eq. (4). The worksheet would then plot the resulting Cassini oval, which has a shape progression with applied voltage beginning as two circles around the electrodes that grow into irregular ellipses before converging into a single "peanut" shape that ultimately becomes an ellipse expanding from the original electrode locations.

The Cassini oval creates a reasonable visualization that mimics the shape of numerical results for the field distribution. In order to understand which values or levels correspond to a desired electric field of interest, a calibration involving the $b^4$ term was necessary to develop the relationship between the analytical Cassini oval and the numerical results. This was done through a backwards calibration process defined as follows:

1. A reference contour was selected to correlate the analytical and numerical solutions. This was chosen to be when b/a=1, forming a lemniscate of Bernoulli (the point where the two ellipses first connect, forming "∞").

2. A reference electric field density value was selected to be 650 V/cm

3. Numerical models were developed to mimic the x-y output from the Cassini oval for scenarios where a=±0.25, 0.5, 0.75, 1.0, 1.25, 1.5, 1.75, 2.0, 2.25, and 2.5 cm.

4. Models were solved using trial and error to determine which voltage yielded the electric field contour of 650 V/cm in the shape of a lemniscate of Bernoulli 5. The determined voltage was placed into the Cassini oval electronic worksheet for the same electrode geometry and the "gain denominator" was adjusted until the shape from the cassini oval matched that from the numerical solution.

6. The determined gain denominators for all values of "a" were collected and a calibration plot was made and fitted with a logarithmic trendline of:

Gain Denominator=595.28·ln($a$)+2339;$R^2$=0.993 (7)

7. The calibration trendline function shown above was incorporated back into the Cassini Oval spreadsheet. At this point, the worksheet was capable of outputting a field contour of 650 V/cm for any electrode separation distance (±a) and applied voltage (V).

8. The calibration function was then scaled to a desired electric field contour input. This allowed the analytical solution to solve for any electric field for any given a separation distance and voltage. Since the Laplace equation is linear, scaling should provide a good estimate for how other fields would look.

Table 1 incorporates all the steps above to yield a single, calibrated Cassini Oval output that analytically predicts the electric field distribution; providing a quick and simple solution for the prediction of IRE (irreversible electroporation) treatment regions that may be adjusted in real-time. The inputs are the electrode location (as a given "±a" distance from the origin along the x-axis), the applied voltage to the energized electrode, and the desired electric field to visualize. The resulting output is a contour representing a threshold where the entire area within it has been subjected to an electric field≥the one selected; and thus treated by IRE. It is important to remember that the analytical solution was calibrated for an electric field contour of 650 V/cm, and thus yields an accurate approximation for this value. Other field strength contours of interest still yield reasonable results that mimic the overall shape of the electric field. Overall, the analytical solution provided yields consistently good predictions for electric field strengths, and thus, treatment regions of IRE that may be used during treatment planning or analysis.

A similar algorithm for calibration has also been used for a bipolar electrode and the electric field contour has been mapped its length. For example, FIG. 4 illustrates an exemplary bipolar electrode.

In one example, the diameter of the probe is 0.065 cm, and the lengths of the two electrodes are respectively 0.295 cm and 0.276 cm, separated by an insulation sleeve of 0.315 cm in length. Adapting this scenario to the cassini oval presents some challenges because the distribution is now resulting from the two exposed cylinder lengths, rather than two distinct loci of points. This was solved by calibrating individual electric field contours for the same applied voltage and developing two equations that adjust the separation distance (±a) and gain denominator (GD) according to the equations:

$$a = 7*10^{-9}*E^3 - 2*10^{-5}*E^2 + 0.015*E + 6.1619;$$
$$R^2 = 0.9806 \quad (8)$$

$$GD = 1.0121*E + 1920; R^2 = 0.9928 \quad (9)$$

where E is the electric field magnitude contour desired. These two equations may then be used to calibrate the cassini ovals into a satisfactory shape to mimic the electric field distribution, and thus treatment region accordingly.

The Second Method

Another closed loop method determines the E-field values (electric field density) for any x and y position on the grid based on the position of the probes, the diameter of the probes, and the voltage applied between the probes. To obtain the potential, temperature or field distribution, one can determine the analytical solution for a configuration.

Since the solution to the Laplace Equation is linear, analytical solutions can be scaled and super-imposed to determine the entire distribution. For example, if two electrodes are energized and two electrodes are set to ground, the solution can be determined by adding the solutions for the two-needle electrode configuration together.

For example, for a two-needle electrode configuration, the solution is an infinite series. This can be approximated using the following equation:

$$E = \frac{V_0}{2*\log(d/a)}\left(\frac{1}{|\underline{r} - \underline{r_1}|} + \frac{1}{|\underline{r} - \underline{r_2}|}\right) \quad (10)$$

where, $$d = \sqrt{(x_2 - x_1)^2 + (y_2 - y_1)^2} \quad (11)$$

$$|\underline{r} - \underline{r_1}| = \sqrt{(x - x_1)^2 + (y - y_1)^2} \quad (12)$$

$$|\underline{r} - \underline{r_2}| = \sqrt{(x - x_2)^2 + (y - y_2)^2} \quad (13)$$

$V_o$=the applied Voltage (V) between the probes
a=diameter of each of the probes in meters
d=distance between the probes in meters
$(x_1, y_1)$=the position of the first probe
$(x_2, y_2)$=the position of the second probe The user can then select a contour line in V/cm (i.e. 650 V/cm) based on the type of tissue which is being treated. This contour line can be used to therefore plot a boundary line of the treatment zone between two probes.

Example 2

$(x_1, y_1) = (-0.005 \text{ m}, 0 \text{ m})$
$(x_2, y_2) = (0.001 \text{ m}, 0.003 \text{ m})$
$V_o = 1000V$
a=0.0010 m
d=0.006708 m Using eqs. (10-13) above, the E-field values are determined for x, y coordinates on the grid, as shown in the spreadsheet at FIG. 16.

This method can also be used to determine the E-field values for devices having two plate electrodes or two concentric cylinders.

The Third Method

As an alternate method of estimating the treatment zone in real time, a predetermined set of values that define the outer boundary of a plurality of predetermined treatment zones (determined by FEA, one of the above two methods or the like) can be stored in memory as a data table and interpolation can be used to generate an actual treatment zone for a particular treatment area (e.g., tumor area).

Interpolation is commonly used to determine values that are between values in a look up table. For example if a value half way between 5 and 10 in the first row of the lookup table (see Table 3 below) needs to be determined, a single interpolation (average of 5 and 10) is done to obtain 7.5. If a value between 15, 20, 25, and 30 needs to be determined, a double interpolation is done. A first interpolation is done between 15 and 20 to obtain 17.5 and between 25 and 30 to obtain 27.5. Then, a second interpolation is done between 17.5 and 27.5 to obtain 22.5.

TABLE 3

| 1  | 5  | 7.5  | 10 |
|----|----|------|----|
| 11 | 15 | 17.5 | 20 |
|    |    | 22.5 |    |
| 21 | 25 | 27.5 | 30 |

It is to be noted that the interpolation is not limited to finding the mid point between two points. Interpolation can be done on any point between two points. For example, interpolation can be done at 15% (i.e., 15% away from one point and 85% away from the other point) and 75% (i.e., 75% away from one point and 25% away from the other point).

Numerical techniques, such as Finite Element Analysis (FEA) which was described above, Finite Difference Methods, or Boundary Element Methods can be used to generate shapes that take into account multiple variables (applied voltage, electrode separation, desired field boundary, tissue specific constants, and the like). These shapes can be stored in a multidimensional array (i.e., a multi-dimensional lookup table) in either polar or Cartesian coordinates. When a specific treatment situation occurs, an interpolation between the known shapes as represented by the lookup table can be used to generate an estimate of an estimated treatment zone.

Figure 17:
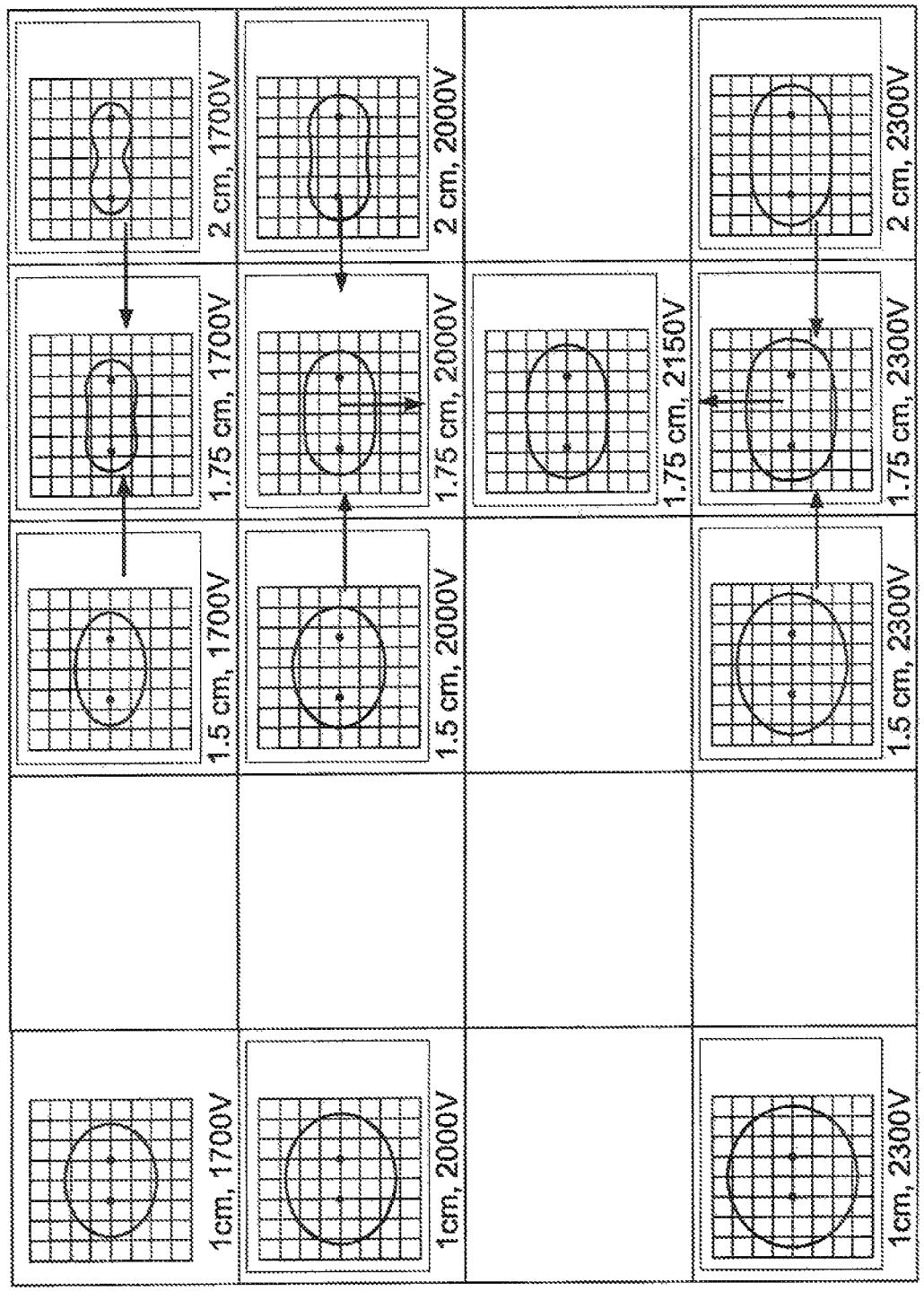
FIG. 17 illustrates an example of a multi-dimensional lookup table and a method of interpolating treatment zones.

For example, FIG. 17 illustrates a multi-dimensional lookup table and a method of interpolating treatment zones. The multi-dimensional lookup table includes for each predetermined treatment zone a table or array of points that represent a particular treatment zone. For example, the top left corner of FIG. 17 illustrates a lookup table for a predetermined treatment zone for 1 cm radius tumor area at 1700 Volts/cm electric field density for a pair of electrodes.

To treat a 1.75 cm radius tumor area at 1700 Volts/cm electric field density, the contour of the treatment zone is estimated by interpolating between two nearby zones (i.e., one for 1.5 cm radius tumor area at 1700 Volts and one for 2.0 cm radius tumor area at 1700 Volts).

To treat a 1.75 cm radius tumor area at 2150 Volts/cm electric field density, the contour of the treatment zone is estimated by double interpolation. First, the treatment zones for 1.75 cm, 2000 Volts and 0.175 cm at 2300 Volts are determined. Then, the treatment zone for 1.75 cm at 2150

Volts is determined based on the interpolation results (i.e., estimated zone for 1.75 cm at 2000 Volts and estimated zone for 1.75 cm at 2300 Volts).

Automatic Probe Placement Feature

Figure 18:
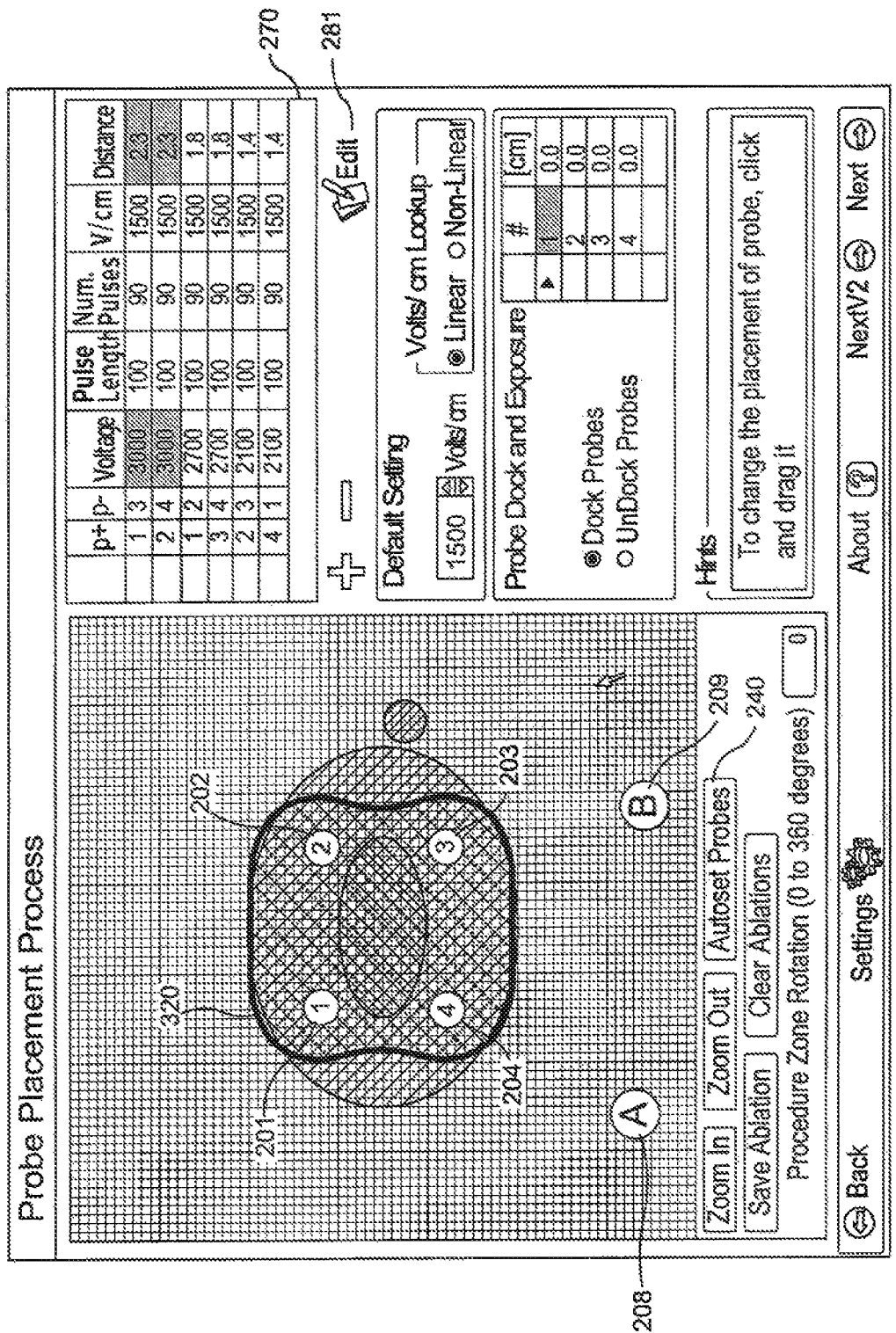
FIG. 18 is a screen shot of a "Probe Placement Process" screen of the treatment control module showing an automatic probe placement feature of the treatment control module.

Now referring to FIG. 18, this figure illustrates an automatic probe placement feature of the treatment control module 54. If the user clicks on the "Autoset Probes" button 240 with the pointing device 14, the treatment control module 54 will automatically position the probes 201, 202, 203, 204 in the most efficient way in order to treat the target tissue 300. FIG. 18 illustrates the position of the probes 201, 202, 203, 204 after the "Autoset Probes" button 240 has been depressed with the pointing device 14.

The automatic placement feature of the treatment control module 54 is further discussed below. This feature is carried out by the following algorithm. The algorithm functions to most efficiently place a given number of probes, which is based on the type of device which is selected in FIGS. 4-9 as discussed above (ranging from 2 to 6 probes) in an optimal pattern to cover the defined treatment area (i.e., the combined target tissue 300 and the safety margin 301). The algorithm assumes that the combined target tissue 300 and safety margin 301 form a generally elliptical shape. This elliptical shape is determined from the dimensions of the target tissue zone (length and width), together with the desired safety margin which were inputted by the user (see FIG. 3).

The algorithm uses the following formulas to calculate the most efficient placement of each of the probes on the grid 200. The algorithm calculates the $(x_i, y_i)$ location of each probe i on the grid 200, relative to (0,0) origin, using the following two formulas:

$$x_i = \varepsilon_j * a * \cos(\theta_i + \varphi) \quad (14)$$

$$y_i = \varepsilon_j * b * \sin(\theta_i + \varphi), \quad (15)$$

where, a=the major axis of the elliptical shape (cm) that is selected at FIG. 3;

b=the minor axis of the elliptical shape (cm) that is selected at FIG. 3; and;

$\varphi$=the rotational angle (degrees) of the ellipse as shown on treatment screen (see input box 251 at FIG. 11)

$\theta_i$=the angular offset (degrees) for each probe according to Table 2.1 below:

TABLE 2.1

| Total number of probes in the device | Angular Offsets ($\theta_i$) for each probe, referenced from zero degrees (positive x-axis) of the grid |
|---|---|
| 2 probes | 0° and 180° |
| 3 probes | 90°, 210°, and 330° |
| 4 probes | 45°, 135°, 225°, and 315° |
| 5 probes | 90°, 162°, 234°, 306°, and 18° |
| 6 probes | 90°, 162°, 234°, 306°, and 18° PLUS the 6$^{th}$ probe at the center of the grid (0,0) |

$\varepsilon_j$=the ratio of (the probe placement radius) to (the total radius to the edges of the target tissue), according Table 2.2 below:

TABLE 2.2

| Total number of probes in the device | Probe placement ratios ($\varepsilon_j$) |
|---|---|
| 2 probes | $\varepsilon_2 = 0.70$ |
| 3 probes | $\varepsilon_3 = 0.70$ |
| 4 probes | $\varepsilon_4 = 0.65$ |
| 5 probes | $\varepsilon_5 = 0.65$ |
| 6 probes | $\varepsilon_6 = 0.65$ |

The above algorithm is based on the following assumptions:

Treatment zone center is at (0,0) or will be translated to (0,0) for calculations.

Treatment zone area may or may not be adequately covered depending on size and number of probes to be deployed.

A fixed angular array of probe placements is used, with the exception of 6 probes in which the last probe is placed in the center of the target tissue at (0,0). (see Table 2.1)

A predetermined firing sequence is used according to the total number of probes. (see Table 2.3 below)

An array of $\varepsilon_j$ for j=2, 3, ... 6 is used to determine the ratio of the probe placement radius from the edges of the target tissue. (see Table 2.2) The numbers are determined empirically for best-fit. Alternatively, these values can be represented as functions rather than fixed numerical values for each number of probes.

A default electric field density between probes is 1500 volts/cm which can be changed by the user. The actual voltage value between probes is adjusted based on the default electric field density. For example, if the default is set at 1500 volts/cm, the actual treatment voltage for a pair of probes that are 1.5 cm apart is 2250V.

TABLE 2.3

| Total number of probes in the device | Firing Sequence of Probe Treatment Pairs, identified by polarity and specific probe number |
|---|---|
| 2 probes | (1 treatment pair)<br>(+) 1, (−) 2 |
| 3 probes | (3 treatment pairs)<br>(+) 1, (−) 2<br>(+) 2, (−) 3<br>(+) 3, (−) 1 |
| 4 probes | (5 treatment pairs)<br>(+) 1, (−) 2<br>(+) 2, (−) 3<br>(+) 3, (−) 4<br>(+) 4, (−) 1<br>(+) 2, (−) 4 |
| 5 probes | (8 treatment pairs)<br>(+) 1, (−) 2<br>(+) 2, (−) 3<br>(+) 3, (−) 4<br>(+) 4, (−) 5<br>(+) 5, (−) 1<br>(+) 2, (−) 5<br>(+) 1, (−) 3<br>(+) 4, (−) 1 |
| 6 probes | (10 treatment pairs)<br>(+) 1, (−) 2<br>(+) 2, (−) 3<br>(+) 3, (−) 4<br>(+) 4, (−) 5<br>(+) 5, (−) 1<br>(+) 1, (−) 6<br>(+) 6, (−) 2<br>(+) 3, (−) 6 |

TABLE 2.3-continued

| Total number of probes in the device | Firing Sequence of Probe Treatment Pairs, identified by polarity and specific probe number |
|---|---|
| | (+) 6, (−) 4 |
| | (+) 5, (−) 6 |

Example 3

A device having 3 probes is used to treat a target tissue where:

a=2.0 cm; b=1.0 cm; and $\varphi$=0 degrees
Using Table 2.1, $\theta_1$=90°, $\theta_2$=210°, and $\theta_3$=330°
Using Table 2.2, $\varepsilon_3$=0.70

Therefore, when using the "Autoset Probes" feature, and eqs. (14) and (15) above, the (x,y) locations on the grid for each probe are calculated as follows:

Probe #1

$x_1 = \varepsilon_j * a * \cos(\theta_i + \varphi) = 0.70 * 2.0 \text{ cm} * \cos(90 \text{ degrees}) = 0$ $y_1 = \varepsilon_j * b * \sin(\theta_i + \varphi) = 0.70 * 1.0 \text{ cm} * \sin(90 \text{ degrees}) = 0.70 \text{ cm}$ Probe #2

$x_2 = \varepsilon_j * a * \cos(\theta_i + \varphi) = 0.70 * 2.0 \text{ cm} * \cos(210 \text{ degrees}) = -1.21 \text{ cm}$ $y_2 = \varepsilon_j * b * \sin(\theta_i + \varphi) = 0.70 * 1.0 \text{ cm} * \sin(210 \text{ degrees}) = -0.35 \text{ cm}$ Probe #3

$x_3 = \varepsilon_j * a * \cos(\theta_i + \varphi) = 0.70 * 2.0 \text{ cm} * \cos(330 \text{ degrees}) = 1.21 \text{ cm}$ $y_3 = \varepsilon_j * b * \sin(\theta_i + \varphi) = 0.70 * 1.0 \text{ cm} * \sin(330 \text{ degrees}) = -0.35 \text{ cm}$ Using Table 2.3, the firing sequence and respective polarity of the three probes will proceed as follows:
(3 treatment pairs)
(+) Probe #1, (−) Probe #2
(+) Probe #2, (−) Probe #3
(+) Probe #3, (−) Probe #1

In another embodiment, the automatic probe placement feature can be executed by the treatment control module 54 to reposition the probes on the grid 200 according to distance measurements which are taken from the actual position of the probes after they have been inserted into the patient.

The user is allowed to enter any or all specific distance measurements taken between any pairs of treatment probes, and may also specify which probes may be repositioned on the grid 200 by the treatment control module 54 and which may not. The treatment control module 54 then finds the minimal error in the positions of the probes that best match the positions seen on the imaging software by the user.

It is very difficult with several probes to place them exactly on the treatment grid 200 at the proper distances that are measured on a CT or similar scan. Often times, two, three, or four probes should be moved or rotated as a group to maintain proper distances between the other probes on the treatment grid 200. This can be a frustrating, time-consuming, and error-prone method of ensuring that the probe locations on the treatment grid 200 mirror the actual probe locations in the patient's body. The positions and distances of the probes are critical in treatment planning and delivery. Furthermore, in one embodiment, the probes may only be placed at exact 1 mm locations on the treatment grid 200 so that they can easily be moved to "snap" to the grid 200, which makes the optimal placements of the individual probes even more difficult.

The main code of the software for this feature involves a "solver" algorithm which performs an iterative search based on the starting positions of the probes and the distances desired as input by the user. Some probes may be specified as "Locked" meaning that their positions are fixed relative to the grid 200. The solver moves all probes in a 1 mm×1 mm array in all possible positions and calculates the root mean square (RMS) error of the distances between the new probe locations and the desired probe locations on the grid 200. The probe positions within each probes' bounding 1 mm box that offer the minimum RMS error to the total solution are taken as the "next" iteration of the algorithm. The solver then takes this new location and re-iterates to find a new, better set of positions on the grid 200. The iterations continue until no improvement in the RMS error of the solution is found, at which point the solver quits and returns the optimal new positions that were found.

This distance placement feature will be used by the user to directly input the probe distances and cause the optimal positions of the probes based on these distances to be displayed on the treatment grid 200 with a minimum of effort and error. This will allow better treatment planning and better treatments. The distance placement feature works best when the user places the probes in "approximately" the correct starting positions on the grid 200 before running the solver algorithm.

Figure 19:
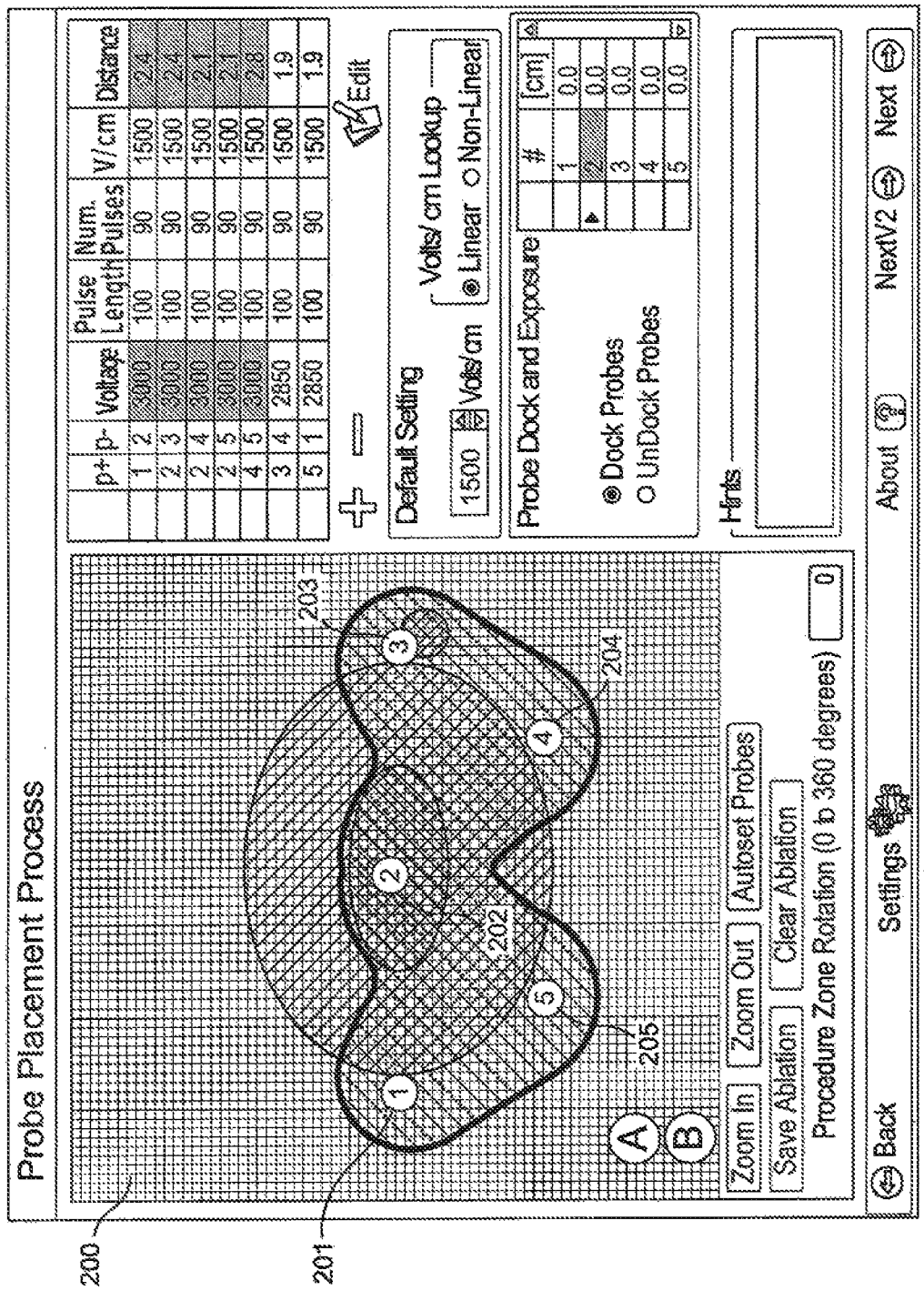
FIGS. 19-22 are screen shots of the treatment control module illustrating an alternative embodiment of an automatic probe placement feature of the treatment control module.
Figures 20, 21:
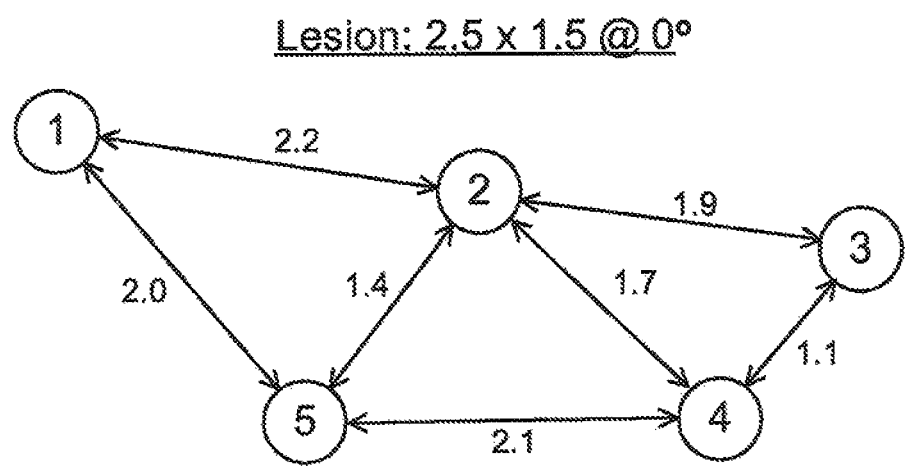

This distance placement feature is illustrated by way of an example which is shown in FIGS. 19-22. FIG. 19 illustrates five probes 201, 202, 203, 204, 205 which form a five probe array to treat a target tissue. The five probes have been placed on the grid 200 by a user to plan the treatment of the target tissue on the "Probe Placement Process" screen. Next, the user actually inserts the five probes into the patient according to the planned locations. However, it is very difficult to actually physically place the probes at the exact same respective locations shown on the grid 200. For example, certain anatomical structures of the patient may prevent the optimal placement of the probes, e.g., the location of the target tissue with respect to the location of the patient's ribs, etc. After the user has placed the five probes in the patient, distance measurements are taken as shown in FIG. 20. These measurements represent the actual position of the five probes in the patient. One way to measure the distances between probes is to use the imaging device 30 such as a ultrasonic imaging device which allows the user to select any two point on the display device 31 to automatically measure the distance as is well-known in the art.

Next, the user clicks on a "Probe Distance Adjuster" button or the like on the screen. FIG. 21 illustrates an example of a pop-up window 333 that appears which includes input boxes for entering the measurement distances taken by the user. As discussed above, the user can select which probes to "lock" on the grid 200, which will fix the location of those probes relative to the grid 200. In the present example, the user has "Locked" the position of the second probe (labelled #2) 202. After the measurement distances have been inputted into the pop-up window 333, the user clicks on the "OK" button to execute this automatic probe placement feature.

Figure 22:
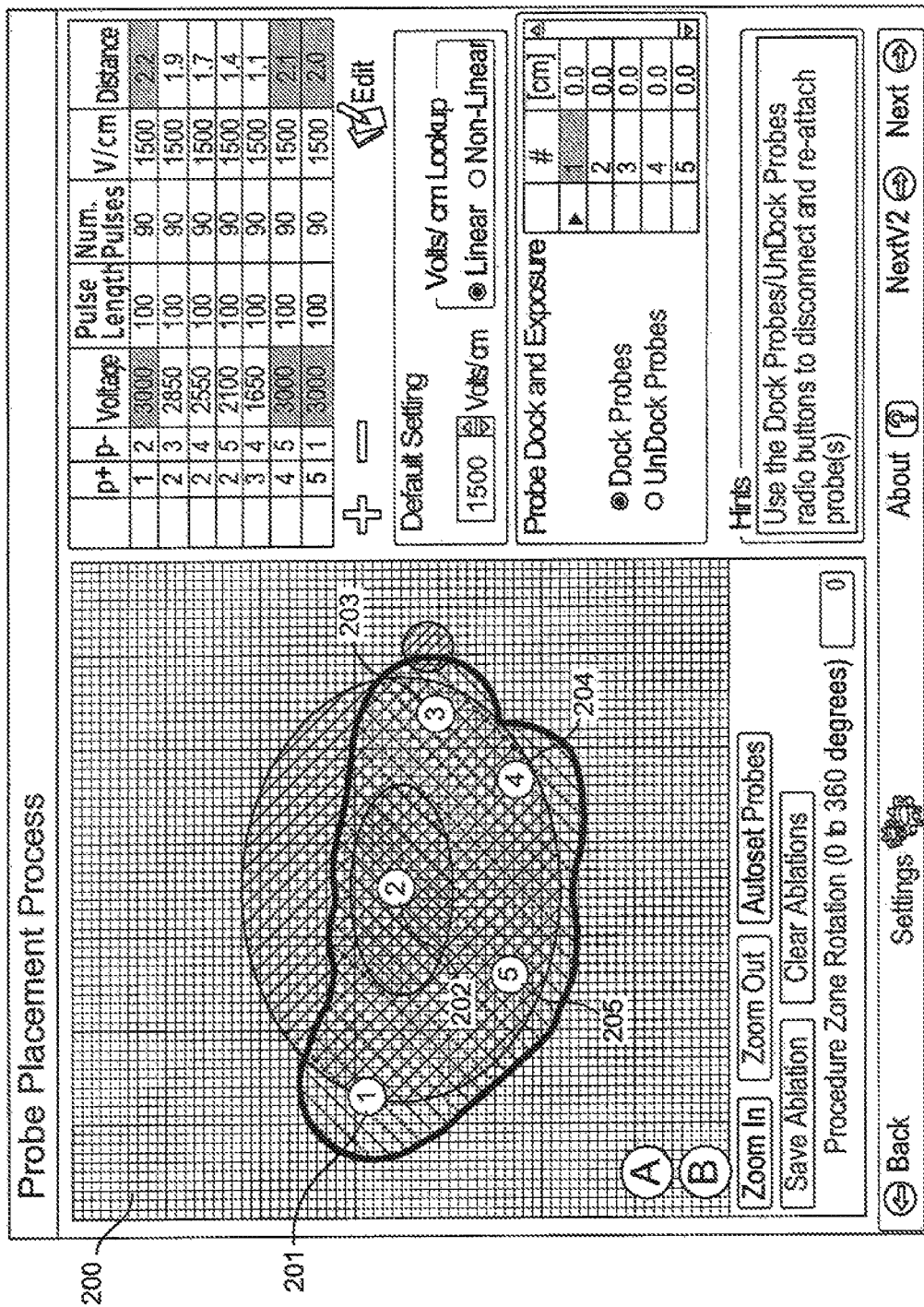

The treatment control module 54 then automatically adjusts the placement of the probes on the grid 200 which have not been "Locked" to best match the distance measurements taken. FIG. 22 shows the placement of the five probes 201, 202, 203, 204, 205 on the grid 200 after the program has been executed.

Referring back to the example shown in FIG. 18, the combined treatment region 315 does not fully cover the safety margin 301 by using a four probe device in the example. FIG. 18 illustrates the four probe device after the "Autoset Probes" button has been depressed. It should be noted that at any time, the user may move any of the probes in the grid 200. When a probe is moved on the grid 200, the treatment control module 54 automatically updates the voltage (treatment energy level) calculation in column 222 based on the distance between the probes and continuously displays the distance between the probe being moved and the other probes (see FIG. 12). The treatment control module 54 also automatically recalculates the size and boundary line 320 of the treatment zones in real time when a probe is moved on the grid 200. Also, when the maximum voltage is achieved (e.g. 3000 Volts), that number as well as its corresponding distance value are highlighted (in different color, for example, relative to the other voltage values and distance values) in column 222 to alert the user.

Figure 26:
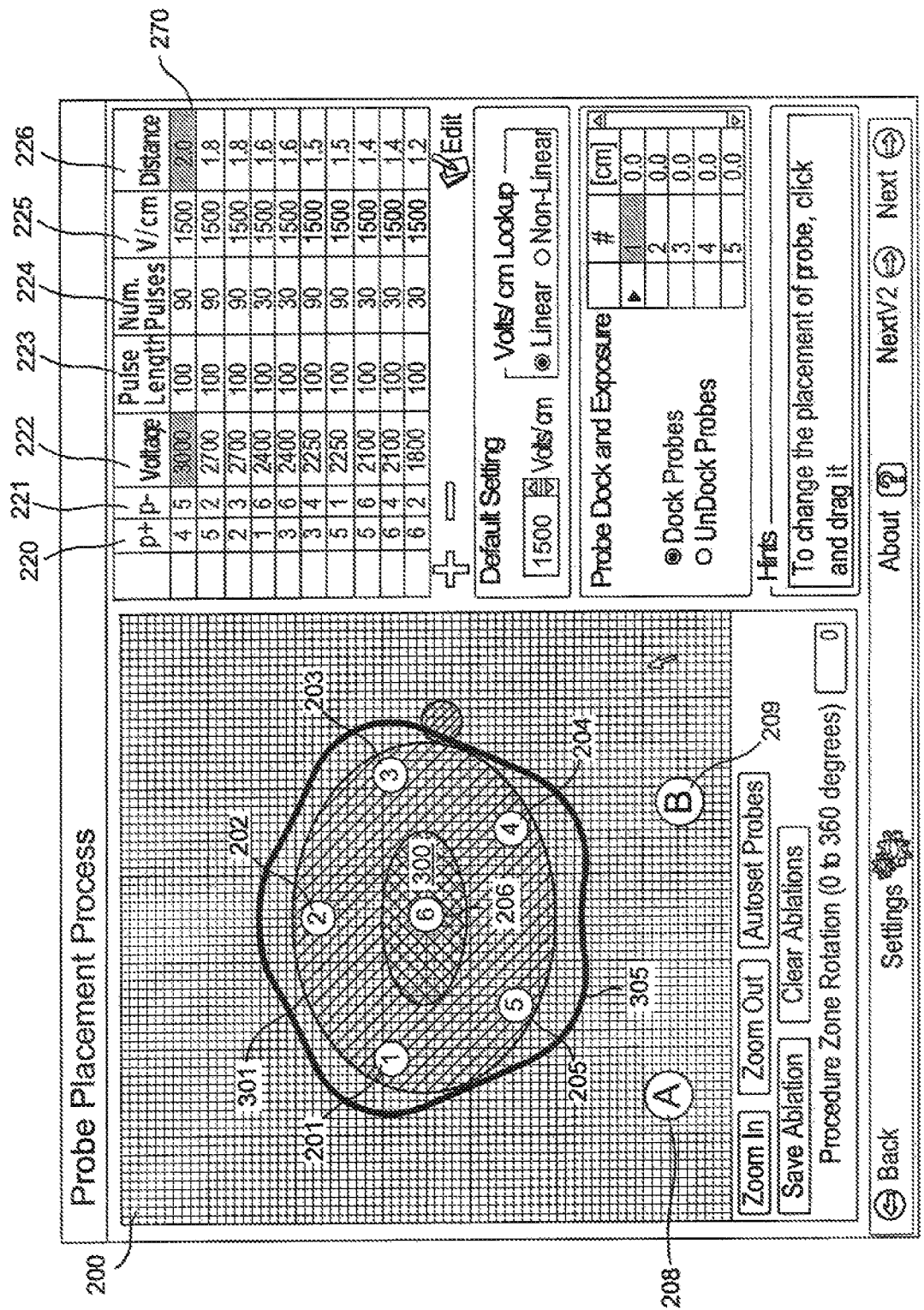
FIG. 26 is a screen shot of a "Probe Placement Process" screen of the treatment control module showing an example of a treatment zone that is created by a six probe array after the "Autoset Probes" button has been depressed by a user.

FIG. 26 illustrates the same target tissue 300 being treated by a six probe device after the "Autoset Probes" button has been depressed. The six probe device does a better job at covering the entire safety margin 305 surrounding the target tissue 300. With the six probe device, more rows of data appear in window 270 than compared with the four probe device discussed above because additional treatment pairs are executed. Because of the additional probes, the distance is smaller between respective probes to cover a similar ablation area. This is reflected in column 226 of window 270. This is also reflected in column 222 of window 270 which displays the voltage generated during each step of treatment. As discussed earlier, the example assumes that the maximum capability of the generator 10 is 3000 Volts. It is preferred to stay below the maximum capability of the generator if possible. Column 222 shows that with the six probe device the power delivered during each step is below 3000 Volts.

Adjusting Treatment Parameters

Figure 23:
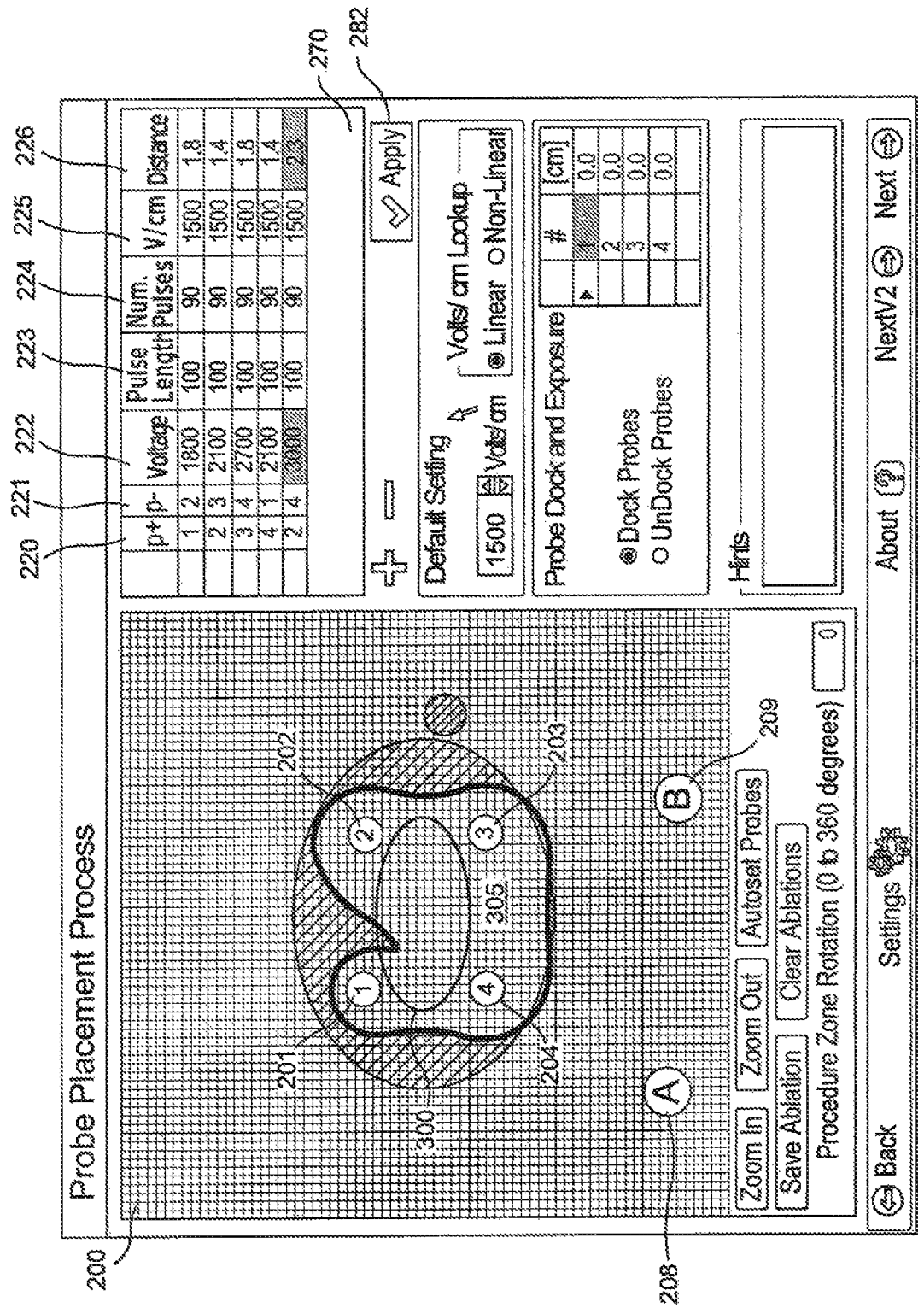
FIGS. 23-25 are screen shots of a "Probe Placement Process" screen of the treatment control module showing several examples of how a user can edit and modify the treatment parameters.

The treatment control module 54 allows a user to manually edit some of the numbers in window 270 in order to tailor the treatment. To edit the numbers in window 270, the user first clicks on the "Edit" icon 281 with the pointing device 14, as shown in FIG. 18. After clicking on the "Edit" icon 281, in one embodiment the treatment control module 54 can change the colors of the particular boxes in window 270 which are able to be edited. For example, as shown in FIG. 23, the treatment control module 54 can display the boxes which are able to be edited (columns 220, 221, 223, 224, 225) in a white color and can display the boxes which cannot be edited (columns 222, 226) in a grey color. Once the user has determined which box(es) to edit, the data in an individual box can be edited by clicking on that particular box with the pointing device 14. After the box has been clicked with the pointing device 14, the value can be edited by either manually deleting and typing in new data with the keyboard 12, or by adjusting the number up or down by clicking on the up arrow or down arrow that appears in the box with the pointing device 14.

In the example shown in FIG. 23, the Volts/cm between probes "1" and "2" has been adjusted down from 1500 Volts/cm to 1000 Volts/cm. If a change is made to the data in window 270 which would affect the shape of the combined treatment zones 305, then the treatment control module 54 automatically adjusts the depiction of the treatment zones 305 shown in grid 200 to reflect this. In the example shown in FIG. 23, the area of the projected combined treatment region 305 has been diminished between probes "1" and "2" as shown. The ability to edit the treatment parameters as described can be particularly useful to a user in certain situations. For example, a user can edit the treatment parameters in order to avoid areas that should be preserved, such as a location of a nerve or the like. Once the user has completed making any edits of the boxes in window 270, if any, the edits are saved to the treatment control module 54 by clicking on the "Apply" icon 282 with the pointing device 14.

Figure 24:
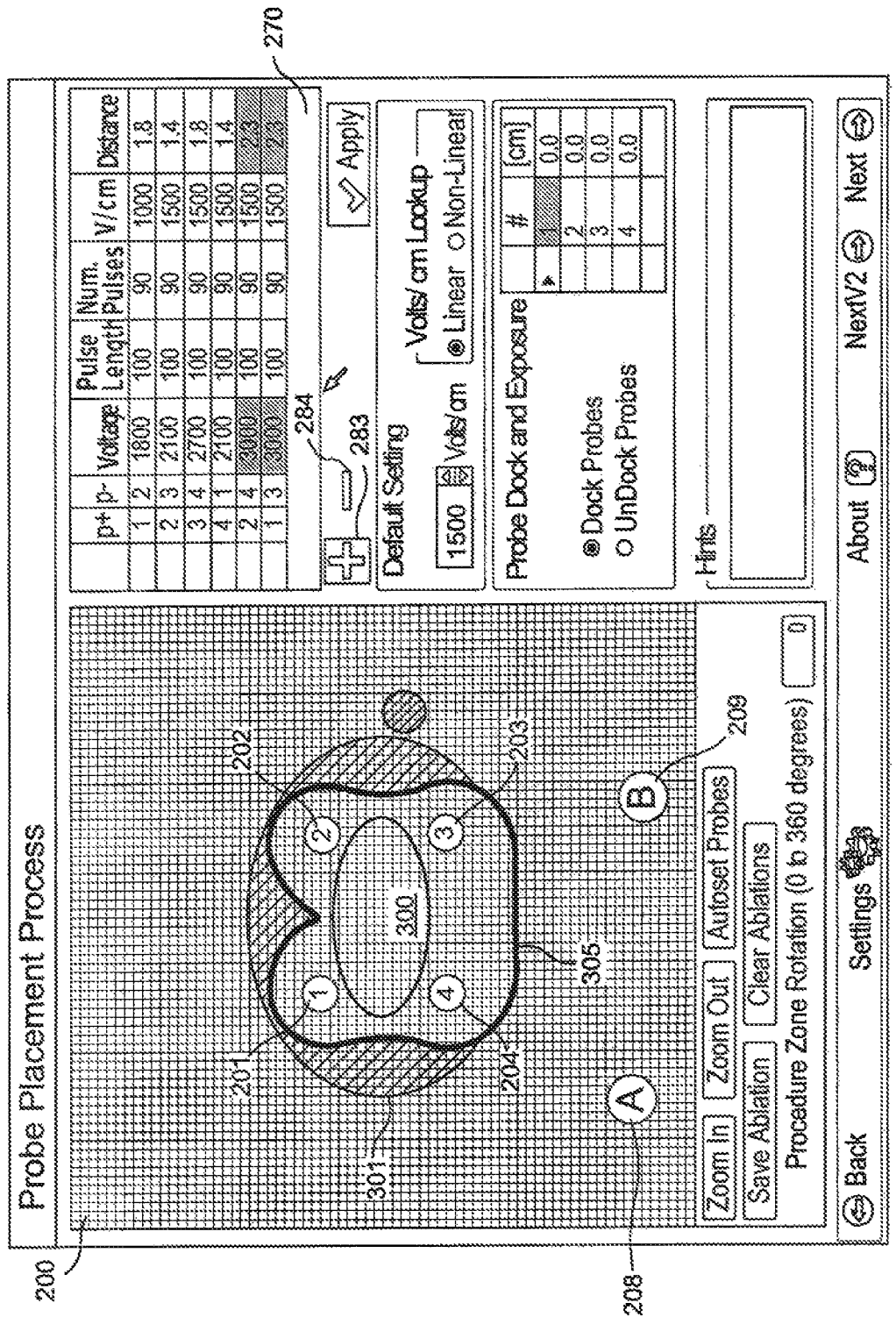

The treatment control module 54 allows a user to manually add additional rows or delete rows from the window 270 in order to tailor the treatment. To add rows in window 270, the user first clicks on the "+" icon 283 with the pointing device 14, as shown in FIG. 24. After clicking on the "+" icon 283, an additional row will appear at the bottom of the list in window 270, which will indicate an additional pair of probes in which treatment will occur. In the example shown in FIG. 24, an additional row has been added which indicates that treatment will occur between probe "1" and probe "3". Referring to the grid 200, this additional treatment pair indicates the diagonal treatment across the target tissue. It should be noted that a diagonal treatment was already present between probe "2" and probe "4" as indicated in window 270. However, by adding an additional diagonal treatment, overlapping with the other treatment zones, in combination with other edits to the boxes in window 270, as described above, the user can tailor the shape of the combined treatment region 305. Whenever a row is added or deleted, the treatment control module 54 automatically updates the anticipated combined treatment zone displayed in grid 200. By comparing the grid 200 in FIG. 23 to the grid 200 in FIG. 24, the effect of adding the additional treatment row between probe "1" and probe "4" can be visually understood and appreciated. To delete rows in window 270, the user first selects which row is to be deleted by clicking to the left of the selected row with the pointing device 14. Next, the user clicks on the "-" icon 284 with the pointing device 14, as shown in FIG. 24, thereby deleting the selected row from window 270.

Figure 25:
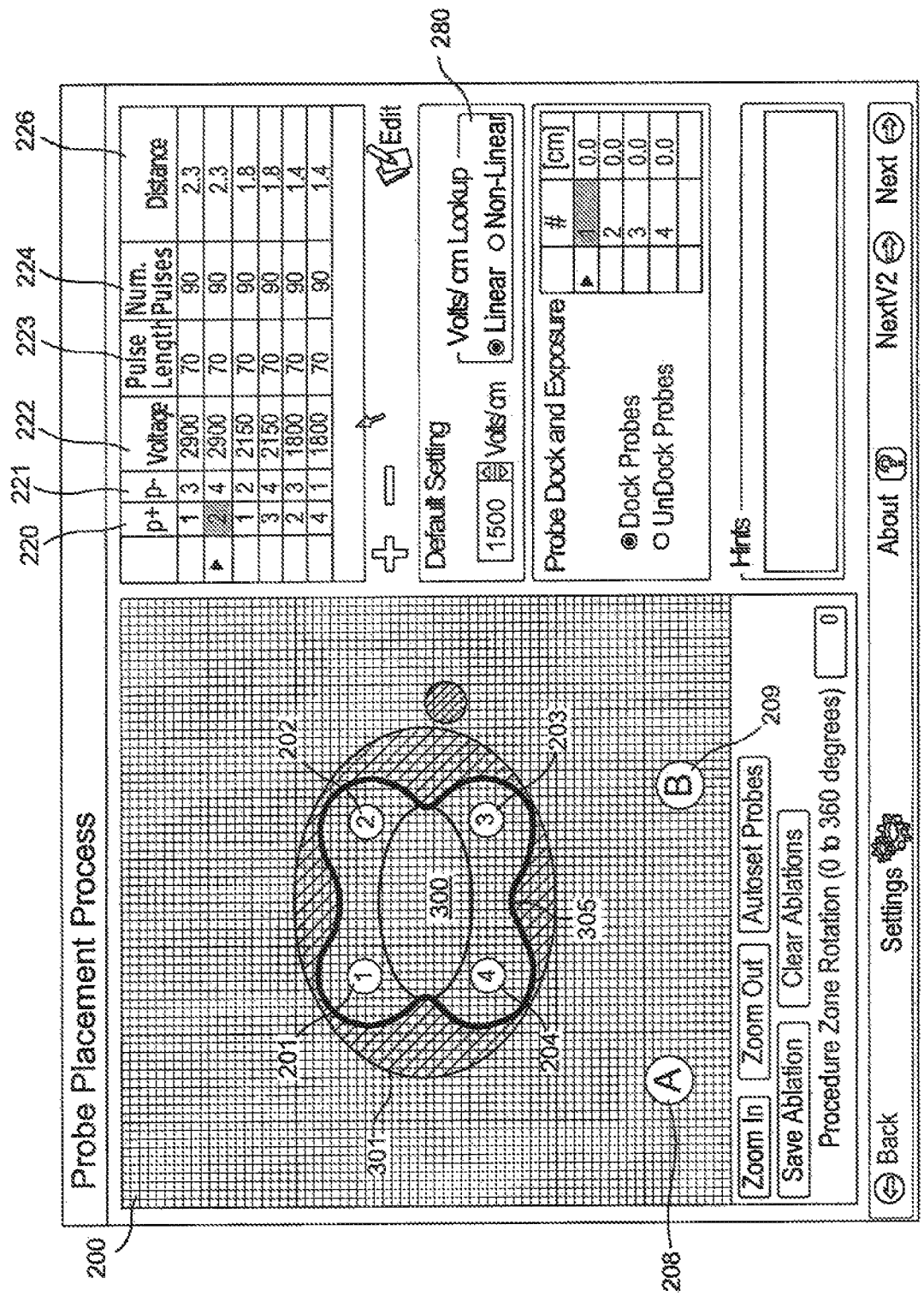

As discussed earlier, the user can select between a "Linear" or "Non-linear Lookup" for determining how the treatment control module 54 will calculate the actual voltage (column 222) that will be applied between each pair of probes. FIG. 25 illustrates the result when the "Non-linear Lookup" circle is selected in box 280, when compared to FIG. 18 which illustrates the same number of probes, the same probe placement, and the same Default Setting (1500 V/cm), but instead when the "Linear" circle is selected in box 280.

After the user is satisfied with the positioning of the probes of the device and the other settings according to the features discussed above, the user clicks on the "Next" button with a pointing device 14 to proceed to the "Pulse Generation" screen described below.

Figure 27:
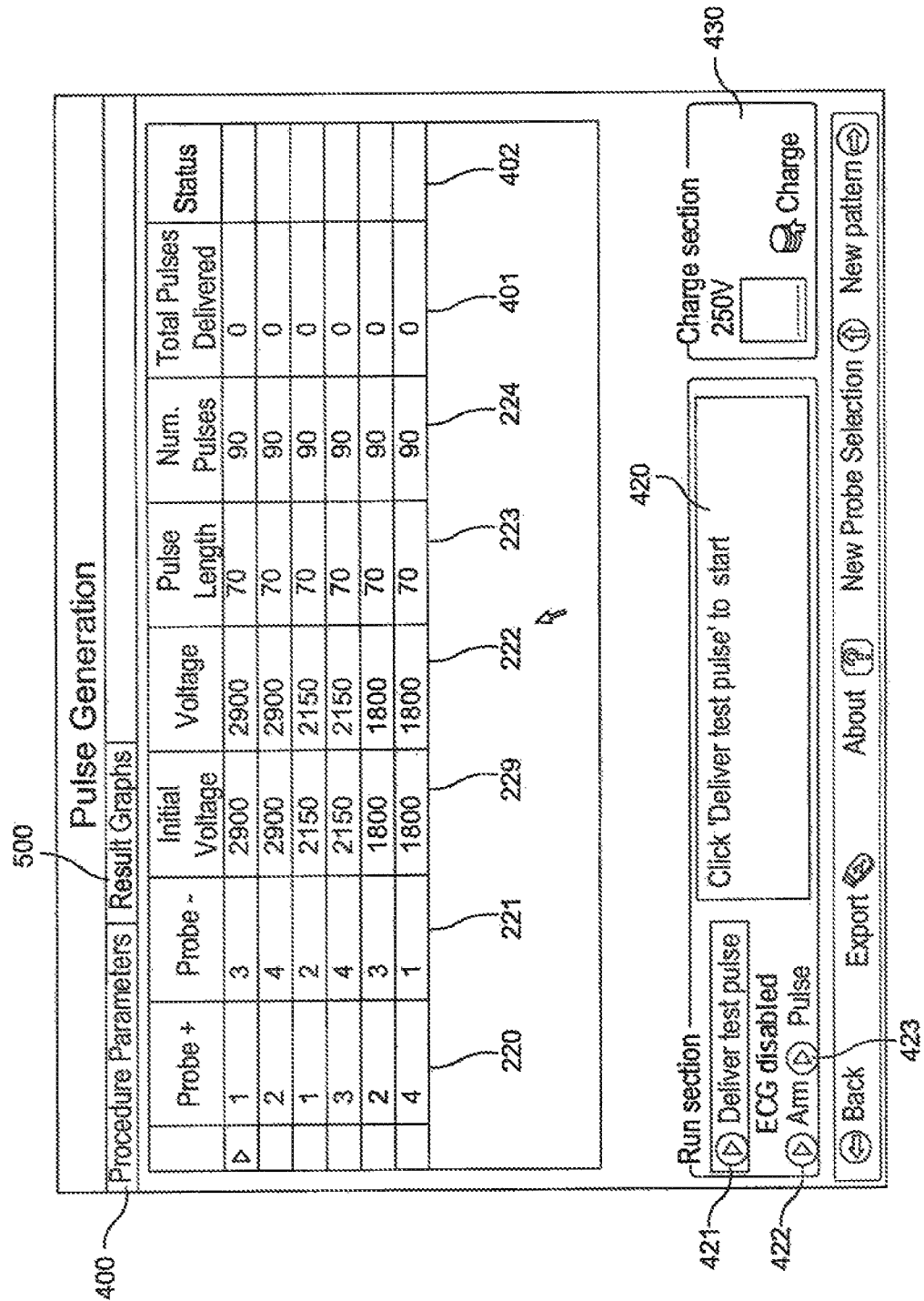
FIG. 27 is a screen shot of a "Pulse Generation" screen of the treatment control module showing the status of the treatment parameters before the treatment procedure has been initiated by a user.

FIG. 27 illustrates the status of the treatment before the treatment has been initiated. The following steps describe how the treatment is administered once the user has reached the "Pulse Generation" screen illustrated by FIG. 27.

In FIG. 27, the treatment control module 54 asks the user to "Click 'Deliver test pulse' to start" in window 420 in order to start the test signal (pulse) sequence. After the user presses the "Deliver test pulse" button 421 with the pointing device 14, the control module 54 charges the pulse generator 10 to the test pulse voltage. When the generator 10 is charged, the control module 54 applies a test pulse for each probe pair through the generator 10. For a 4 probe treatment, for example, a test pulse is applied through pairs 1-2, 1-3, 2-3, 2-4, 3-4 and 4-1 as shown in FIG. 11.

In one embodiment, this test pulse voltage is approximately $\frac{1}{10}$ to $\frac{1}{5}$ the maximum treatment voltage but no lower than 200 volts and no higher than 500 volts. (It should be noted that in a preferred embodiment, valid treatment voltages are between 500 to 3000 volts.) In the embodiment shown, a test pulse of 400 volts is used for each pair of electrodes. From the test pulse, the treatment control module 54 then checks the current through a sensor 73 (see FIG. 29) for each probe pair to determine whether a treatment current will be too low (e.g., below approximately 300 milliamps) or too high (e.g., approximately 45 amps or more). Based on the current, the resistance R or conductance (1/R) of the tissue is calculated by the module 54. Then, the voltage to be used to actually treat the tissue (see column 222 in FIG. 23, for example) is divided by the resistance to obtain the treatment current draw to be used in the treatment.

If the treatment current draw is determined to be too low (e.g., below 300 milliamps), the system will give the user the option to "Proceed to Treatment" for each pair that was too low in current. If the current is determined to be too high (e.g., 45 amps or more of threshold maximum current draw), the control module 54 will indicate an error in the display device 11 and the user should change the treatment voltage and/or re-position the mis-aligned probes to reduce the current.

The treatment control module 54 generally applies one test pulse for every pair listed in the treatment spreadsheet although more than one pulse can be applied to each pair. For example, if the user sets up treatment between pairs (1 to 2), (1 to 3) and (2 to 3) there will be three test pulses, one for each pair. There is no therapeutic value in the test pulse. The test pulse only checks the setup before full therapeutic treatment is applied. Each test pulse is intended to ensure that two conditions are met with each test pulse: first, that there is a valid connection between the selected treatment pairs, and second, that the current will not exceed the maximum output capability of the generator 10 (see FIG. 1).

Another reason for the administration of a "test pulse" is to ensure that the patient is properly anesthetized. Prior to treatment, the patient is administered general anesthesia in combination with a paralytic agent. If the patient is not paralyzed with anesthesia, then a noticeable muscle contraction will occur during administration of the "test pulse". Since the test pulse is at approximately 10% to 20% of the therapeutic level, any muscle contraction displayed by the patient is not as much as it would be if full energy was applied. The user should be trained to watch for muscle movement during the test pulse. In one embodiment, the treatment control module 54 can display a window which asks the user to confirm that there is no muscle movement being displayed by the patient by selecting an answer with the pointing device 14. In this embodiment, the treatment control module 54 will not continue to the next step unless the user presses a button with the pointing device to indicate that the patient did not display any muscle contraction during the test pulse. Irreversible electroporation (IRE) requires that a paralytic agent is given as well as the normal anesthesia. These agents tend to have a short half-life and it is easy for the patient to be under medicated at the time of treatment. If the patient is under-medicated, it is possible that the patient could be injured from the severe muscle contraction that would occur from a full power treatment without a muscle blockade. The energies delivered by IRE are similar to a defibrillation pulse and the muscle contraction would also be similar.

After these steps are completed, the system charges to the full therapeutic treatment voltage (as shown in window 430) and waits for instructions from the user to begin treatment. In a preferred embodiment, a user is required to press both foot pedals of a double foot pedal device (not shown) in order to activate treatment (the first pedal is used to arm the generator 10, the second pedal is used to fire or start the treatment). This provides a type of safety check and prevents accidental activation of the treatment. For illustration purposes, the screen shown in FIG. 27 uses two buttons 422, 423 instead of a double foot pedal device. Accordingly, the user will click on the "Arm" button 422 with the pointing device 14 to arm the probes. Then, the user will click on the "Pulse" button 423 with the pointing device 14 to initiate the treatment.

Figure 28:
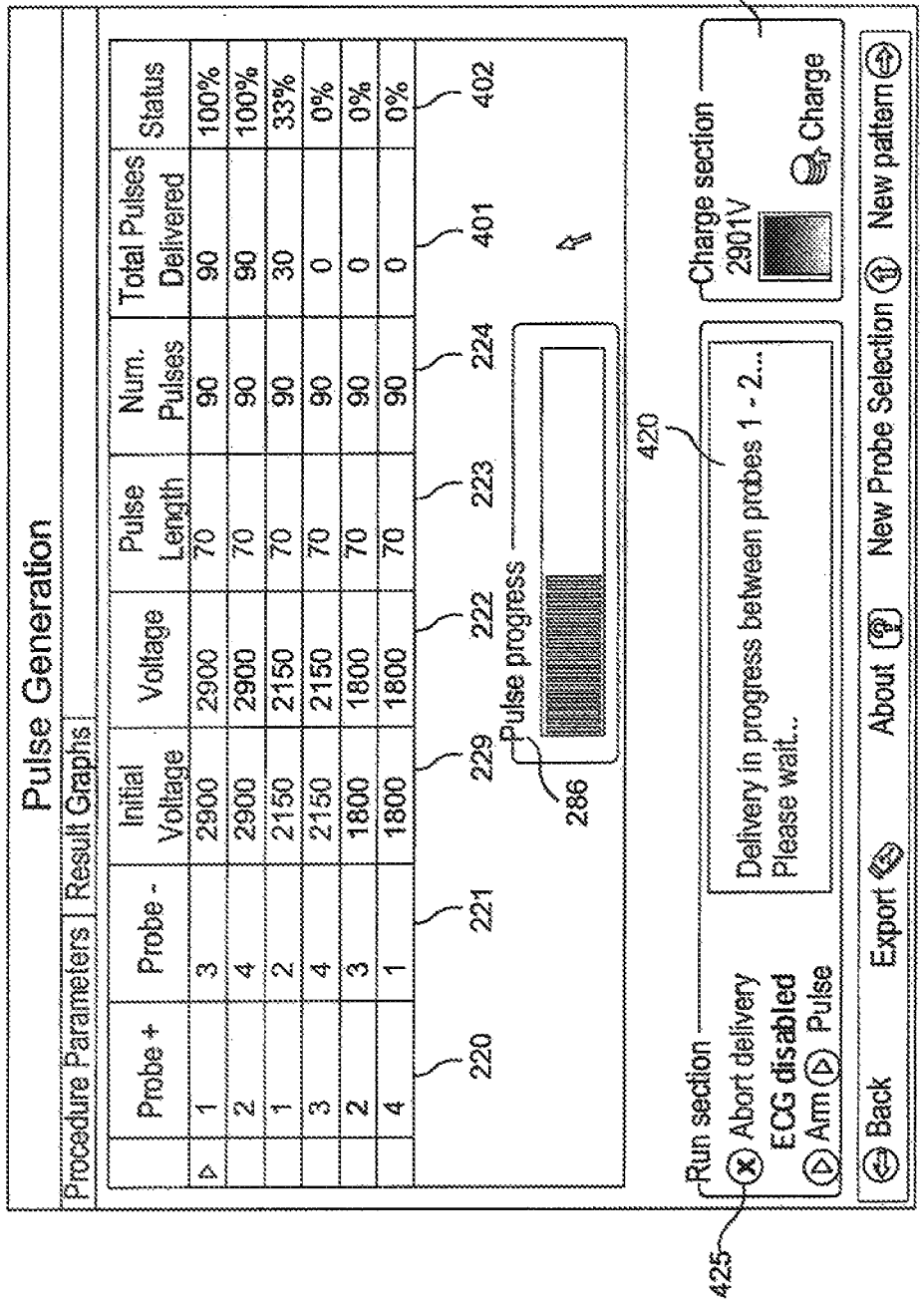
FIG. 28 is a screen shot of a "Pulse Generation" screen of the treatment control module showing the status of the treatment parameters during the treatment procedure.

As shown in FIG. 28, after the treatment has been initiated, the treatment control module 54 controls the generator 10 and administers a series of pulses according to the predetermined instructions illustrated in columns 220, 221, 222, 223, 224. During each step of the treatment, column 401 illustrates the number of pulses that have been delivered in real time until the total number of predetermined pulses has been delivered. Column 402 displays the status percentage of the treatment for each pair of electrodes. The treatment process runs until each step of the probe firing sequence has been accomplished. Audible beeps are generated during the treatment to track the operation of the generator 10. Window 430 displays the status of the charge of the generator 10 during operation. Window 286 displays the total "Pulse progress" of the treatment. Window 420 displays further details of the treatment progress.

The treatment control module 54 can include a feature that prevents the generator from exceeding its maximum current limit by reading the current every ten pulses and reducing the voltage by a predetermined percentage (e.g., 5% or 10%) if it approaches the maximum limit of the generator.

FIG. 29 illustrates one embodiment of a circuitry to detect an abnormality in the applied pulses such as a high current, low current, high voltage or low voltage condition. This circuitry is located within the generator 10 (see FIG. 1). A USB connection 52 carries instructions from the user computer 40 to a controller 71. The controller can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. For clarity, only one pair of probes/electrodes are shown. However, the generator 10 can accommodate any number of probes/electrodes (e.g., 6 probes as shown in FIG. 4). In the embodiment shown, the pulses are applied one pair of electrodes at a time, and then switched to another pair. The pulse generation circuit 72 includes a switch, preferably an electronic switch, which switches the probe pairs based on the instructions received from the computer 40. A sensor 73 such as a sensor can sense the current or voltage between each pair of the probes in real time and communicate such information to the controller 71, which in turn, communicates the information to the computer 40. If the sensor 73 detects an abnormal condition during treatment such as a high current or low current condition, then it will communicate with the controller 71 and the computer 40 which may cause the controller to send a signal to the pulse generation circuit 72 to discontinue the pulses for that particular pair of probes.

The treatment control module 54 can further include a feature that tracks the treatment progress and provides the user with an option to automatically retreat for low or missing pulses, or over-current pulses (see discussion below). Also, if the generator stops prematurely for any reason, the treatment control module 54 can restart at the same point where it terminated, and administer the missing treatment pulses as part of the same treatment.

In other embodiments, the treatment control module 54 is able to detect certain errors during treatment, which include, but are not limited to, "charge failure", "hardware failure", "high current failure", and "low current failure".

The following discussion relates to an example of a "high current failure". Referring to FIG. 30, a "high current" failure occurred during treatment between probe "1" and probe "2". As can be seen in column 401, the total number of pulses that were delivered between probe "1" and probe "2" was 20 instead of 90. This is because a "high current" condition occurred sometime after the 20th pulse was delivered. The treatment control module 54 was able to react to this error by discontinuing the remainder of the pulses between probe "1" and probe "2".

During treatment energy stored on capacitors acts like a constant voltage source. It is not an ideal source and there is some drift of the applied voltage but it is close. What tends to occur during IRE treatment is as the cells porate, the intracellular fluid moves to the extracellular space. Since the intra cellular fluid is more conductive than the bulk tissue the overall resistance of the system decreases. Given the approximately constant voltage source when resistance goes down current goes up (V=IR). During treatment the system constantly monitors the energy being delivered. If the voltage is too high or too low the therapy is aborted because the primary variable controlling poration is the voltage applied and the geometry the voltage is applied to. The system also monitors the current delivered and ensures that for patient safety reasons and for hardware reliability the maximum current capabilities of the system are not exceeded. Low currents are also detected as a sign of poor connection to the patient.

Any time current flows the tissue will heat up. For IRE the system is trying to deliver as much energy as it can without significant thermal effects. If the current was allowed to run uncontrolled, then thermal damage could occur. Also the components in the system would fail at some point if the system allowed unlimited amounts of current to flow.

After the treatment control module 54 has completed treatment for all probe pairs, column 402 displays whether the treatment was successful for each step of the treatment process by indicating a checkmark, or other indicia, if the step was successful and a lightning bolt, or other indicia, if the step encountered an error. In the example shown in FIG. 30, the treatment between probe "1" and probe "2" indicates a "High Current" error in column 402 as discussed above. The treatment control module 54 tracks which pairs of probes have failed and automatically asks the user whether to "Continue Procedure" (by pressing button 426) or "Stop Procedure" (by pressing button 427). In this example, then the user chooses one of the following three options. 1) Accept the treatment as is (by pressing button 427). For example, if 89 of 90 pulses were properly delivered that may be acceptable. 2) Use the automated reduce and reapply option in the treatment control module 54 (by pressing button 426). This will lower the voltage and the corresponding current and will provide some level of treatment. 3) Reposition the probes to be further apart. This will increase the resistance of the system.

If the user clicks on the "Continue Procedure" button 426, then as shown in FIG. 31, a dialogue box 428 will automatically pop up, which asks the user whether to "Adjust voltages for high current segments?" The user answers by clicking "Yes", "No", or "Cancel". If the user clicks on the "Yes" button, then the treatment control module 54 will automatically reduce the treatment voltage by a predetermined percentage (e.g. 5% which can be set or changed by the user). If the user clicks on the "No" button, then the treatment control module 54 will keep the treatment voltage the same. Next, the treatment control module 54 will go back to the arm ready state. The user can then activate the treatment to re-treat only the missing pulses. This high-current detection and reapplication feature is particularly advantageous because (1) the software remembers which pairs have failed so that the user does not have to remember and (2) the treatment control module 54 is able to accurately keep track of which pulses were unsuccessful so that only the missing pulses are re-administered.

Figure 32:
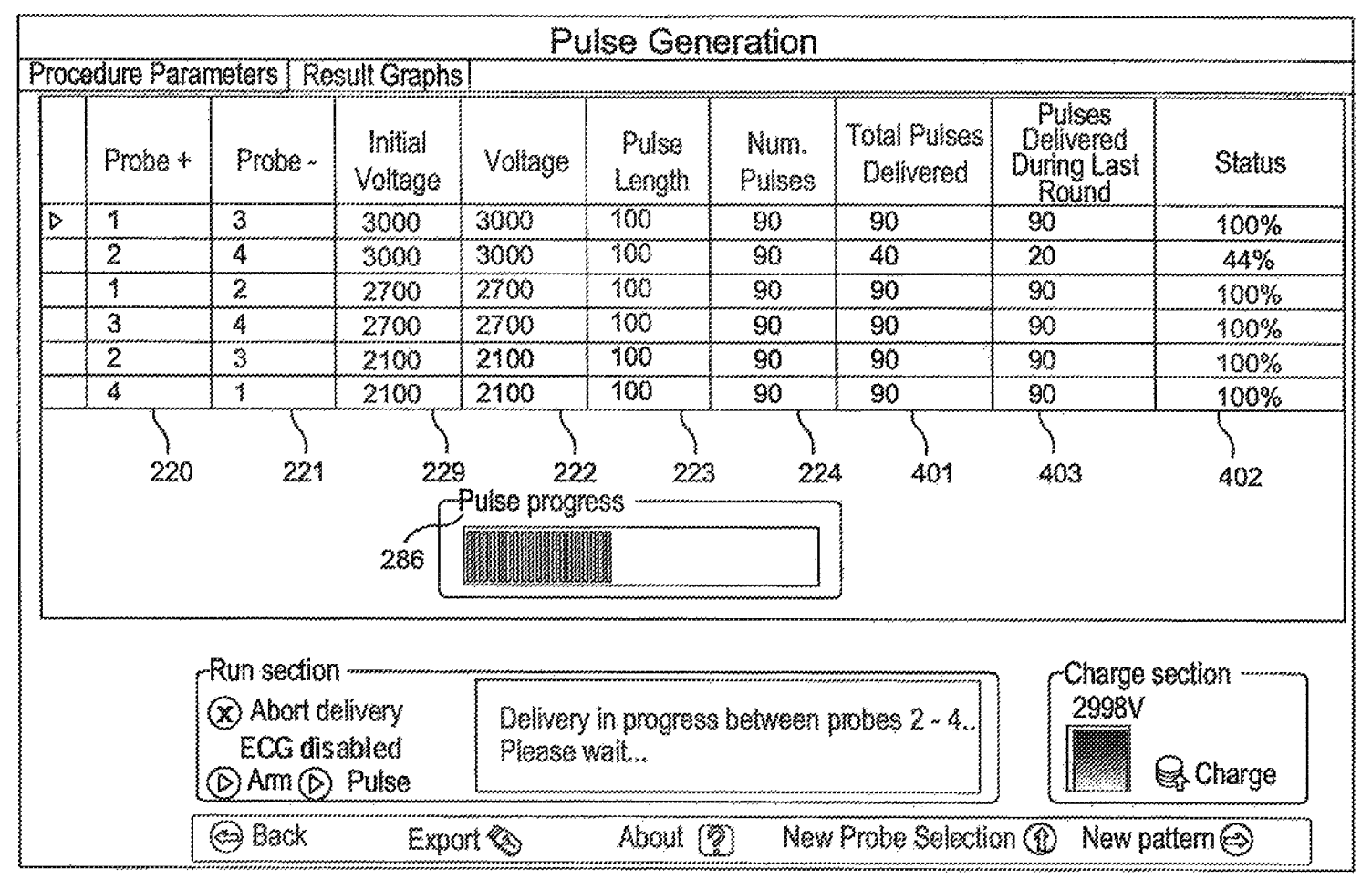

FIG. 32 illustrates the "Pulse Generation" screen during re-treatment for the example. Again the pulse progress bar 286 is displayed and the status column 402 is updated again in real time. After the re-treatment has completed, the user will verify that the status of each probe pair is complete by checking column 402.

Figure 33:
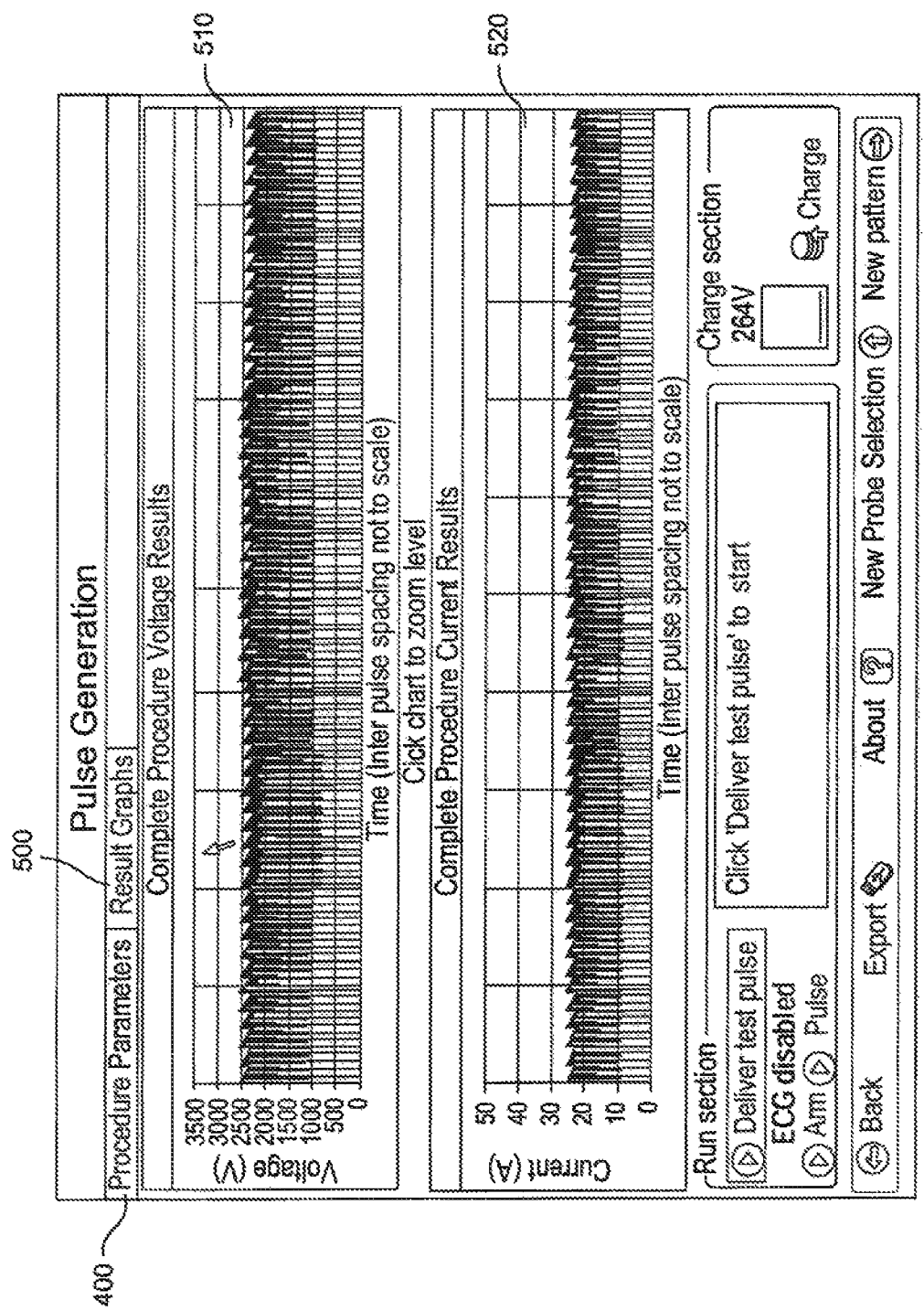
FIGS. 33-34 are screen shots of a "Pulse Generation" screen of the treatment control module showing examples of result graphs.

At any time, the user can click on the "Result Graphs" tab 500 to view the complete voltage (V) results of the treatment vs. time, and the complete current (A) results of the treatment vs. time. FIG. 33 illustrates such result graphs according to the results of the treatment from the example.

In the embodiment shown, a plurality of sets of pulses are applied, and more specifically 9 sets of 10 pulses per set are applied with each pulse having a pulse duration of 100 microseconds.

Figure 34:
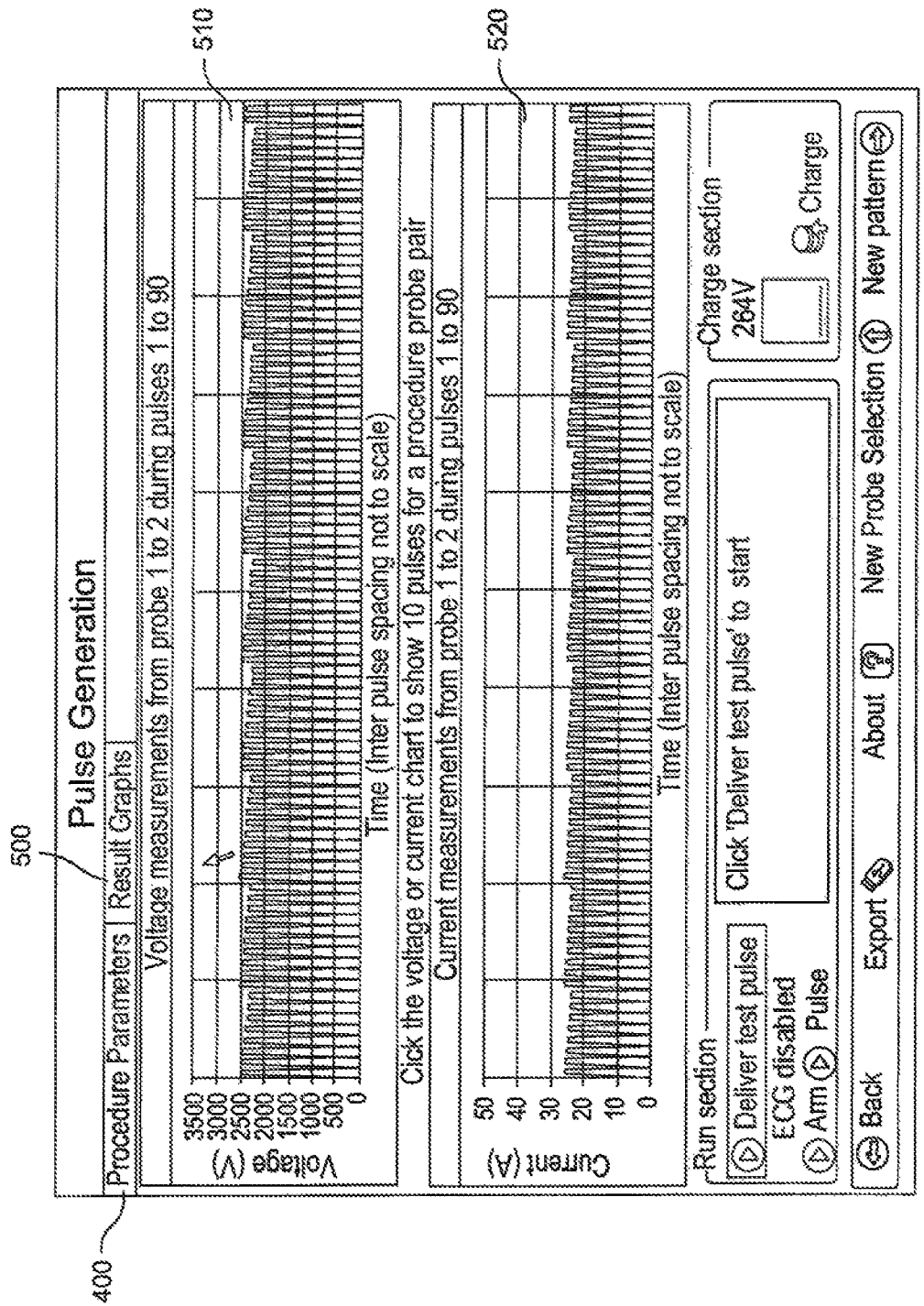

In the illustrations of FIGS. 33-34, the inter pulse spacing is not to scale. The inter pulse spacing is calculated based on the pulses per minute (PPM) which was selected on the "Information" screen (see FIG. 3). The time between sets of pulses is about 3.5 seconds and can be a function of how long the capacitors need to charge. In another embodiment, the time between sets of pulses is less than 3.5 seconds or is completely eliminated.

The user can click the chart to change the zoom level of the result graphs. FIG. 34 illustrates the graph results after the user has clicked the chart to zoom in on the results. The user can further zoom in by clicking the voltage or current chart to show 10 pulses for a treatment probe pair. The graph results shown in FIGS. 33-34 are the results of a demonstration mode of the treatment control module 54. It should be understood that during a real world treatment, the graph results would be less uniform. The shape of the pulses can also be used as an indicator of the degree of poration of the cells.

Figure 35:
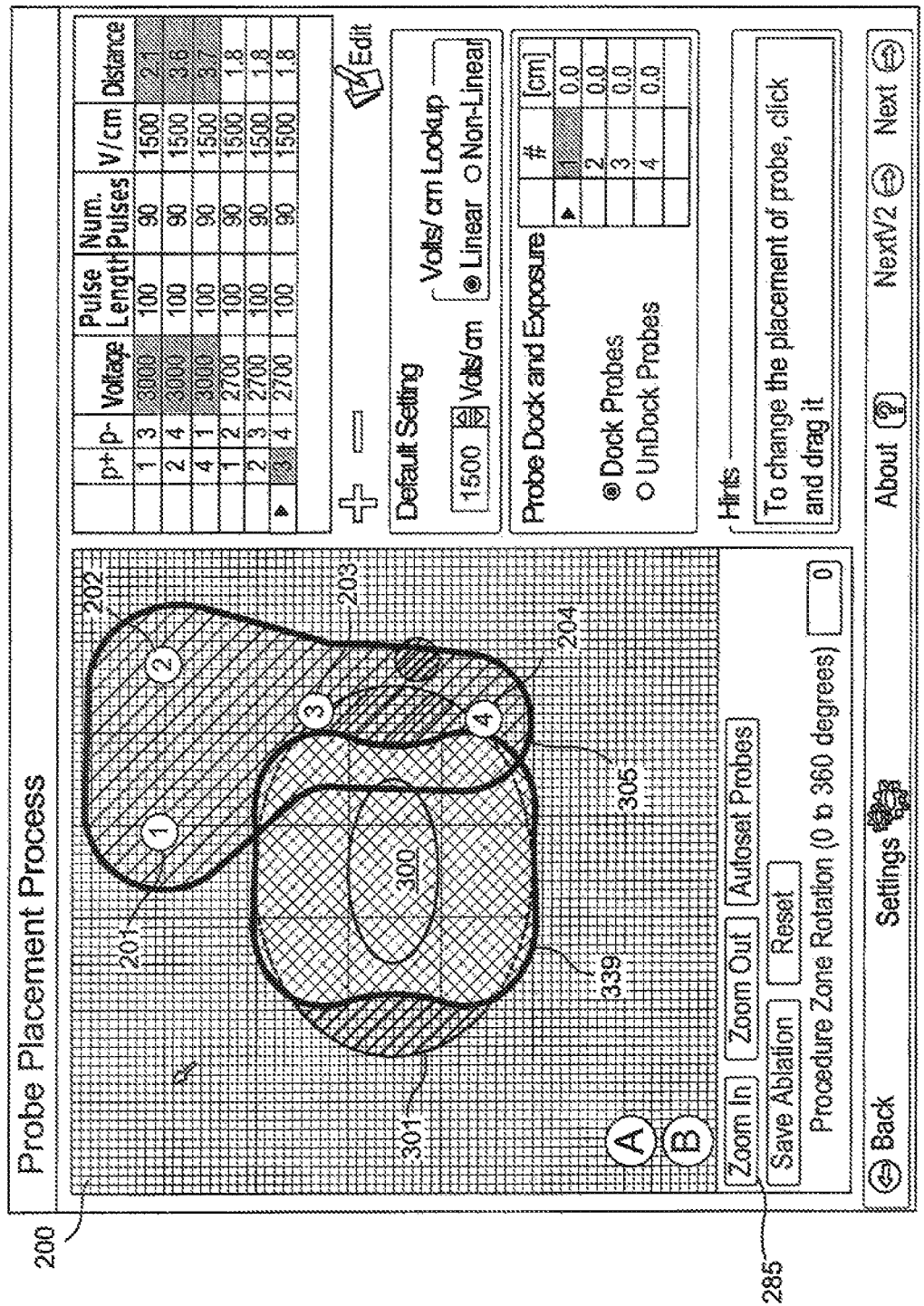
FIG. 35 is a screen shot of a "Probe Placement Process" screen of the treatment control module showing the probe placement grid after treatment has been delivered by the probes.

FIG. 35 is a screen shot of a "Probe Placement Process" screen of the treatment control module showing the probe placement grid 200 after treatment has been delivered by a four probe array. The treated area 339 is saved by the module 54 in the memory 44 and is shown in a highlighted contrasting manner to the displayed target region 301 and the treatment region 305 defined by the probes. In FIG. 35, the treated area 339 is filled in with cross-hatched lines that are marked in any other way for distinguishing this area on the grid 200. In one embodiment, the treated area 339 is displayed in a different color to more easily distinguish it.

This feature allows a user to plan for additional treatment of the target tissue 300 which is surrounded by the safety margin 301. This feature is especially useful when the target tissue (treatment target area) requires more than one round of treatment to effectively cover the entire area.

Although the present treatment method has been discussed in relation to irreversible electroporation (IRE), the principles of this invention can be applied to any other method where therapeutic energy is applied at more than one point. For example, other methods can include reversible electroporation, supraporation, RF ablation, cryo-ablation, microwave ablation, etc. "Supraporation" uses much higher voltages and currents, in comparison to electroporation, but with shorter pulse widths.

In addition to the example parameters described above, specific electro-medical applications of this technology include reversible electroporation as well as irreversible electroporation. This could include reversible or irreversible damage to the external cell membranes or membranes of the organelles, or damage to individual cellular structures such as mitochondrion so as to affect cellular metabolism or homeostasis of voltage or ion levels. Example embodiments for reversible electroporation can involve 1-8 pulses with a field strength of 1-100 V/cm. Other embodiments altering cellular structures adversely involve generators having a voltage range of 100 kV-300 kV operating with nano-second pulses with a maximum field strength of 2,000 V/cm to and in excess of 20,000 V/cm between electrodes. Certain embodiments can involve between 1-15 pulses between 5 microseconds and 62,000 milliseconds, while others can involve pulses of 75 microseconds to 20,000 milliseconds. In certain embodiments the electric field density for the treatment is from 100 Volts per centimeter (V/cm) to 7,000 V/cm, while in other embodiments the density is 200 to 2000 V/cm as well as from 300 V/cm to 1000 V/cm. Yet additional embodiments have a maximum field strength density between electrodes of 250V/cm to 500V/cm. The number of pulses can vary. In certain embodiments the number of pulses is from 1 to 100 pulses. In one embodiment, as described herein, between about 10 pulses and about 100 pulses can be applied at about 2,000 V/cm to about 3,000 V/cm with a pulse width of about 10 μsec to about 50 μsec. After applying these pulses, a predetermined time delay of from about 1 seconds to about 10 minutes can optionally be commenced in order that intra-cellular contents and extra-cellular contents of the target tissue cells can mix. This procedure can be repeated, as necessary, until a conductivity change is measured in the tissue. Following this step, about 1 pulse to about 300 pulses of about 2,000 V/cm to about 3,000 V/cm can be applied with a pulse width of about 70 μsec to about 100 μsec to widely ablate the tissue. This last step can be repeated until a desired number of ablation pulses is delivered to the tissue, for example, in the range of about 10 pulses to about 300 pulses, more particularly, about 100 pulses. In other embodiments, groups of 1 to 100 pulses (here groups of pulses are also called pulse-trains) are applied in succession following a gap of time. In certain embodiments the gap of time between groups of pulses can be from about 0.5 second to about 10 seconds.

Therapeutic energy delivery devices disclosed herein are designed for tissue destruction in general, such as resection, excision, coagulation, disruption, denaturation, and ablation, and are applicable in a variety of surgical procedures, including but not limited to open surgeries, minimally invasive surgeries (e.g., laparoscopic surgeries, endoscopic surgeries, surgeries through natural body orifices), thermal ablation surgeries, non-thermal surgeries, as well as other procedures known to one of ordinary skill in the art. The devices may be designed as disposables or for repeated uses.

In yet another embodiment, the electrodes can be adapted to administer electrical pulses as necessary in order to reversibly or irreversibly electroporate the cell membranes of infectious cells located along the outer surface of an implanted medical device within a treatment zone, thereby treating a patient and sterilizing the medical device. By varying parameters of voltage, the number of electrical pulses, and pulse duration, the electrical field will either produce irreversible or reversible electroporation of the infectious cells that cover the implanted medical device. The pulse generator of the present invention can be designed to deliver a range of different voltages, currents and duration of pulses as well as number of pulses. Typical ranges include but are not limited to a voltage level of between 100-3000 volts, a pulse duration of between 20-200 microseconds (more preferably 50-100 microseconds), and multiple sets of pulses (e.g. 2-5 sets) of about 2-25 pulses per set and between 10-500 total pulses. The pulse generator can administer a current in a range of from about 2,000 V/cm to about 6,000 V/cm. The pulse generator can provide pulses which are at a specific known duration and with a specific amount of current. For example, the pulse generator can be designed upon activation to provide 10 pulses for 100 microseconds each providing a current of 3,800 V/cm+/−50%+/−25%, +/−10%, +/−5%. Plastic and/or other types of metallic devices can be sterilized along the outer surface of the device, as electric field lines from the electrodes can travel along the outer surface of devices. The electroporation treatment zone is defined by mapping the electrical field that is created by the electrical pulses between two electrodes.

Figure 36A:
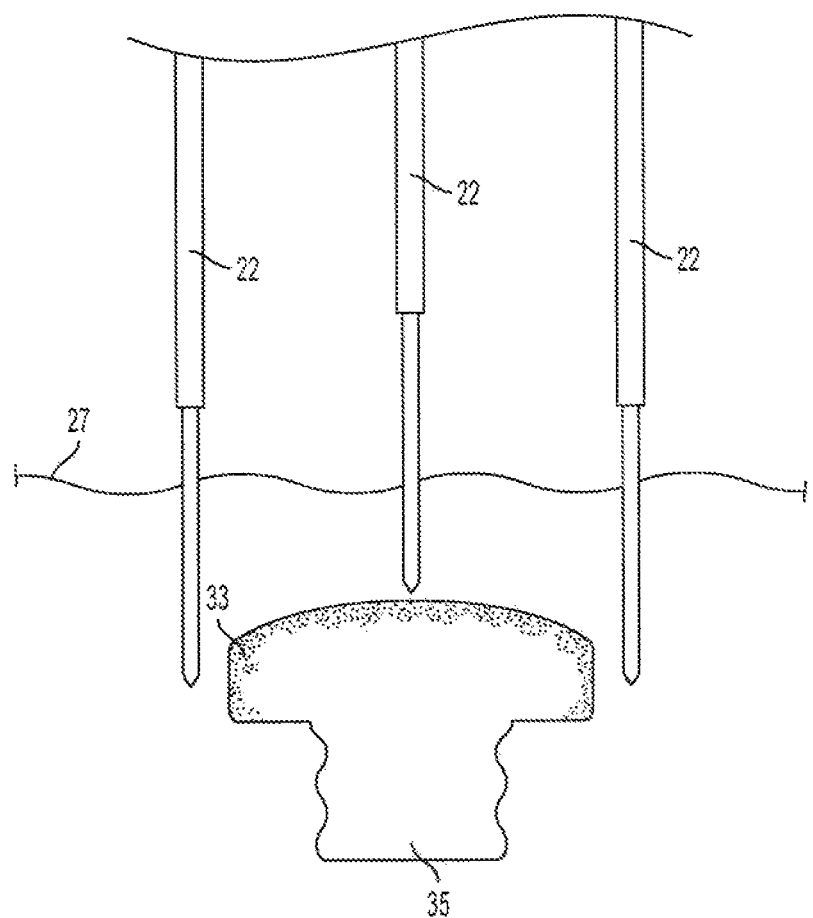
FIGS. 36A and 36B illustrate a method of treating infected tissue and/or sterilizing an implanted medical device, such, as for, example, a cartilaginous implant.
Figure 36B:
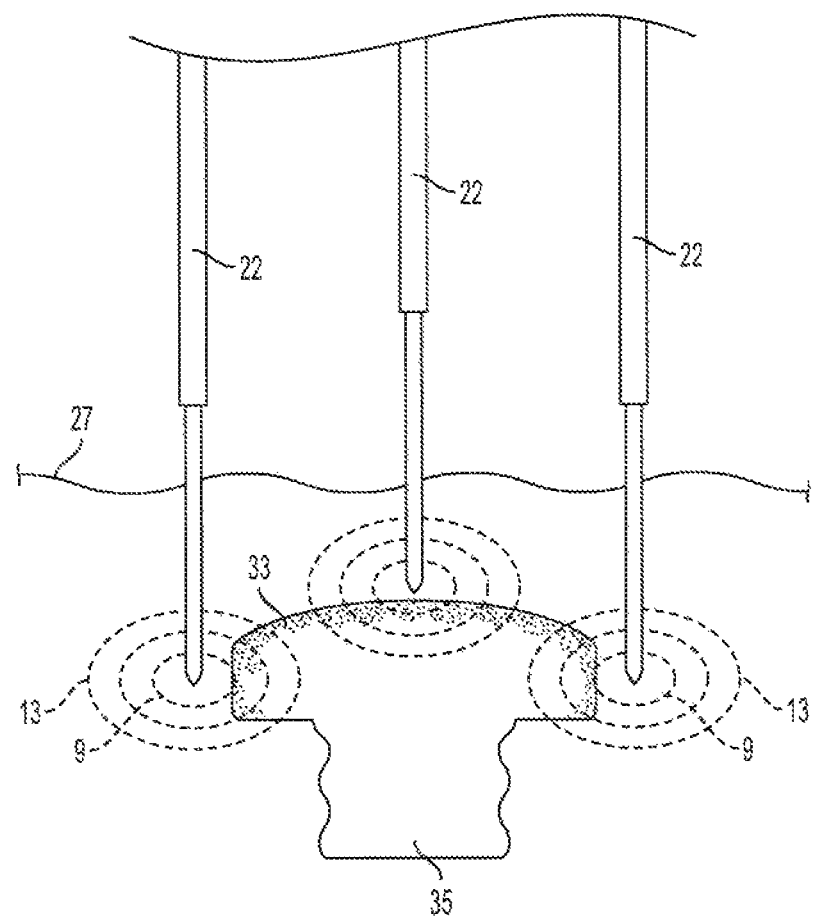

As illustrated in FIGS. 36A and 36B, a method of treating infectious cell growth 33 on an implanted medical device, such as a cartilaginous implant 35, using IRE is disclosed. Although three (3) probes are illustrated in the method, any number of suitable probes can be used to deliver the electrical pulses. When electrical pulses are administered within the irreversible parameter ranges, as described above, permanent pore formation occurs in the cellular membrane, resulting in cell death of the targeted infectious cells 33. In another aspect, by proactively administering the electrical pulses according to a predetermined schedule, infectious cell growth 33 on an implanted medical device can be prevented altogether. Alternatively, electrical pulses may be administered within a reversible electroporation range. Temporary pores will form in the cellular membranes of infectious cells.

The voltage pulse generator 10 can be configured to generate electrical pulses between electrodes 22 in an amount which is sufficient to induce irreversible electroporation of infectious cells that may be present on or near an implanted medical device without creating a clinically significant thermal effect to the surrounding tissue or critical structures. Specifically, the electrical pulses can create permanent openings in infectious cells of smooth muscle cells, for example, thereby invoking cell death without creating a clinically significant thermal effect. The infectious cells 33 will remain in situ and can be subsequently removed by natural body processes. These infectious cells can be located anywhere along the implantable medical device. Research has also shown that growths of infectious cells can enhance implanted medical device-related bacteremia by providing an interface for adherence and colonization. These pathogens may then produce a "biofilm" which is impenetrable to systemic antibiotics leading to a cause of implanted medical device dysfunction, subsequent removal, and the attendant increases in morbidity and mortality. These biofilms can also lead to chronic microbial infection, inflammation, and tissue necrosis. These infections are frequently due to gram-positive bacteria, such as *Staphylococcus epidermidis* or *Escherichia coli* in the case of catheter-associated or other plastic-types of medical devices and *Staphylococcus aureus* in the case of metallic implants. However, other types of bacteria could be present as well, such as, but not limited to, *Streptococcus mutans, Streptococcus mitus, Streptococcus salivarius*, and *Enterobacter aerogenes*. Initial infection is always linked to the ability of the bacteria to adhere to material surfaces. At first the bacterial adhesion is reversible, but then later becomes irreversible. Over time, the individual microorganisms and bacterial matrix formation can develop a high resistance to antibiotics.

As illustrated in FIG. 36B, as electrical pulses are delivered to the target implanted device, a series of electrical field lines can be generated. The strongest (defined as volts/cm) electrical field is nearest to the electrodes 22 and is depicted by gradient line 9. As the distance away from the electrodes 22 increases, the strength of the electrical field decreases. Outer gradient line 13 represents the outer perimeter of electric field gradient. As an example, any infectious cells 33 or other bio-film growth on the surface of the implantable medical device 35 within the outer perimeter 13 will undergo cell death by irreversible electroporation. Because the voltage pulse generation pattern from the generator does not generate damaging thermal effect, and because the voltage pulses only ablate living cells, the treatment does not damage blood, blood vessels or other non-cellular or non-living materials such as the implantable device itself.

Referring again to FIG. 36B, the pulse parameters that characterize the field gradient line can be adjusted to vary the treatment zone according to the location of the infectious cells growth and/or infectious cells to be destroyed. Furthermore, in some embodiments of the invention, the electrodes can be positioned at any location necessary to destroy any such infectious cells 33 that have grown around or on the indwelling implanted medical device 35. For example, the electrodes 22 can be positioned at a proximal section of the implanted device for treating infectious cells that have grown around the implanted device, at a distal section of the implanted device, or surrounding the implanted medical device. In addition, the electrodes 22 can be positioned to destroy infectious cells 33 that have grown near the insertion site of the implanted device.

In another aspect of the invention, by periodically administering the electrical pulses according to a predetermined schedule, infectious cell growth on the implanted device can be prevented altogether. As an example, the formation of infectious cells may occur as early as 24 hours after implanted medical device implantation. Application of electrical pulses applied to the implanted medical device at regular intervals post-implantation may be effective in preventing infectious cell growth during the implanted medical device implantation period.

Figure 37:
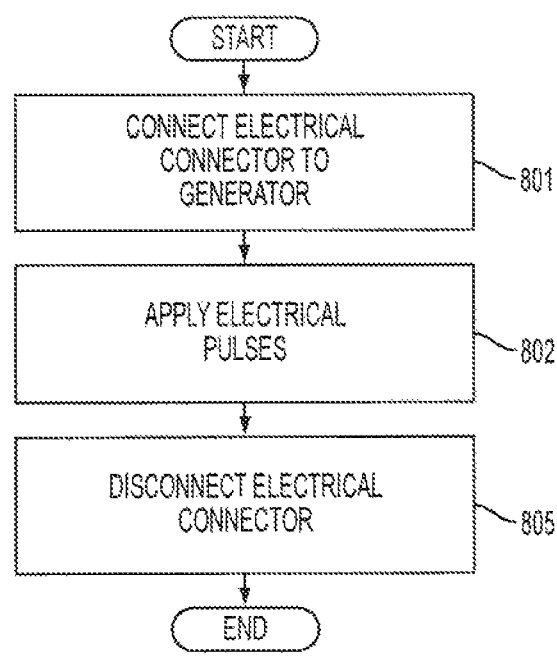
FIG. 37 is a flowchart depicting the method steps for infectious cell ablation using irreversible electroporation methods described herein.

FIG. 37 illustrates the procedural steps associated with performing irreversible or reversible electroporation treatment using any of the probe devices described herein. After the infectious cell formation 33 has been detected and the location determined using ultrasound or fluoroscopic imaging, electrode probes 22, as illustrated in FIG. 36A, are inserted into the patient's skin 27 such that the probes can be near or in contact with the infectious cell growth on the implanted medical device. The probes 22 are then positioned relative to the infectious cells' 33 location as previously described. The electrodes 22 can be deployed and positioned outside of the implanted medical device 35 as shown in FIGS. 36A and 36B. Electrical connectors from each probe are connected (801) to generator 10 using an extension cable. This completes an electrical circuit between the electrodes 22 and the generator 10. Electrical pulses are applied across the electrodes 22 in the desired pattern (802) to electroporate the smooth muscle cells of the infectious cells 17. Electrical pulses are then applied across the electrodes 22 creating field gradient lines 9 and 13, for example, as illustrated in FIG. 36B, sufficient to non-thermally electroporate the infectious cells. As illustrated in FIG. 37, after treatment, the extension cable is disconnected from the electrical connector (805) and the probes are removed from the tissue. Non-thermal death of the infectious cells 33 will occur within the first twenty-four hours after electroporation treatment followed by a cellular breakdown of the infectious cells.

In one embodiment, the electroporation pulses can be synchronously matched to specifically repeatable phases of the cardiac cycle to protect cardiac cellular functioning. See, for example, U.S. Patent Application No. 61/181,727, filed May 28, 2009, entitled "Algorithm For Synchronizing Energy Delivery To The Cardiac Rhythm", which is fully incorporated by reference herein. This feature is especially useful when the electroporation pulses are delivered in a location that is near the heart. This can be especially useful if a user is attempting to treat infection near an implanted medical device such as a pacemaker. FIG. 38 illustrates a treatment setup for a patient for synchronization of the delivery of electroporation pulses with a specific portion of the cardiac rhythm. Electrocardiogram (ECG) leads 17, 19, 21 are adapted to be attached to the patient for receiving electrical signals which are generated by the patient's cardiac cycle. The ECG leads transmit the ECG electrical signals to an electrocardiogram unit 29. The electrocardiogram unit 29 can transmit this information to a synchronization device 25 which can include hardware or software to interpret ECG data. If the synchronization device 25 determines that it is safe to deliver electroporation pulses, it sends a control signal to a pulse generator 10. The pulse generator 10 is adapted to connect to the electrical connector for delivering electroporation pulses. Each of the synchronization device 25 and pulse generator 10 can be implemented in a computer so that they can be programmed.

The present invention affords several advantages. Infectious cell growths 33 are destroyed without having to remove the implanted medical device 35 from the patient. The treatment is minimally-invasive and highly efficacious. Because irreversible electroporation does not create thermal activity, the implanted medical device 35 is not damaged by the treatment. Infectious cells growths 33 are treated quickly, and the implanted medical devices 35 can be maintained according to a predetermined schedule to insure that they are routinely treated with IRE to remove the infected cells 33.

Although the irreversible electroporation device and method has been described herein for use with cartilaginous implanted medical devices, it should be understood that the irreversible electroporation device can be used with any type of implanted medical device 35, such as, but not limited to, ports, catheters, stents, artificial cartilaginous implants, orthopedic prosthetics, pacemakers, PICCs, hip implants, tooth implants, heart valves, spinal implants, and other types of plastic and/or metallic devices, to name a few. While the embodiments shown use pulses that cause IRE, persons of ordinary skill in the art will appreciate that other types of pulses can be used for the destruction of the infectious cell growths 33. In particular, ultrashort sub-microsecond pulses (pulses of less than 1 microsecond in duration) can be used to induce apoptosis that cause damage to the intracellular structures such as a cell nucleus.

In yet another embodiment, the method of IRE treatment described herein could be used to treat one or more parts of a patient's body that are infected due to some other infection, such as, for example, gangrene. Gangrene is particularly problematic in patients with poor blood flow, such as diabetic patients, particularly in certain parts of the body, such as the extremities (i.e., hands, feet, nose, ears, etc.). Gangrene is a type of necrotizing (flesh-destroying) bacterial infection. Typically, a physician prescribes antibiotics to a patient to treat gangrene. However, poor circulation can prevent certain drugs from reaching these extremities, thereby making patients more susceptible to infection in these areas. Gangrene often spreads so quickly that it can't be stopped by antibiotics alone. In some cases, the gangrene can cause lesions in the skin. At most, antibiotics may help slow the infection and clear small, unnoticed pockets of bacteria. A surgeon may still have to debride or cut away the infected flesh and a margin around it to prevent further spread. If debridement isn't enough, amputation is the next step. During this procedure the patient is put in a hyperbaric chamber if one is available. This is a sealed metal tank pumped full of oxygen under high pressure. The pressure forces oxygen into the tissues, stopping the spread of anaerobic bacteria. All of these methods have pitfalls. For example, patients can build up a resistance to antibiotics, as described above. Surgery to excise infected flesh can be expensive, time-consuming, and most importantly, painful for the patient. As an alternative, IRE methods of treatment, as described above using any of the pulse parameters disclosed herein, could be used in such tissues to effectively kill gangrene tissue, allowing healthy tissue to regenerate, thereby eliminating the need for amputation.

In yet another aspect, IRE could be used to treat infected cells present on the patient's tissue scaffold. A patient's own natural tissues could be used as a scaffold. The IRE electrical pulses can effectively de-cellularize the tissue scaffold in a desired target tissue zone of infectious cells 33, while leaving the tissue scaffold intact. After IRE is performed on or near the tissue scaffold, then the patient's tissue can naturally re-cellularize onto the patient's natural tissue scaffold after IRE has been performed. This method allows vascular, neural, and other critical structures to remain intact and essentially unharmed. However, even if the IRE pulses target collateral structures, this method would still be a safe alternative to other forms of cellular ablation or decellularization such as physical, chemical, or enzymatic methods of decellularization. Such treatments can be very harsh and can degrade the tissue scaffold as well as the vasculature and neural structures. Furthermore, such methods are often insufficient by themselves to achieve decellularization alone, and often have to be combined with each other to achieve the desired result. These methods can also compromise the structure of the extracellular matrix (ECM).

In contrast, the use of IRE to decellularize infected tissue can provide a controlled, precise way to destroy cells of a tissue or organ, while leaving the underlying extracellular matrix intact, including the vascular and neural structures as well as other critical features intact. IRE can also prevent scar tissue formation as well as promote a beneficial immune response. The method could involve treating in vitro or in vivo, a tissue comprising infectious cells located on an underlying scaffold with electrical pulses of sufficient duration and power to kill infectious cells of the tissue, while leaving the extracellular matrix and other vascular and neural structures intact. As used herein, the term "intact" means a state of being whereby an element is capable of performing its original function to a substantial extent.

In one aspect, any of the IRE methods and parameters described herein can be used to deliver electrical pulses to the infectious cells present on the tissue scaffold. Any suitable frequency of pulsing that allows for irreversible electroporation without significant thermal damage to the tissue is acceptable. In one embodiment, the electrodes 22 described herein can be placed into or near the vicinity of the tissue scaffold to cause irreversible electroporation of the infectious cells on or near the tissue scaffold. The electrical pulses irreversibly permeabilize the membranes of the infectious cells, thereby invoking cell death. The length of time of the electrical pulses, the voltage applied, and the resulting membrane permeability are all controlled within desired ranges. The debris left by the infectious cells may be left in situ and may be removed by natural processes, such as the body's own immune or circulation system.

In another exemplary embodiment, IRE could be used to ablate cysts in the abdomen. A cyst is an overgrowth of the epithelium, comprising specialized cells that reside on the surface of tissue, such as organs and glands. Once formed, they often become detached from the point of origin and circulate, although they may also become lodged between tissue structures and cause pressure. They generally appear as sacs or lumps surrounded by a thin membrane and consist of fluid or semi-solid material. While most cysts are benign, the development of an abdominal cyst may signal an underlying disease.

There are several types of abdominal cysts. One of the most common is an ovarian cyst, which forms on ovarian follicles. Even though most ovarian cysts are benign, they can cause pain and bleeding. Standard treatment to remove cysts involves surgical removal if they become too large. Mesenteric cysts are another type of abdominal cyst that may indicate impaired lymphatic functioning. These types of cysts develop in the mesentery, the area of the peritoneum that encompasses the gastrointestinal tract and extends from the duodenum to the rectum. In addition, these cysts may involve any of the organs of the retroperitoneum, such as the bladder and kidneys. Omental cysts generally occur in the anterior abdominal wall in the regions of the stomach and colon. These types of cysts can usually be removed without having to resection the stomach or colon. While most abdominal cysts are not dangerous, they can sometimes grow from the size of a pea to a grapefruit over time and can sometimes present complications. Abdominal cysts can also cause pain, unexplained bleeding, bowl obstruction, and distension of the stomach or other organs, should be investigated without delay. Typical treatment modalities to remove cysts include surgical measure. However, surgery can be time-consuming, painful, and expensive.

In one aspect, IRE treatment methods, as described herein, can be used as a minimally invasive and safe procedure to ablate and remove benign abdominal cysts as well as abdominal cancer cells. IRE methods can be more efficient, cheaper, and less painful compared to surgical procedures and would leave critical structures intact, such as vascular structures, etc. Even if the collateral structures are affected, using non-thermal IRE as a treatment method for removal of abdominal cysts would provide a safe treatment alternative to thermal or surgical removal methods that can be time-consuming, costly, and painful for the patient or the use of drugs that can have harmful side effects.

Another example of infected tissue that can be treated using IRE is infected bone, or osteomyelitis. Bone infections can be extremely difficult to treat. Typically, bone infections can be treated using surgical procedures. The bone can be accessed by variety of procedures, such as through the skin. After the bone is surgically cleaned out, the remaining bone defect(s) is treated with a large dose of antibiotics via a non-resorbable bone cement to eradicate any bacterial cells in the bone and bloodstream. After this, subsequent surgery is required for removal and replacement with a bone graft or an absorbable mix of synthetic bone substitute. After all of these bone cleaning and replacements, the bone is typically not strong enough to bear weight. Bone rebuilding techniques can involve bone grafting or bone transport. Antibiotic treatment is then administered through an intravenous catheter. These treatment procedures have the attendant disadvantages mentioned above.

Instead of using the above-described extensive, painful, and expensive procedures, IRE can be used to treat bone infection. In one aspect, sufficient electrical pulse parameters can be selected, as described herein above, to irreversibly electroporate infected cells that are present within or along bone. In one aspect, the electrical probes described herein can be inserted into a target tissue surrounding an infected bone, and sufficient electrical pulse parameters could be selected to adequately irreversibly electroporate an infected bone. In one embodiment, an outer layer of bone could be treated to remove infected cells. When infected tissue of a bone is irreversibly electroporated, such target bone tissue could include muscle and/or vessels which could be acutely necrosed. However, in time, the critical cellular and/or vascular structures could grow back so that no long term harmful consequences would occur.

IRE could also be used to sterilize implanted medical devices using any of methods comprising any of the electrical pulse parameters described herein. Implanted medical devices such as metallic devices could be sterilized using the device itself as a conductor. In one aspect, the metallic device could be comprised of stainless steel, cobalt-chromium-molybdenum alloys, pure titanium, or titanium alloys. The implanted medical device, functioning as a conductor, could be placed between two electrodes, for example, thereby effectively functioning as another electrode. In another embodiment, a plurality of electrodes could be used and placed surrounding the implanted medical device. A practitioner can position the electrodes a predetermined distance from the implant so that the implanted medical device can function like a return electrode. When IRE is performed, the electric field lines 9 through 13 could travel from each electrode to the outer surface of the implant, thereby allowing the implant to effectively become part of the sterilization.

In summary, the use of IRE to sterilize such medical devices and/or treat infected tissue can be an effective alternative to RF, cryo, or other scar-prone surgical procedures. This method can be used proactively to ensure that deep-seated infection will not occur post-operatively. This would prevent tissues from being permanently scarred. This method is beneficial because after IRE is performed, healthy tissue will grow instead of scar tissue. The use of this procedure could also provide better long term results for patients and would eliminate the need to have patients endure multiple surgeries and lengthy healing times.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. A method of treating infected tissue of a patient comprising:
   placing two electrodes near a treatment site, wherein the treatment site comprises the infected tissue;
   activating a generator, the generator to be operatively coupled to the two electrodes, the generator to generate electrical pulses to be delivered between the two electrodes;
   wherein the electrical pulses are sufficient to irreversibly electroporate the infected tissue while leaving intact a natural tissue scaffold of the patient within the treatment site;
   wherein the treatment site further comprises a pre-inserted medical device, wherein the pre-inserted medical device is comprised of a conductive material, wherein the pre-inserted medical device functions as a return electrode.

2. The method of claim 1, wherein the electrical pulses reduce a likelihood of irreversible damage to a neural structure near the treatment site or a neural structure within the treatment site.

3. The method of claim 1, wherein the electrical pulses are sufficient to promote an immune response in the patient.

4. The method of claim 1, wherein the electrical pulses are sufficient to promote re-cellularization on the tissue scaffold.

5. The method of claim 1, wherein the electrical pulses reduce a likelihood of scar tissue forming within the treatment site.

6. The method of claim 1, wherein the electrical pulses decrease a likelihood of causing irreversible damage to blood vessels within the treatment site.

7. The method of claim 1, wherein the infected tissue comprises bone.

8. The method of claim 1, wherein the infected tissue comprises gangrene.

9. The method of claim 1, wherein the infectious cells comprise any of the following: a gram-positive bacteria, *Staphylococcus epidermidis, Escherichia coli, Staphylococcus aureus, Streptococcus mutans, Streptococcus mitus, Streptococcus salivarius*, or *Enterobacter aerogenes*.

10. A method of decellularizing infected tissue comprising:
    placing a probe near a treatment site comprising the infected tissue; the probe comprises at least one electrode;
    activating a generator operatively coupled to the probe, the generator generates electrical pulses to be delivered through the at least one electrode are sufficient to irreversibly electroporate cells of the infected tissue leaving intact an underlying extracellular matrix of the infected tissue;
    wherein the treatment site further comprises a pre-inserted medical device, wherein the pre-inserted medical device is comprised of a conductive material, wherein the pre-inserted medical device functions as a return electrode.

11. The method of claim 10, wherein the electrical pulses are sufficient to promote an immune response.

12. The method of claim 10, wherein the electrical pulses are sufficient to leave intact vascular structures present in the treatment site.

13. The method of claim 12, wherein the electrical pulses reduce a likelihood to cause irreversible damage to neural structures present in the treatment site or neural structures present near the treatment site.

14. The method of claim 10, wherein the electrical pulses are sufficient to promote tissue re-cellularization.

15. A method of treating a patient with an infected tissue site comprising:
   placing a probe comprising at least two electrodes near the infected tissue site comprising an infected tissue;
   activating a generator operatively coupled to the at least two electrodes, the generator to deliver electrical pulses between the at least two electrodes, the electrical pulses are configured to:
      irreversibly electroporate the infected tissue;
      leave intact a patient specific natural tissue scaffold within the treatment site; and
      promote an immune response within the patient;
   wherein the treatment site further comprises a pre-inserted medical device, wherein the pre-inserted medical device is comprised of a conductive material, wherein the pre-inserted medical device functions as a return electrode.

16. The method of claim 15, wherein the infected tissue site comprises a pre-inserted medical device.

17. The method of claim 16, wherein the pre-inserted medical device comprises any of the following: a port, a catheter, a stent, an artificial cartilaginous implant, an orthopedic prosthetic, a pacemaker, a pre-inserted central catheter, a hip implant, a tooth implant, a heart valve, or a spinal implant.

* * * * *